(12) United States Patent
Nag et al.

(10) Patent No.: US 12,195,418 B2
(45) Date of Patent: Jan. 14, 2025

(54) HALOGENATED BENZYLIDENE DERIVATIVES

(71) Applicant: Renovel Innovations, Inc, Fremont, CA (US)

(72) Inventors: Bishwajit Nag, Union City, CA (US); Ananda Sen, Castro Valley, CA (US); Nitish Nag, Union City, CA (US); Arjun Sanyal, Castro Valley, CA (US); Srinivasan Narasimhan, Chennai (IN)

(73) Assignee: Renovel Innovations, Inc., Fremont, CA (US)

( * ) Notice: Subject to any disclaimer, the term of this patent is extended or adjusted under 35 U.S.C. 154(b) by 293 days.

(21) Appl. No.: 17/584,189

(22) Filed: Jan. 25, 2022

(65) Prior Publication Data

US 2023/0107812 A1   Apr. 6, 2023

Related U.S. Application Data

(60) Provisional application No. 63/141,880, filed on Jan. 26, 2021.

(51) Int. Cl.
| | | |
|---|---|---|
| *C07D 251/24* | (2006.01) | |
| *C07C 229/36* | (2006.01) | |
| *C07C 251/24* | (2006.01) | |
| *C07D 213/74* | (2006.01) | |
| *C07D 213/80* | (2006.01) | |

(52) U.S. Cl.
CPC .......... *C07C 251/24* (2013.01); *C07C 229/36* (2013.01); *C07D 213/74* (2013.01); *C07D 213/80* (2013.01)

(58) Field of Classification Search
CPC .. C07D 213/74; C07D 213/80; C07C 251/24; C07C 229/36
See application file for complete search history.

(56) References Cited

U.S. PATENT DOCUMENTS 5,594,012 A * 1/1997 Kitazawa ............. C07C 279/14
548/506

OTHER PUBLICATIONS

Bharti, J Indian CHem Soc, vol. 93, Aug. 2016, 953-964. (Year: 2016).*
Gama, Arkivoc 2003, Organic Chemistry in MExico, 4-15. (Year: 2003).*
Sheehan, J Chem Soc, 1962, vol. 84, 2417-2420. (Year: 1962).*
Abdel, Arabian J of hcem, vol. 10, 2017, S1835-S1846. (Year: 2017).*
Pradeep, J Chem Sci, vol. 118, No. 4, 2006, 311-317. (Year: 2006).*
Palkar, Med Chem Res, 2015, vol. 24, 1988-2004. (Year: 2015).*
Bharti, J. Indian Chem Soc., Aug. 2016, vol. 93, p. 953-964.
Gama, Arkivoc 2003, Organic Chemistry in Mexico, p. 4-15.
Sheehan, J Chem Soc., 1962, vol. 84, p. 2417-2420.
Abdel, Arabian J of Chem, 2017, vol. 10, p. S1835-S1846.
Pradeep, J Chem Sci, 2006, vol. 118, No. 4, p. 311-317.
Palkar, Med Chem Res, 2015, vol. 24, p. 1988-2004.

* cited by examiner

*Primary Examiner* — D Margaret M Seaman
(74) *Attorney, Agent, or Firm* — GSS Law Group; Adam Warwick Bell

(57) ABSTRACT

Novel Halogenated Benzylidine derivatives are provided which exhibit activity for the treatment of immunological diseases and inflammation.

5 Claims, 34 Drawing Sheets

Control

Indomethacin

Aspirin

Compound 8

HALOGENATED BENZYLIDENE DERIVATIVES

RELATION TO OTHER APPLICATIONS

This application claims the benefit of and priority to U.S. Provisional Application No. 63/141,880 filed 26 Jan. 2021, which is incorporated herein by reference.

FIELD OF THE INVENTION

The present invention relates to novel halogenated benzylidene derivatives for the treatment of immunological diseases, autoimmune disorders, and inflammation.

BACKGROUND OF INVENTION

Inflammation is part of the complex biological response of vascular tissues to harmful stimuli, such as pathogens, damaged cells, or irritants. The classical signs of acute inflammation are pain, heat, redness, swelling, and loss of function. Inflammation is a protective attempt by the organism to remove the injurious stimuli and to initiate the healing process. Inflammation is not a synonym for infection, even in cases where inflammation is caused by infection. Progressive destruction of the tissue would compromise the survival of the organism. However, chronic inflammation can also lead to a host of diseases, such as hay fever, periodontitis, atherosclerosis, rheumatoid arthritis, and even cancer (e.g., gallbladder carcinoma). Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

Drugs to treat acute and chronic inflammation are known as "Anti-inflammatory drugs". Anti-inflammatory drugs make up about half of analgesics, remedying pain by reducing inflammation as opposed to opioids, which affect the central nervous system.

Many steroids, to be specific glucocorticoids, reduce inflammation or swelling by binding to glucocorticoid receptors. These drugs are often referred to as corticosteroids. Non-steroidal anti-inflammatory drugs (NSAIDs), alleviate pain by counteracting the cyclooxygenase (COX) enzyme. On its own, COX enzyme synthesizes prostaglandins, creating inflammation. In whole, the NSAIDs prevent the prostaglandins from ever being synthesized, reducing or eliminating the pain.

Some common examples of NSAIDs are: aspirin, ibuprofen, and naproxen. The newer specific COX-inhibitors—although, it is presumed, sharing a similar mode of action—are not classified together with the traditional NSAIDs.

Long-term use of NSAIDs can cause gastric erosions, which can become stomach ulcers and in extreme cases can cause severe hemorrhage, resulting in death. The risk of death as a result of use of NSAIDs is 1 in 12,000 for adults aged 16-45. The risk increases almost 20-fold for those over 75. Other dangers of NSAIDs are exacerbating asthma and causing kidney damage. Apart from aspirin, prescription and over-the-counter NSAIDs also increase the risk of myocardial infarction and stroke.

Several biological protein-based therapeutics especially monoclonal antibodies emerged as new class of treatment for inflammatory conditions specifically RA and IBD in recent years. These products are highly expensive and develop anti-idiotypic effects with chronic condition treatments. Therefore, need for new classes of anti-inflammatory molecules are in great demand. The present invention describes synthesis of new class of compounds originally isolated from natural product source and then structurally modified with minimum side effects.

The compounds and compositions of the present invention are used to treat diseases associated with Inflammation, which include (but are not limited to) the following: Chron's Disease, Appendicitis, Bursitis, Colitis, Cystitis, Dermatitis, Epididymitis, Gingivitis, Meningitis, Myelitis, Nephritis, Neuritis, Pancreatitis, Periodontitis, Pharyngitis, Phlebitis, Prostatitis, Sinusitis, Tendonitis, Tonsillitis, Urethritis, Vasculitis, Vaginitis, Rheumatoid Arthritis, Osteoarthritis, Psoriatic Arthritis, Septic Arthritis, Chronic Inflammation, Asthma, Hepatitis, Laryngitis, Thyroiditis, Lymphangitis, Gout, Arteritis, Bronchitis, Acne Vulgaris, Pneumonia, Sarcoidosis, Endocarditis, Myocarditis, Pericarditis, Duodenitis, Esophagitis, Folliculitis, Anemia, Hypersensitivity, Chronic Obstructive Pulmonary Disease, Complex Regional Pain Syndrome, Rhinitis and Celiac Disease.

SUMMARY OF INVENTION

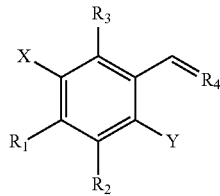

The present invention relates to novel Halogenated Benzylidene derivatives of the formula (I) their derivatives, their analogs, their tautomeric forms, their stereoisomers, their polymorphs, their pharmaceutically acceptable salts, their pharmaceutically acceptable solvates, wherein X corresponds to any halogen, Y corresponds to hydrogen, any halogen, hydroxyl, alkoxy, nitro, amino or sulphonyl groups; $R_1$ and $R_3$ corresponds to H, OH or alkyl chain with any number of carbon atoms or modifications therein; $R_2$ corresponds to a free hydroxyl group or extended chain through an alkyloxy ester or un-substituted or substituted aryloxy ester groups; $R_4$ corresponds to any naturally occurring or synthesized amino acid, their derivatives like amino acid alcohol and amino acid ester, condensed through their free amino group. Also, $R_4$ corresponds to un-substituted or substituted aryl amines, pyridyl amine and amino benzoic acid wherein the free amine group condenses to form the Halogenated Benzylidene compound with the gross formula represented in FIG. 1. The compounds derived from the saturation of the double bond to $R_4$ are also included.

The present invention also relates to a process for the preparation of the above said novel compounds, their analogs, their tautomeric forms, their stereoisomers, their polymorphs, their pharmaceutically acceptable salts, their pharmaceutically acceptable solvates, novel intermediates and pharmaceutical composites containing them. Tautomeric forms are isomeric forms which exists in a state of equilibrium capable of reacting according to either form. Stereoisomers include configurational isomers, such as cis- and trans double bonds, as well as optically active isomers having different spatial arrangements of their atoms. Polymorphs are molecules which can crystallize in two or more forms. Solvates are molecular or ionic complexes of molecules or ions of solvent with those of a solute. The amino acid derivatives are included, but not limited to naturally occurring amino acids. Analogs include those compounds which differ by substitution of an oxygen, sulphur, nitrogen or carbon atom in place of such an atom. Analogs also include atoms of the same family of the Periodic Table, such as F, Cl, Br and I. Derivatives include compounds resulting from routine functionalizing of atoms, such as, derivatives found by protecting amino or carboxyl groups by carboxylation or esterification, respectively.

DETAILED DESCRIPTION OF THE INVENTION

In an embodiment of the present invention, the group represented as X can be selected from any halogen such as Fluorine, Chlorine, Bromine and Iodine, and Y is selected from hydrogen, halogen such as fluorine, chlorine, bromine or iodine; hydroxyl, nitro, cyano, formyl, amino or sulfonyl groups and the like.

In an embodiment of the present invention, the groups represented by $R_1$ and $R_3$ are selected from linear or branched, substituted or unsubstituted ($C_1$ to $C_{12}$) alkyl groups such as methyl, ethyl, propyl, isopropyl, n-butyl, isobutyl, t-butyl, pentyl, hexyl, octyl, nonyl and the like; substituted or unsubstituted ($C_1$ to $C_{12}$) alkoxy group such as methoxy, ethoxy, propoxy, butoxy and the like.

Figure 1:
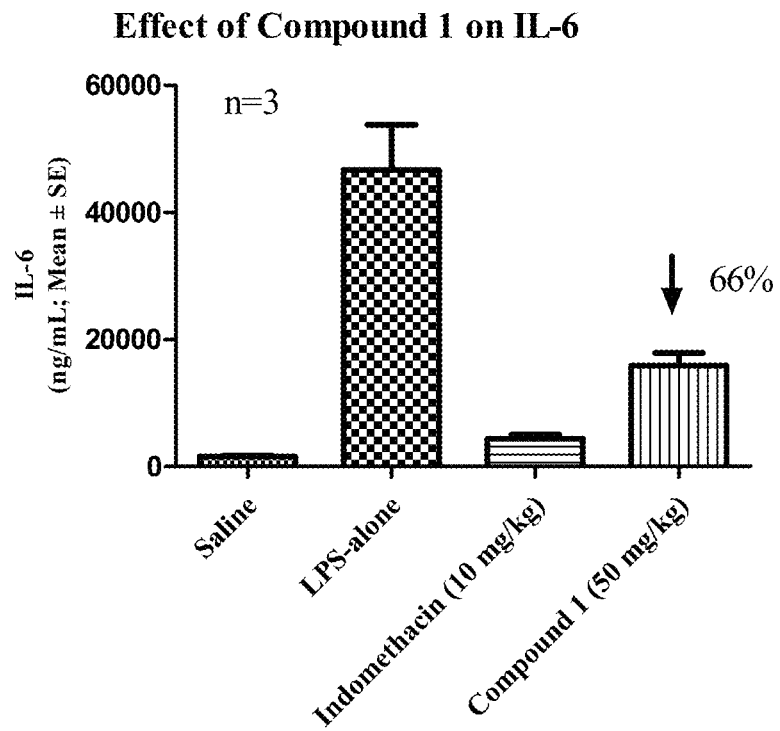
FIG. 1 shows that the group of mice administered with Compound 1 showed a 66% decrease of IL-6 from the LPS group.
Figure 2:
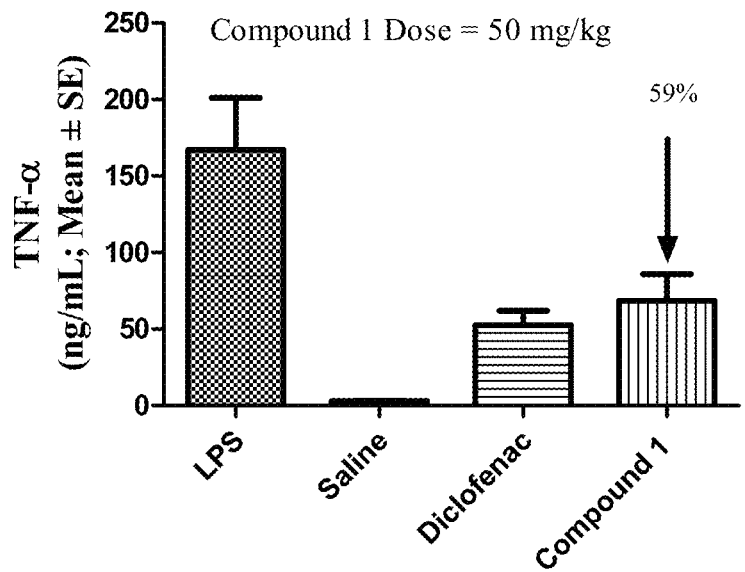
FIG. 2 shows that mice administered with Compound 1 showed a 59% decrease of TNF-α from the LPS group.
Figure 3:
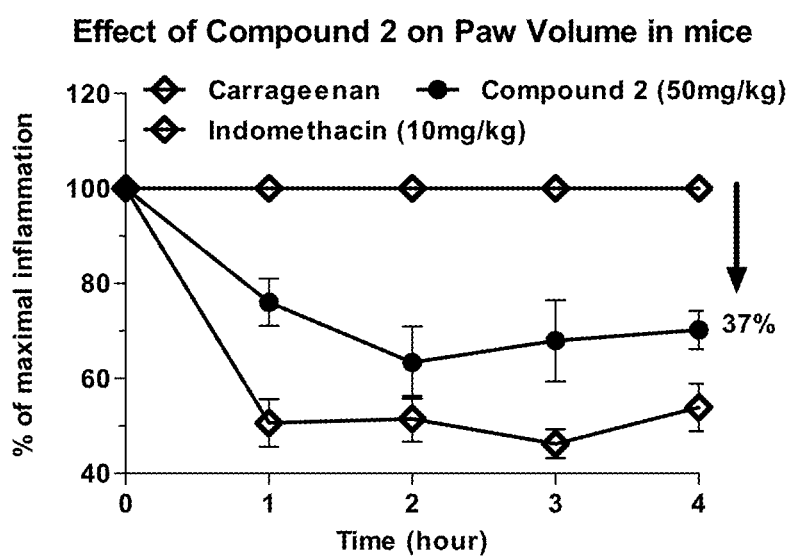
FIG. 3 shows that the group of rats administered with Compound 2 showed a 37% decrease in right hind leg volume.
Figure 4A:
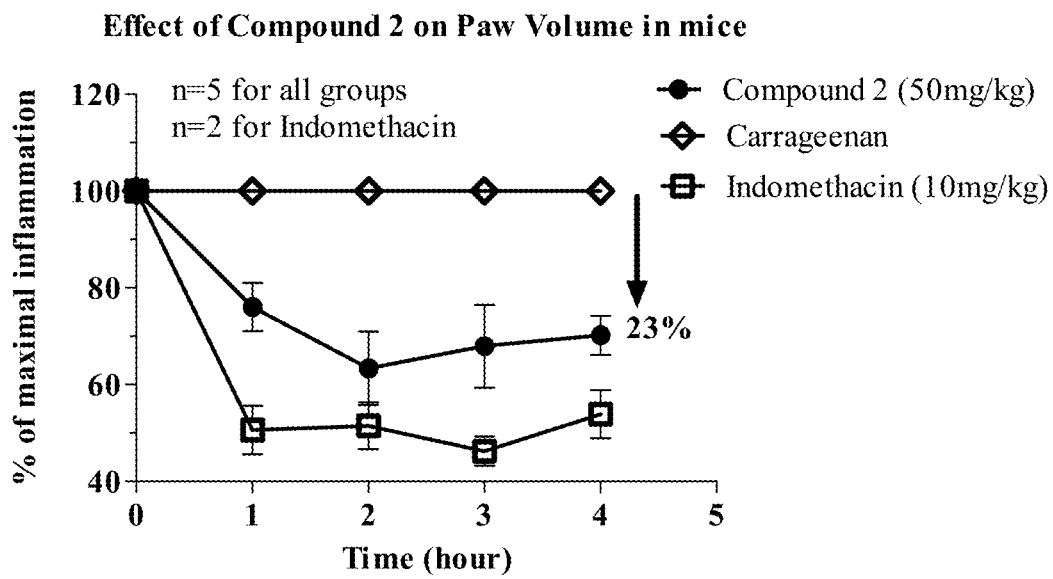
FIG. 4 shows that rats administered with Compound 2 showed a 23% decrease in right hind leg volume (FIG. 4A). The group of rats administered with Compound 2 showed a 31% decrease in right hind leg thickness (FIG. 4B).
Figure 4B:
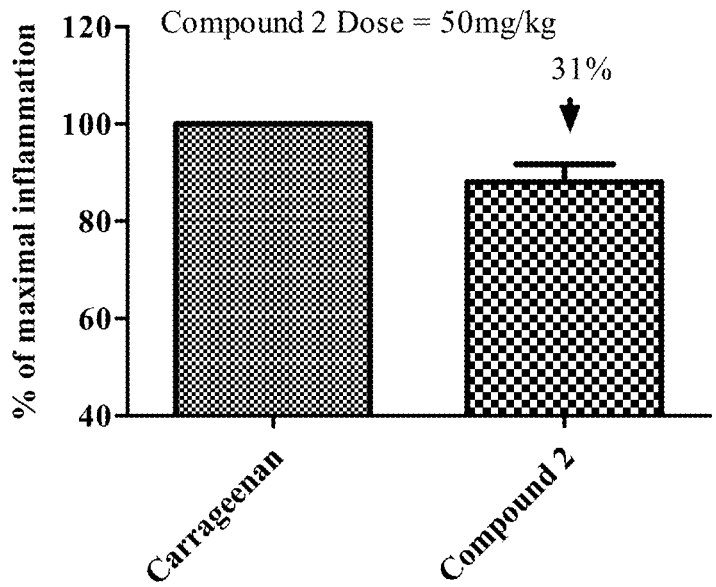
Figure 5A:
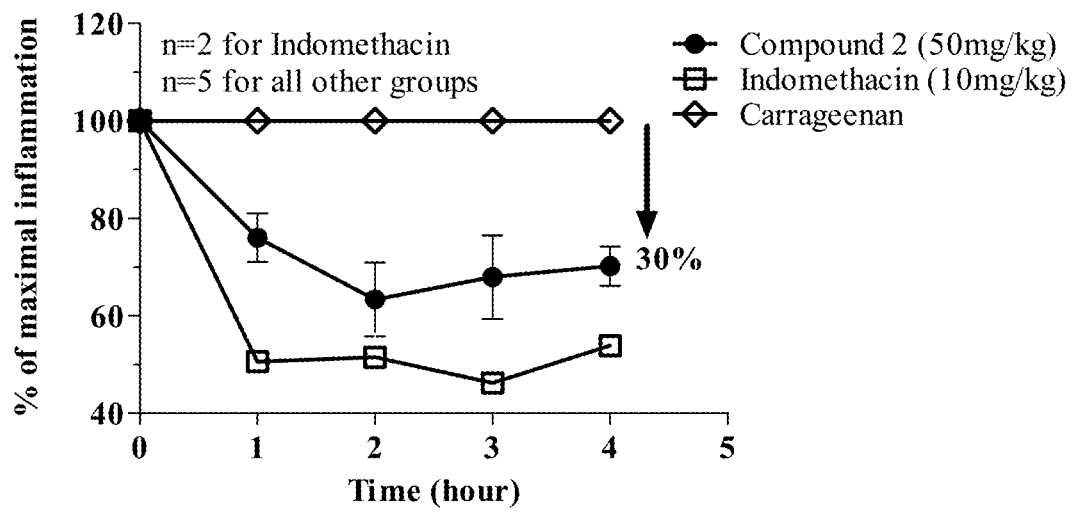
FIG. 5 shows that rats administered with Compound 2 showed a 30% decrease in right hind leg volume (FIG. 5A). The right hind leg thickness was measured using calipers. The group of rats administered with Compound 2 showed a 12% decrease in right hind leg thickness (FIG. 5B).
Figure 5B:
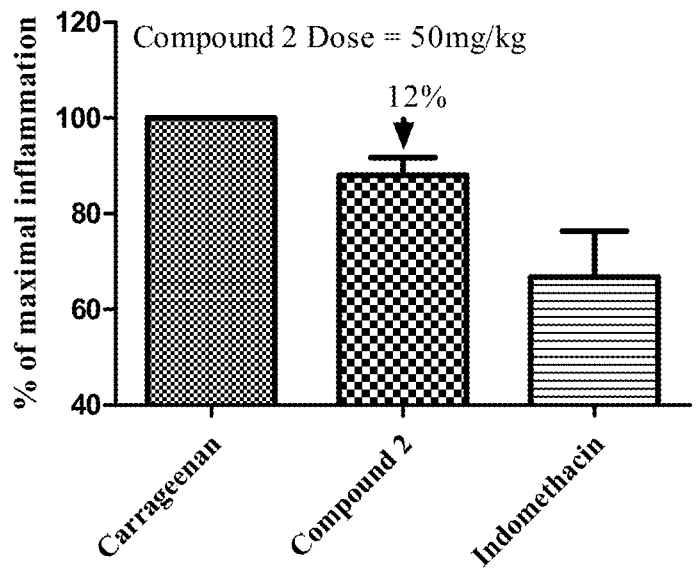
Figure 6:
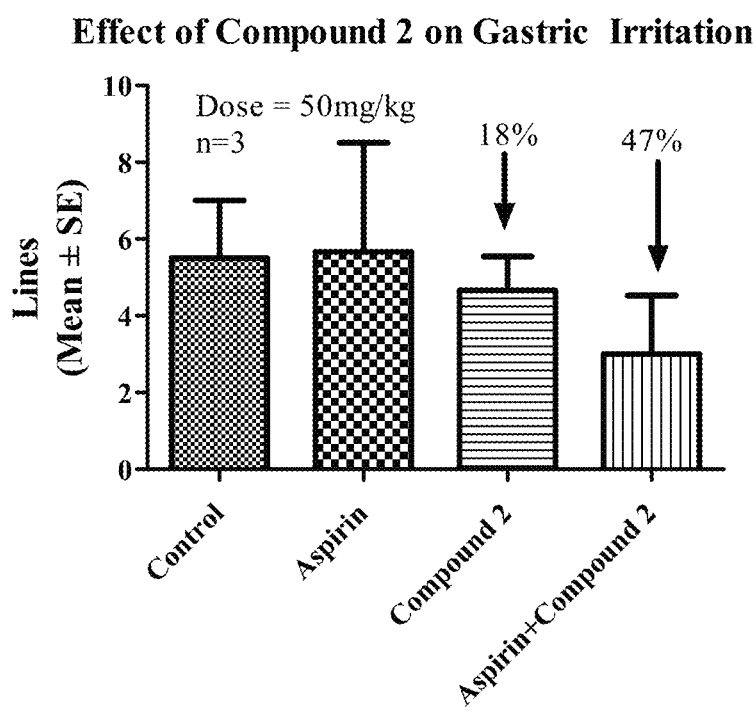
FIG. 6 Compound 2, when administered at dose of 50 mg/kg p.o., has shown demonstrable effect in gastric irritation model. From the quantitative data on the lines and lesions it is observed that the lines produced are reduced by 47% when Compound 2 is given along with Aspirin.
Figure 7A:
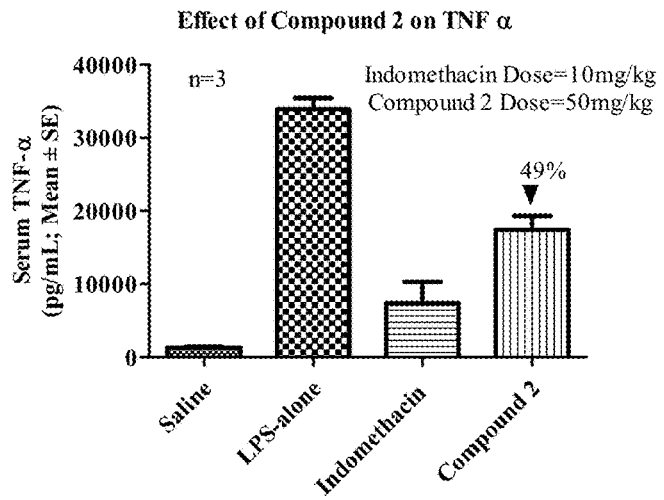
FIG. 7 shows that mice administered with Compound 2 showed a 49% decrease of TNF-α(FIG. 7A), 62% decrease of IL-6 (FIG. 7B) and 51% decrease of IL-1B (FIG. 7C) from the LPS group.
Figure 7B:
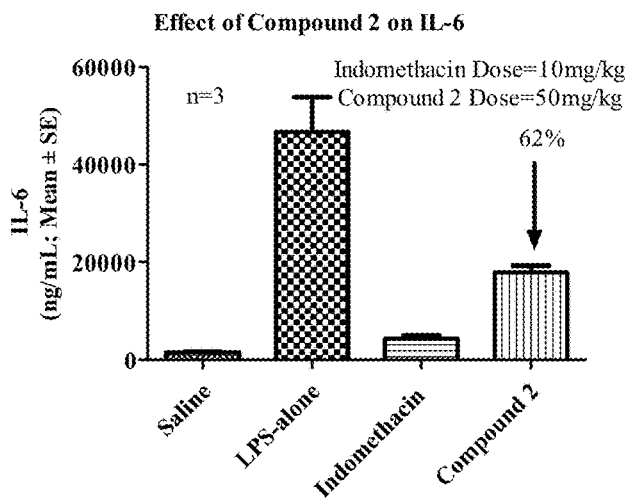
Figure 7C:
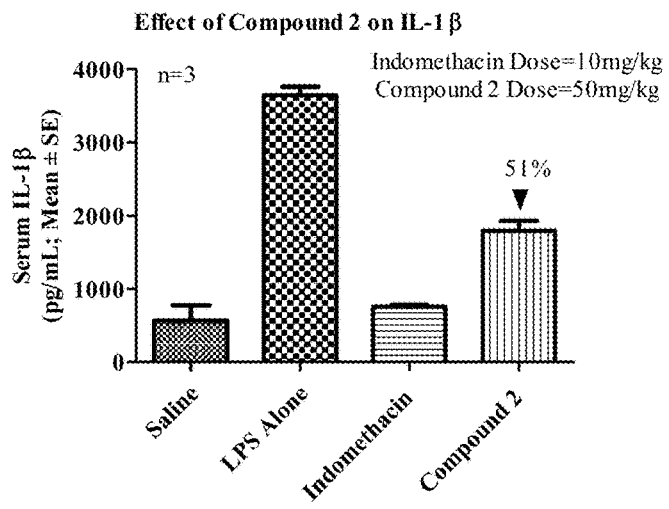
Figure 8:
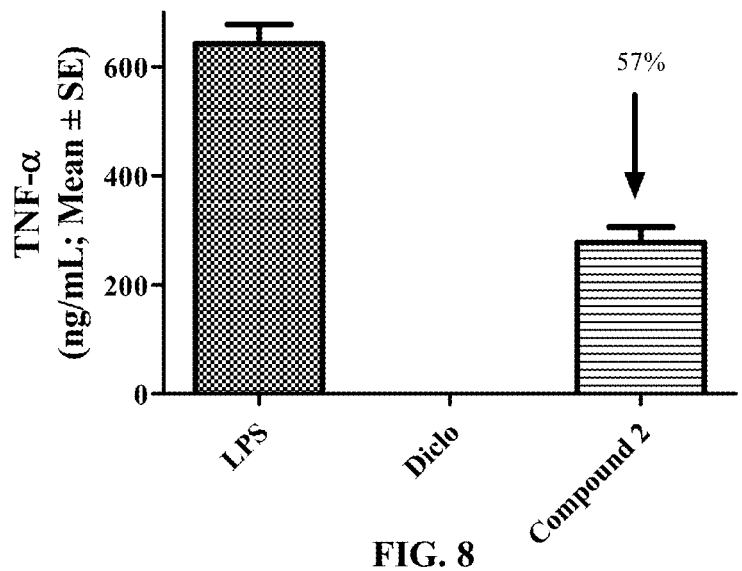
FIG. 8 shows that mice administered with Compound 2 showed a 57% decrease of TNF-α from the LPS group.
Figure 9:
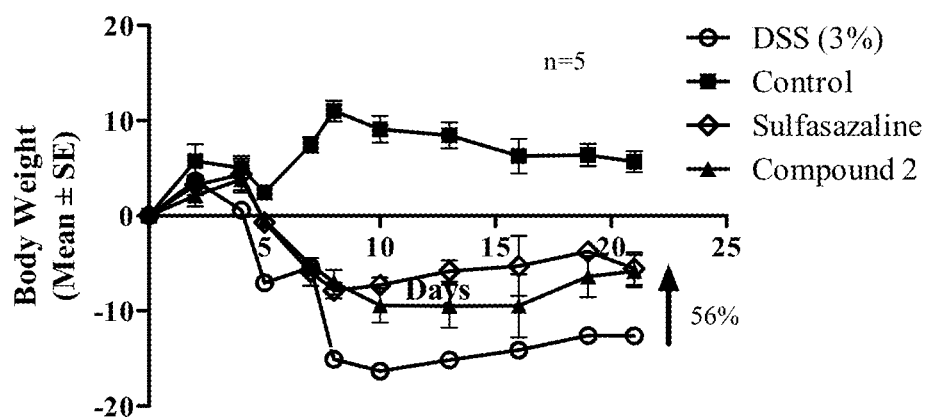
FIG. 9 shows that at the end of the study period of 21 days, the group of mice administered with compound 2 showed a significant (P<0.02) increase by 56% in body weight, compared with the vehicle DSS group.
Figure 10:
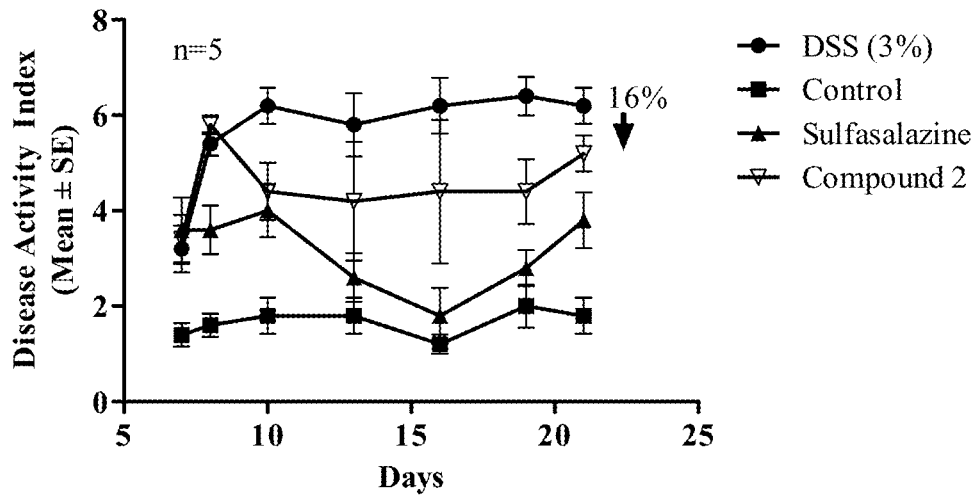
FIG. 10 shows at the end of the study period of 21 days, the group of mice administered with Compound 2 showed a significant (P<0.02) decrease by 16% in Disease Activity Index, compared with the vehicle DSS group.
Figure 11:
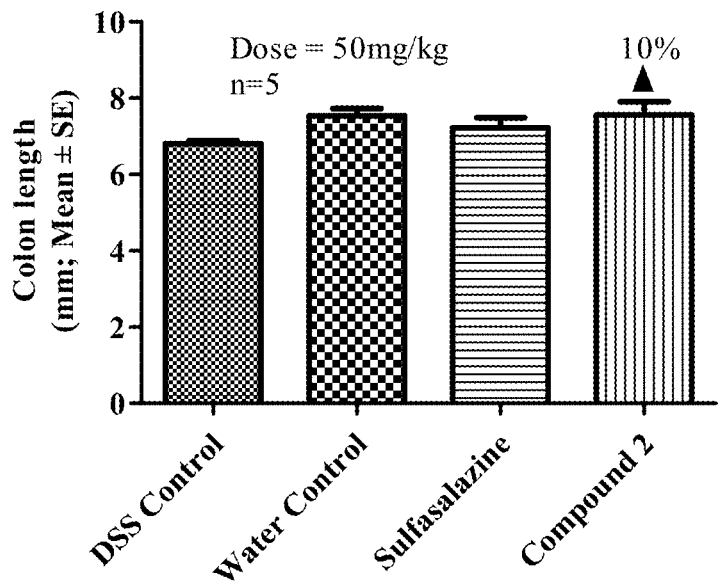
FIG. 11 shows that at the end of the study period of 21 days, the group of mice administered with Compound 2 showed a 10% increase in colon length, compared with the vehicle DSS group.
Figure 12:
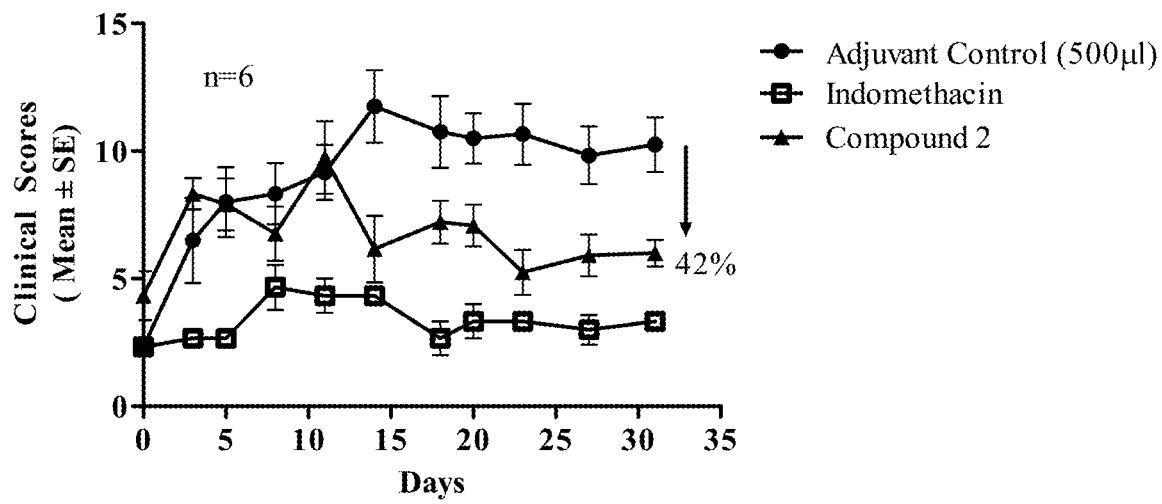
FIG. 12 shows that at the end of the study period of 30 days, the group of rats administered with Compound 2 showed a significant (P<0.02) decrease by 42%, from the vehicle control group in clinical scores
Figure 13:
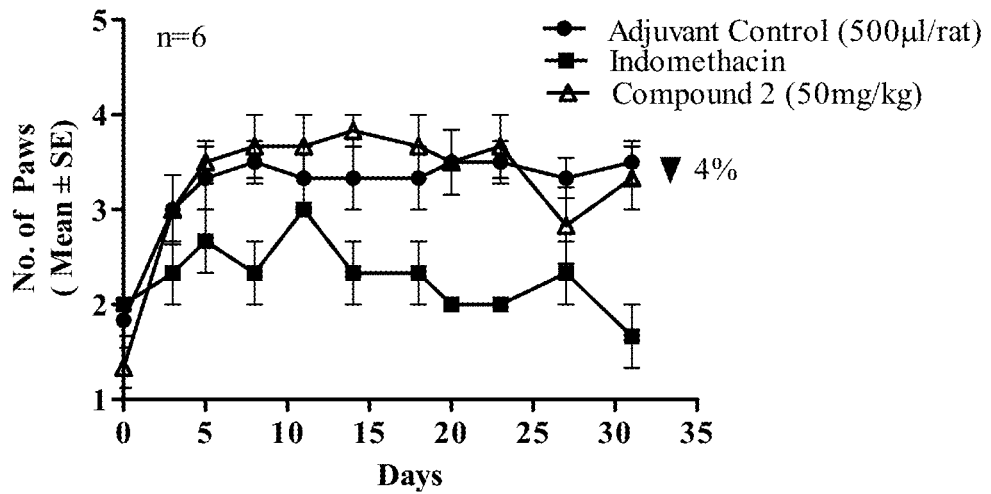
FIG. 13 shows that at the end of the study period of 30 days, the group of rats administered with Compound 2 showed a decrease by 4% in their number of limbs showing arthritic symptoms, from the vehicle control group.
Figure 14:
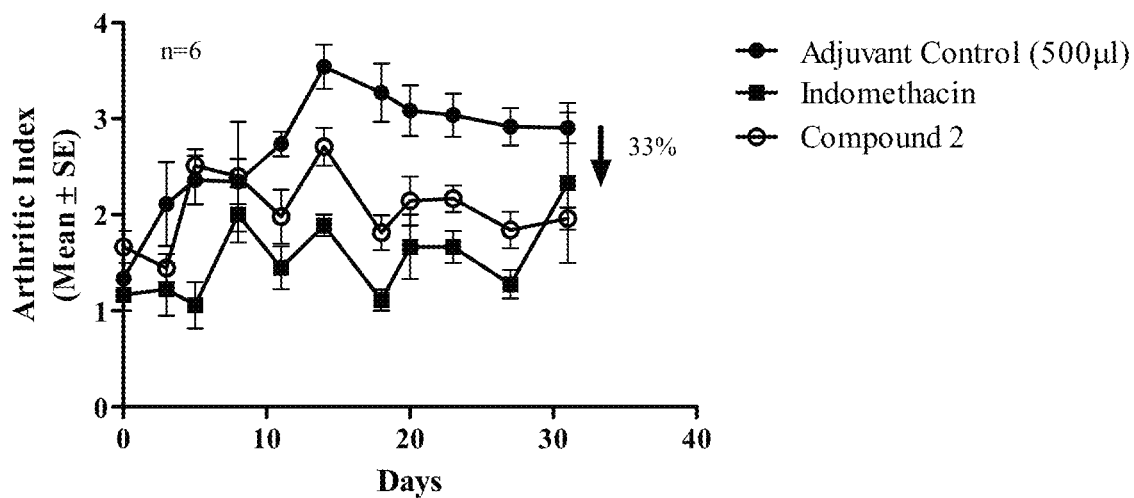
FIG. 14 shows that at the end of the study period of 30 days, the group of rats administered with Compound 2 showed a significant (P<0.009) decrease by 33% in their Arthritic Index, from the vehicle control group.
Figure 15:
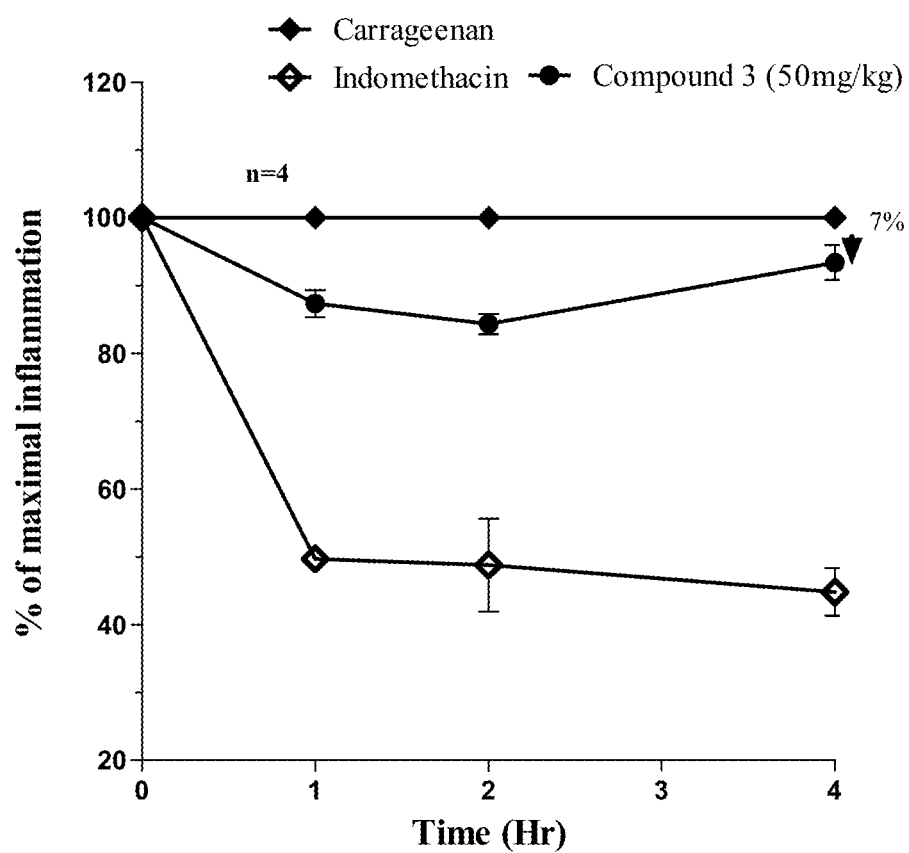
FIG. 15 shows that the group of rats administered with Compound 3 showed a 7% decrease in right hind leg volume.
Figure 16A:
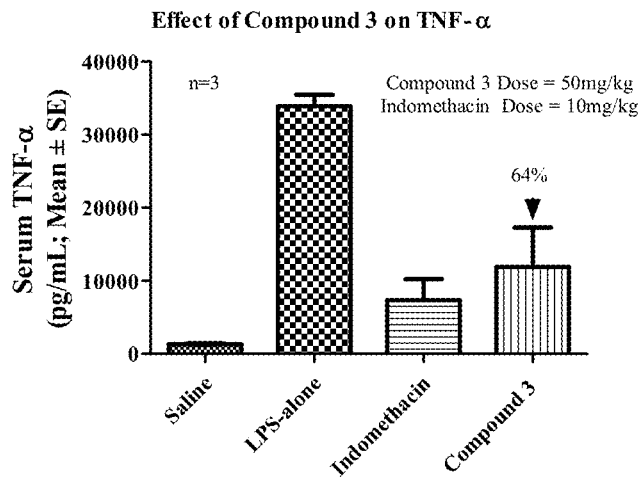
FIG. 16 shows mice administered with Compound 3 showed a 64% decrease in TNF-α(FIG. 16A), 63% decrease in IL-6 (FIG. 16B), and 58% decrease in IL-1B (FIG. 16C) from the LPS group.
Figure 16B:
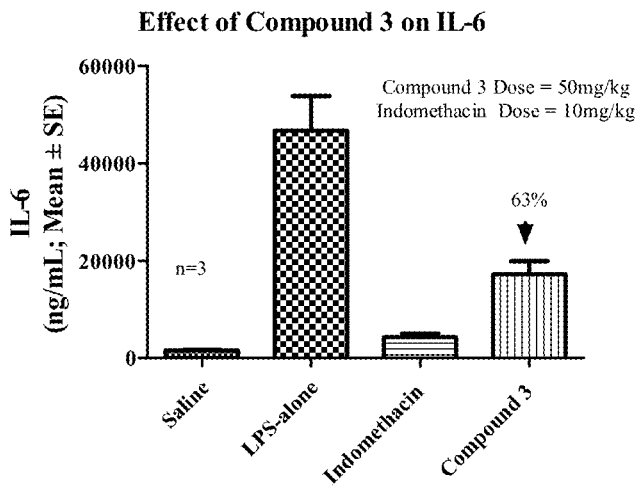
Figure 16C:
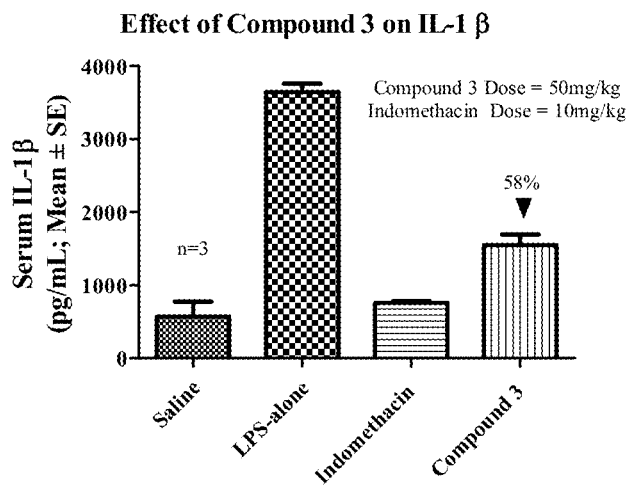
Figure 17:
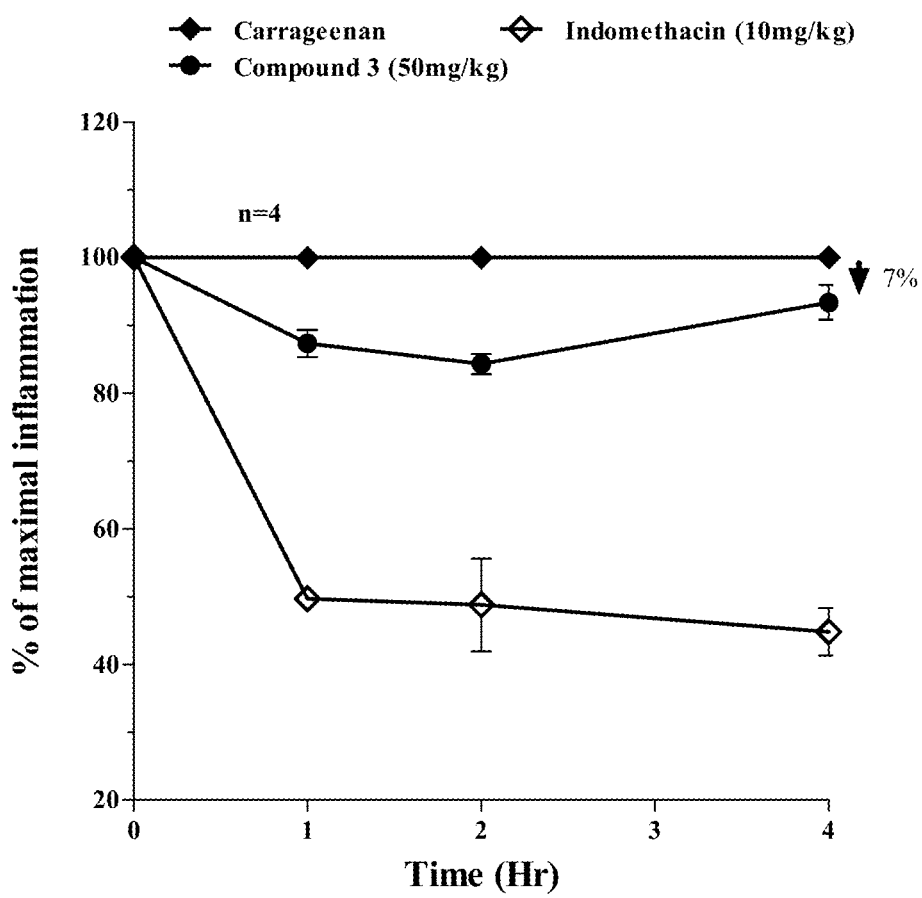
FIG. 17 shows that rats administered with Compound 4 showed a 7% decrease in right hind leg volume.
Figure 18A:
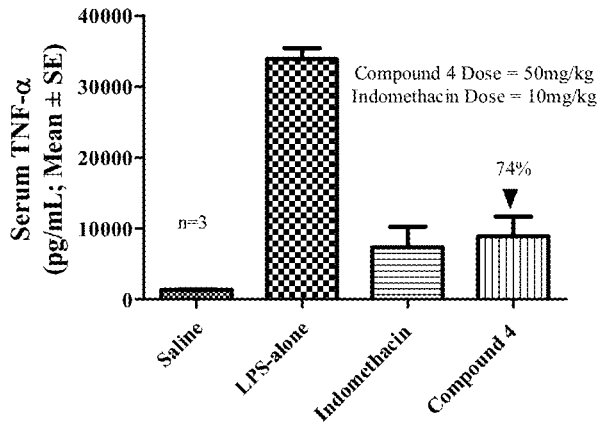
FIG. 18 shows that mice administered with Compound 4 showed a 74% decrease in TNF-α (FIG. 18A), 62% decrease in IL-6 (FIG. 18B), and 80% decrease in IL-1B (FIG. 18C) from the LPS group.
Figure 18B:
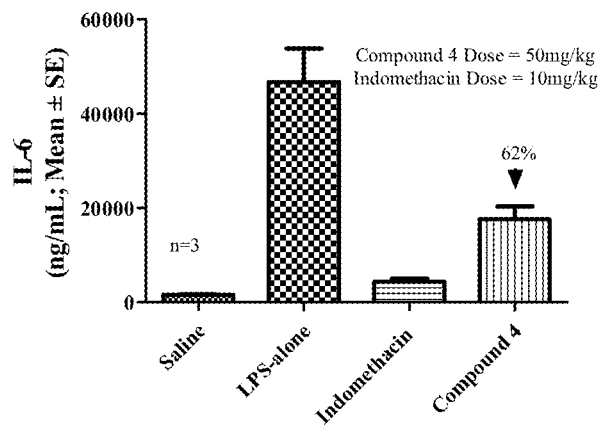
Figure 18C:
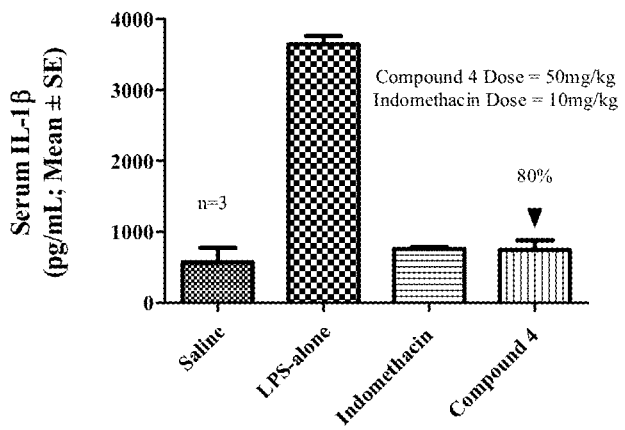
Figure 19A:
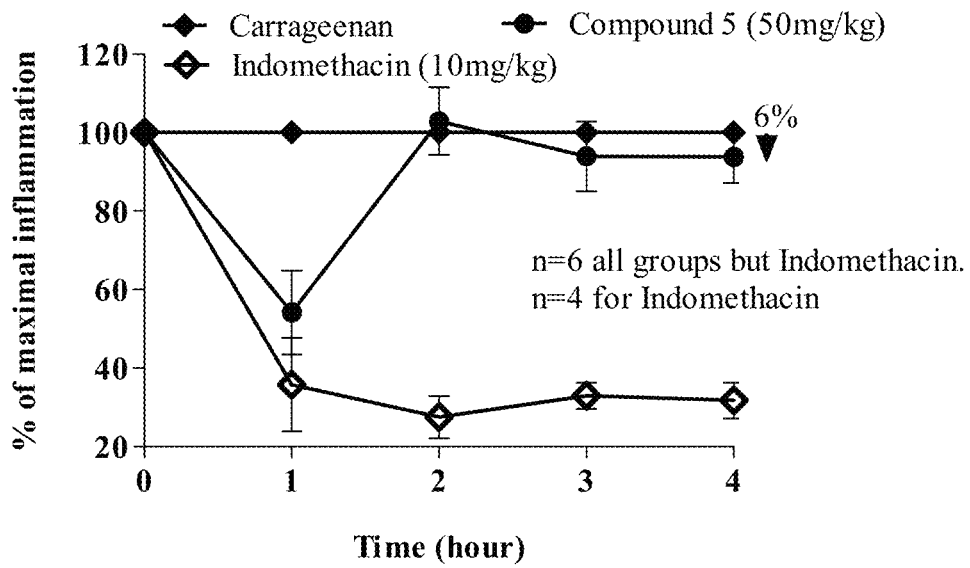
FIG. 19 shows that the group of rats administered with Compound 5 showed a 6% decrease in right hind leg volume (FIG. 19A). The group of rats administered with Compound 5 showed a 6% decrease in right hind leg thickness (FIG. 19B).
Figure 19B:
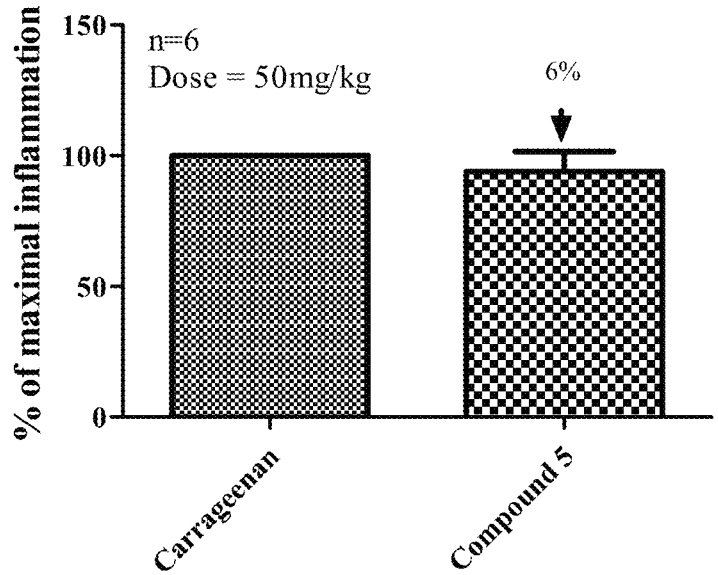
Figure 20A:
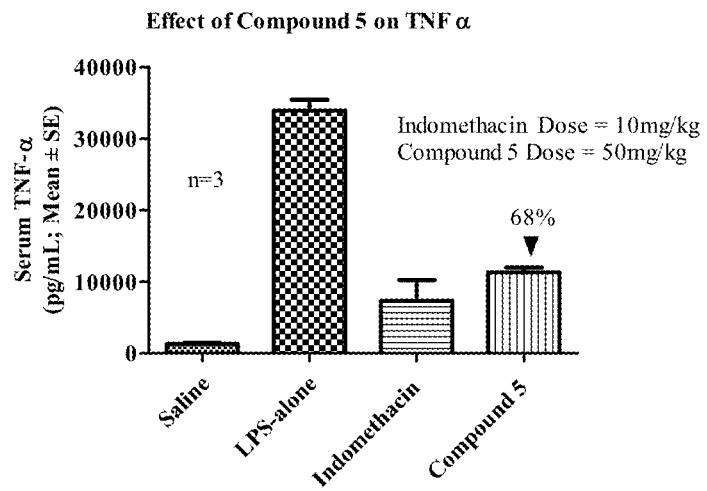
FIG. 20 shows that the group of mice administered with Compound 5 showed a 68% decrease in TNF-α(FIG. 20A), 85% decrease in IL-6 (FIG. 20B), and 82% decrease in IL-1B (FIG. 20C) from the LPS group.
Figure 20B:
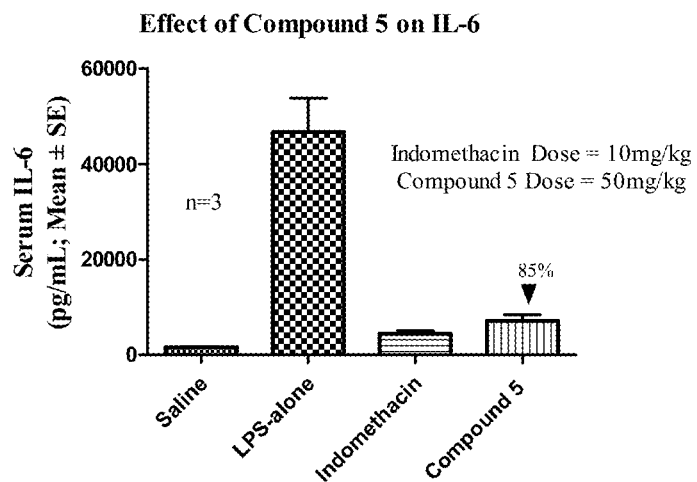
Figure 20C:
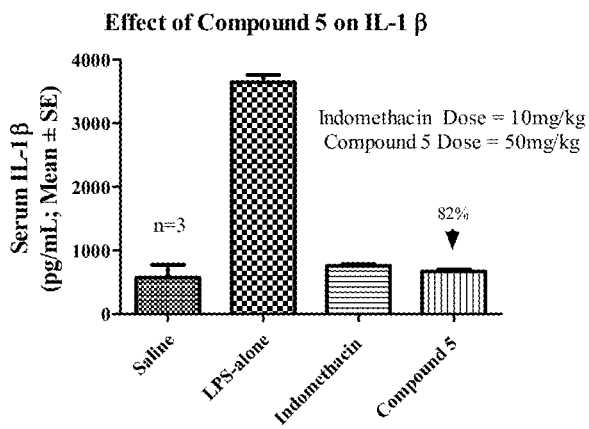
Figure 21A:
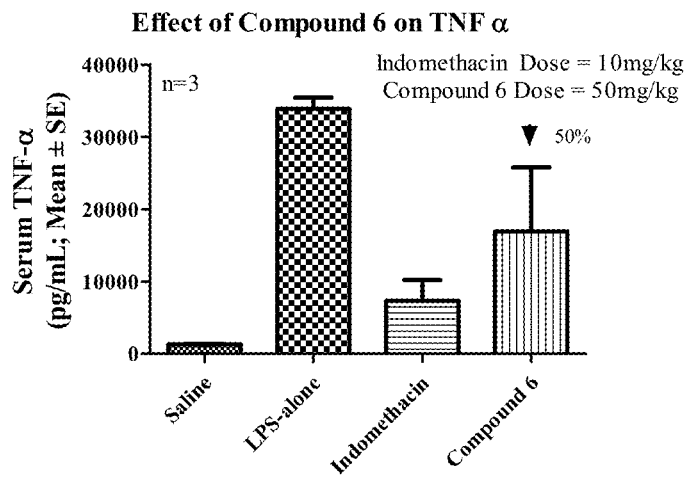
FIG. 21 The group of mice administered with Compound 6 showed a 50% decrease in TNF-α (FIG. 21A), 74% decrease in IL-6 (FIG. 21B), and 77% decrease in IL-1B (FIG. 21C) from the LPS group.
Figure 21B:
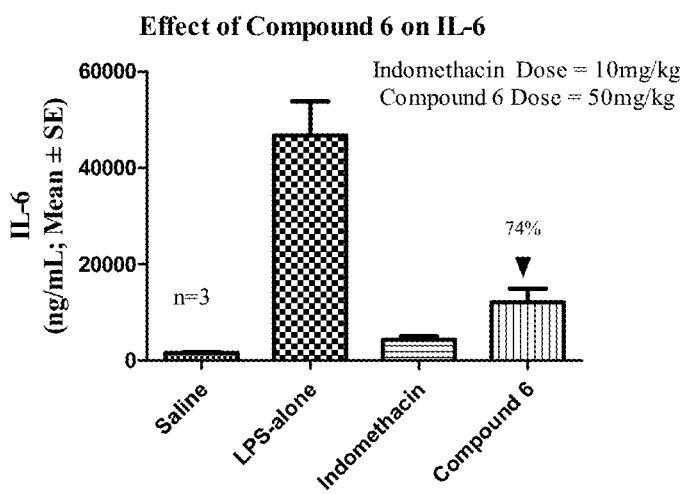
Figure 21C:
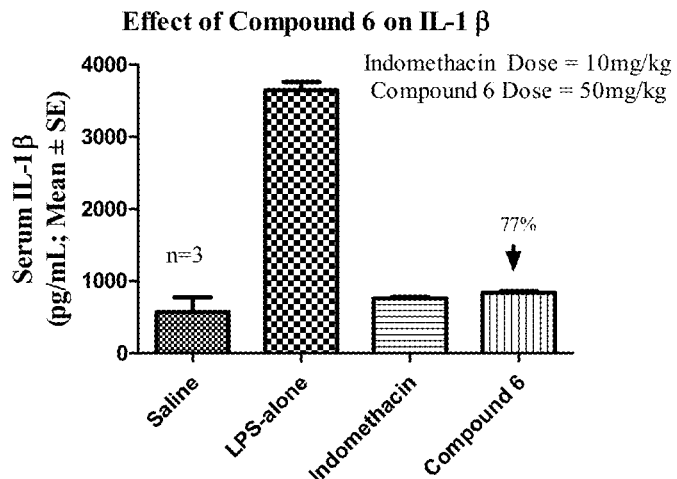
Figure 22A:
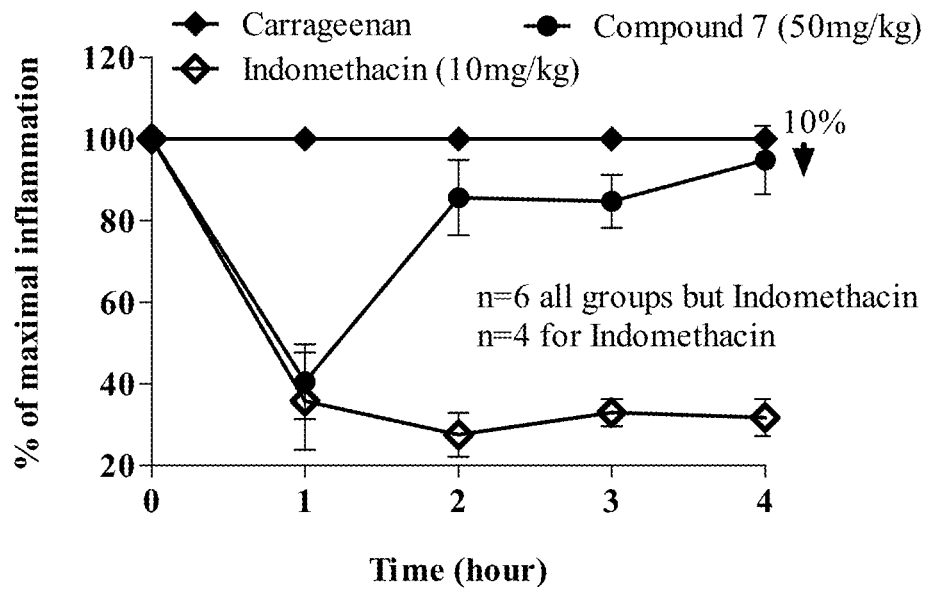
FIG. 22 shows that rats administered with Compound 7 showed a 10% decrease in right hind leg volume (FIG. 22A). The group of rats administered with Compound 7 showed a 8% decrease in right hind leg thickness (FIG. 22B).
Figure 22B:
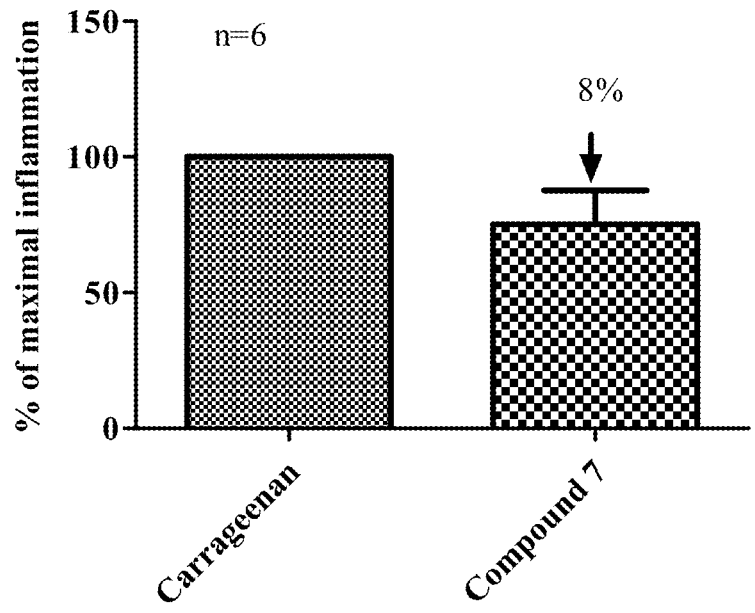
Figure 23A:
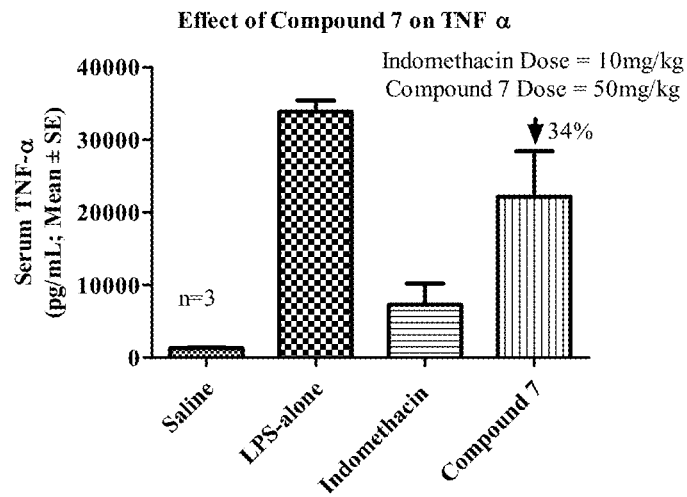
FIG. 23 shows that mice administered with Compound 7 showed a 34% decrease in TNF-α (FIG. 23A), 80% decrease in IL-6 (FIG. 23B), and 68% decrease in IL-1B (FIG. 23C) from the LPS group.
Figure 23B:
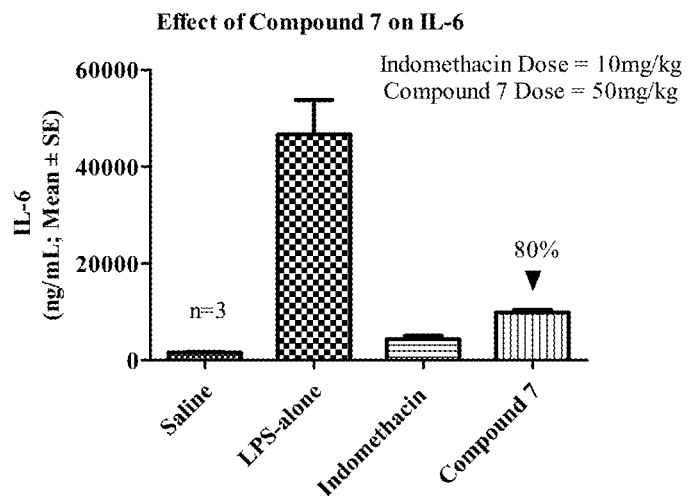
Figure 23C:
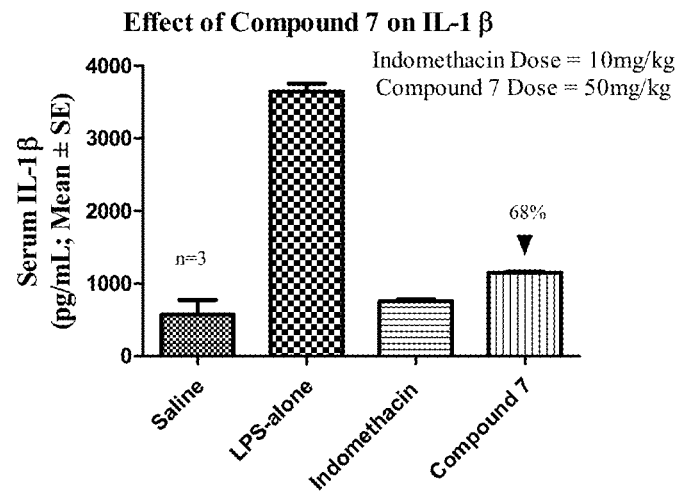
Figure 24:
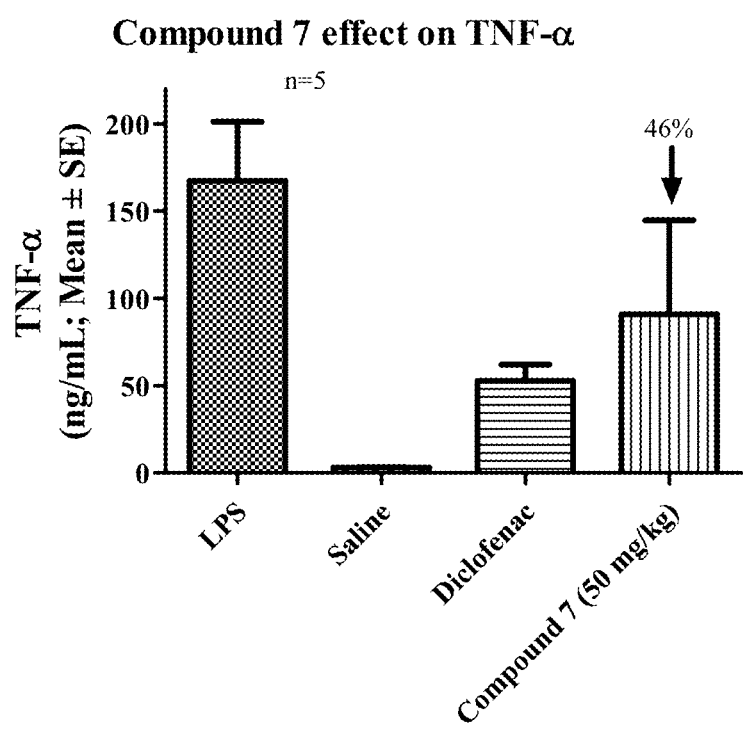
FIG. 24 shows that mice administered with Compound 7 showed a 46% decrease in TNF-α from the LPS group.
Figure 25:
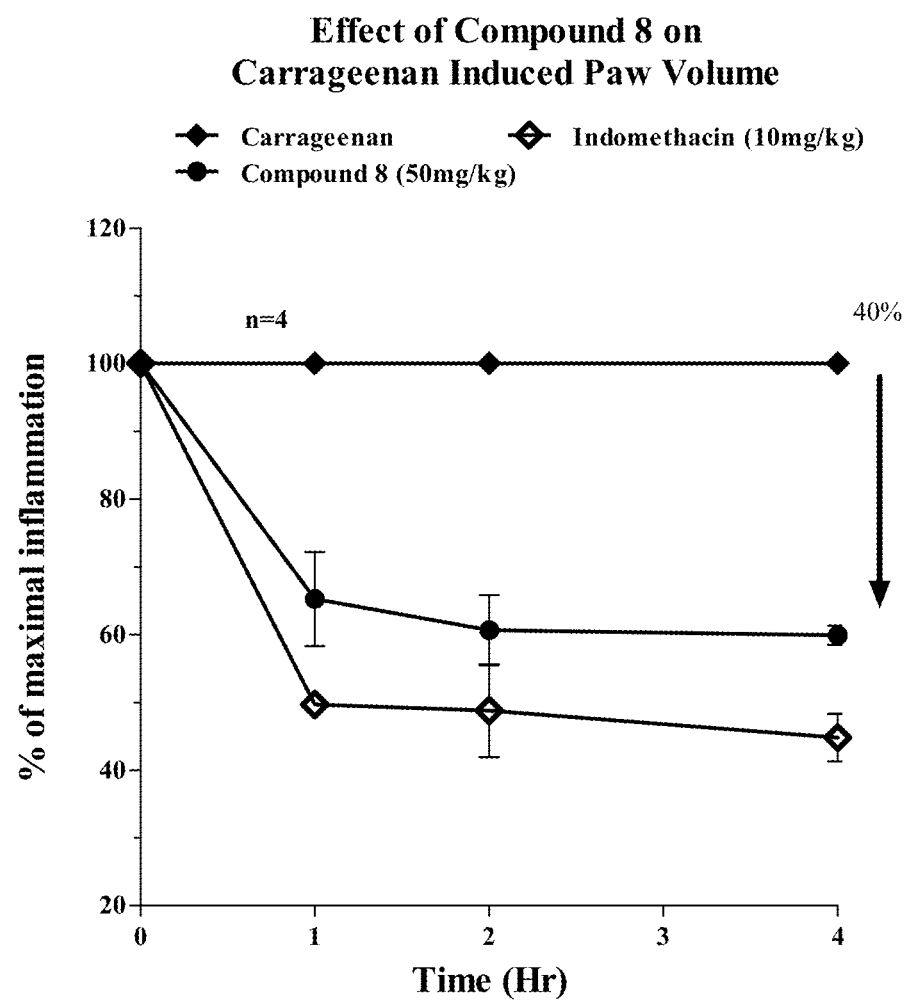
FIG. 25 shows that the group of rats administered with Compound 8 showed a 40% decrease in right hind leg volume.
Figure 26A:
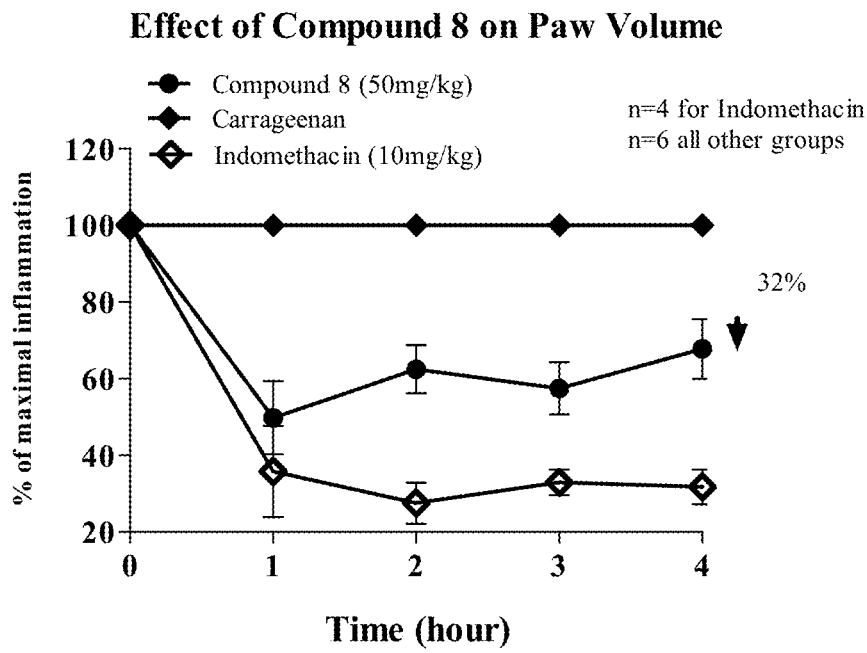
FIG. 26 shows that the group of rats administered with Compound 8 showed a 32% decrease in right hind leg volume (FIG. 26A). The group of rats administered with Compound 8 showed a 31% decrease in right hind leg thickness (FIG. 26B).
Figure 26B:
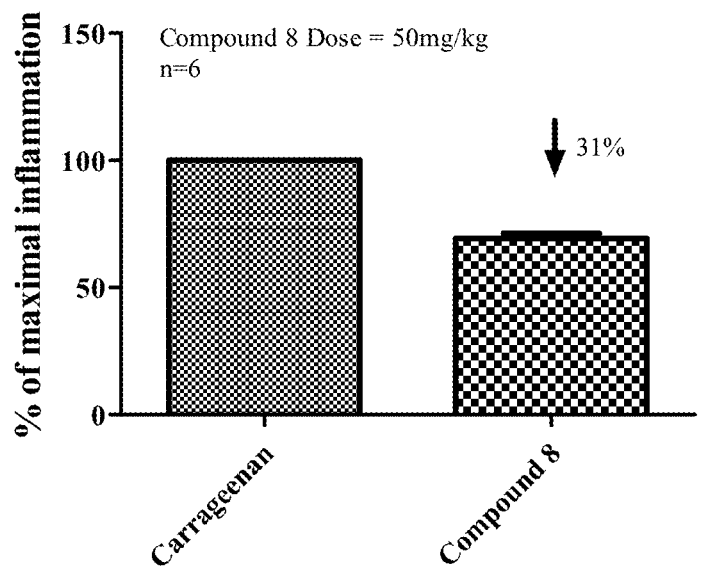
Figure 27A:
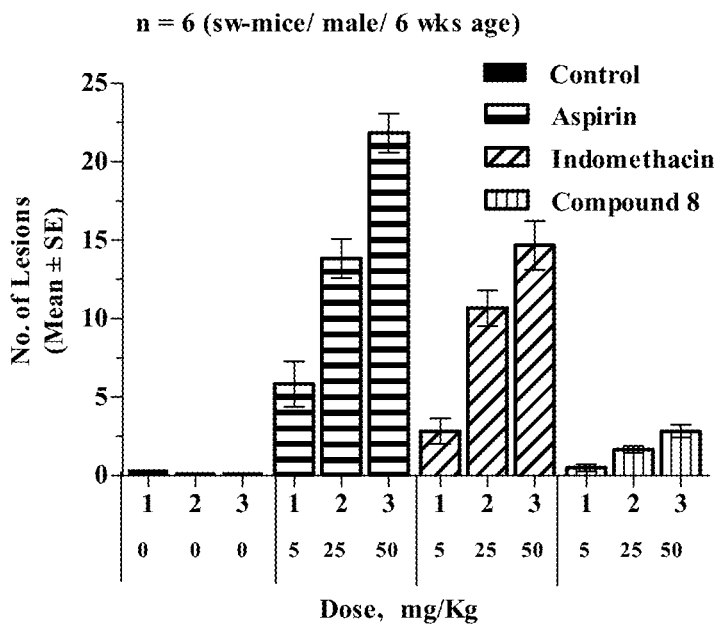
FIG. 27 shows that a dose dependent increase in the number of injured hemorrhagic lines (range 6-32) and lesions (range 6-22) were observed in the group of mice administered with Aspirin. A similar dose dependent increase in the number of injured hemorrhagic lines (range 2-20) and lesions (range 3-15) were observed in the group of mice administered with Indomethacin. In the group of mice administered with Compound 8, fewer injured hemorrhagic lines (range <1 to 2) and lesions (range <1 to 3) were observed.
Figure 27B:
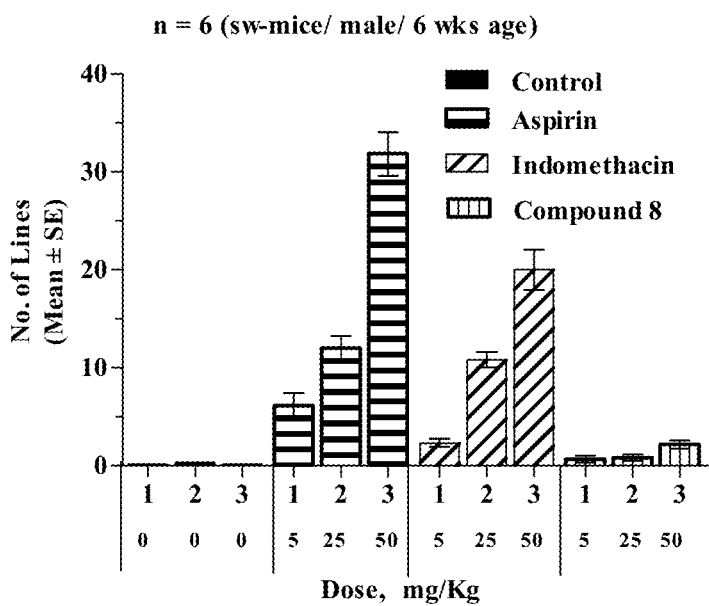
Figure 28A:
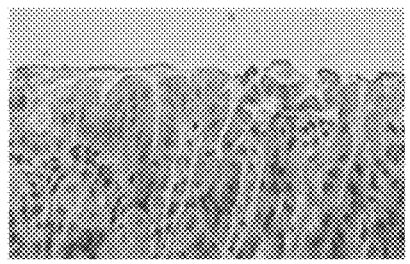
FIG. 28 shows that the stomach from the Control group of mice did not show any hemorrhagic lines or lesions (FIG. 28A). The stomachs from the Aspirin (FIG. 28B) and Indomethacin (FIG. 28C) groups of mice showed hemorrhagic lines and lesions. The stomach from the group of mice administered with Compound 8 did not show any hemorrhagic lines or lesions (FIG. 28D).
Figure 28B:
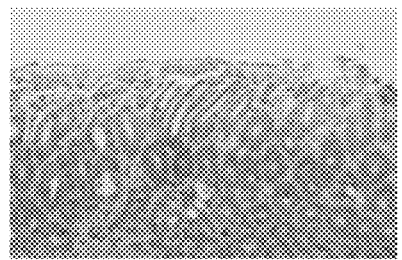
Figure 28C:
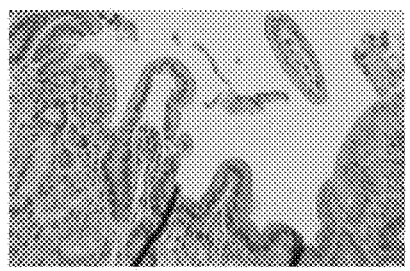
Figure 28D:
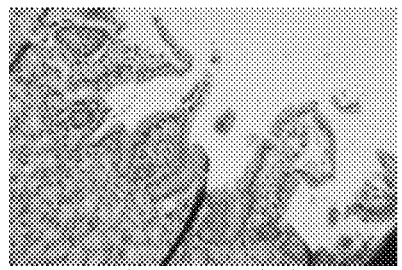
Figure 29A:
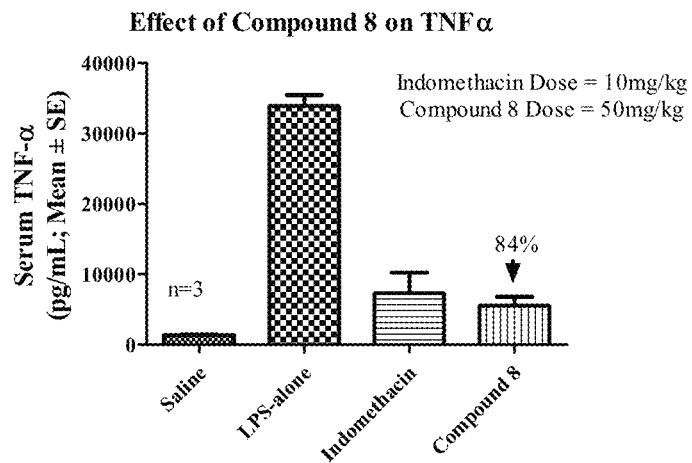
FIG. 29 shows that the group of mice administered with Compound 8 showed an 84% decrease in TNF-α(FIG. 29A), 90% decrease in IL-6 (FIG. 29B), and 94% decrease in IL-1B (FIG. 29C) from the LPS group.
Figure 29B:
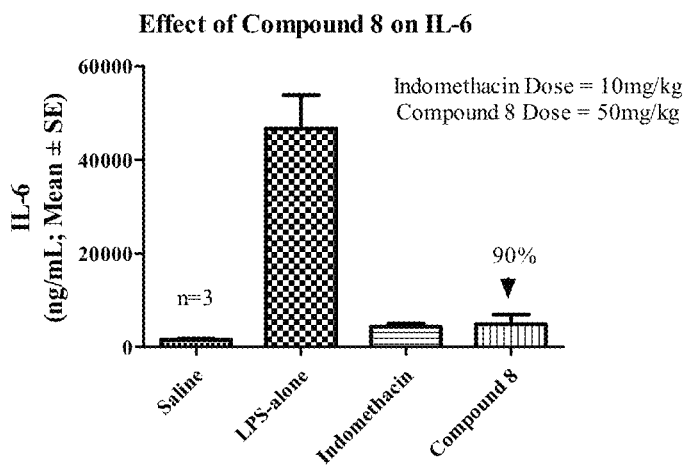
Figure 29C:
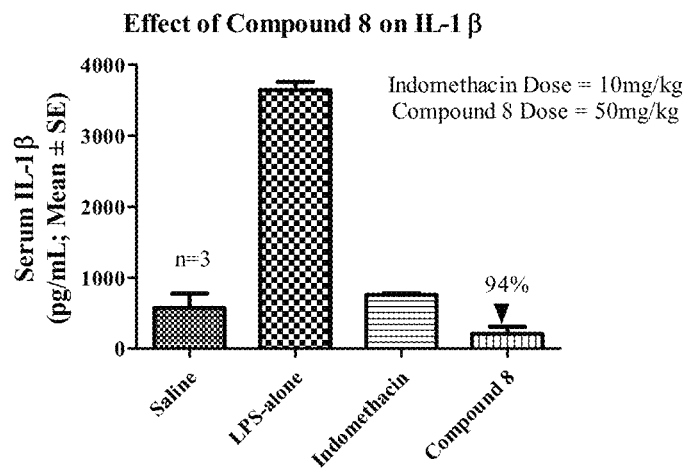
Figure 30:
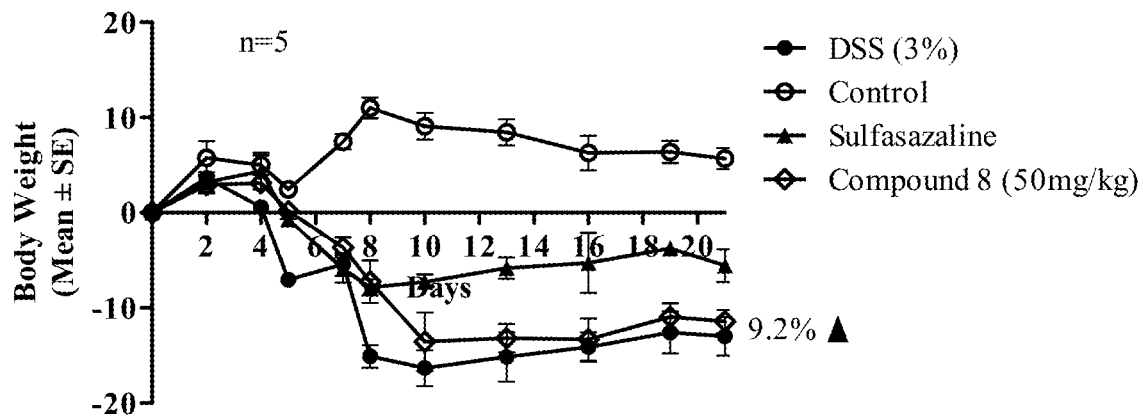
FIG. 30 shows that at the end of the study period of 21 days, the group of mice administered with Compound 8 showed an increase by 9% in body weight, compared with the vehicle DSS group.
Figure 31:
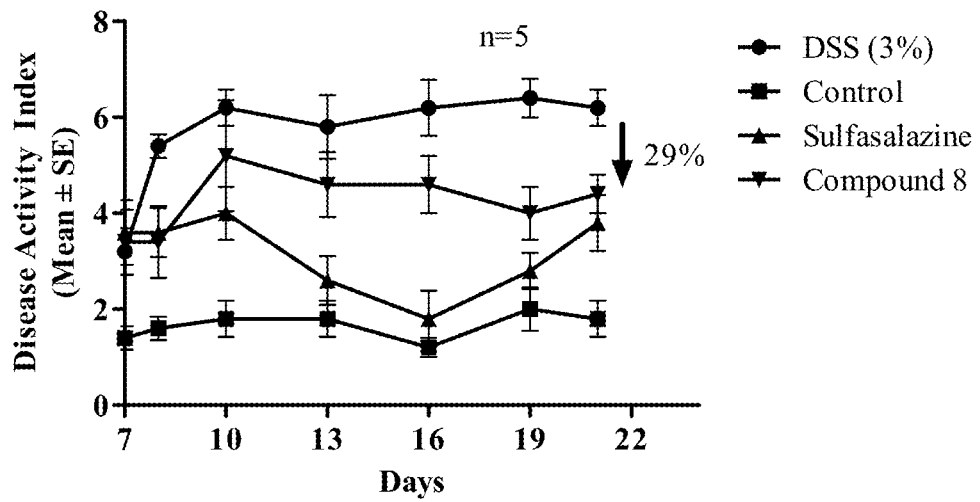
FIG. 31 shows that at the end of the study period of 21 days, the group of mice administered with Compound 8 showed a significant (P<0.02) decrease by 29% in Disease Activity Index, compared with the vehicle DSS group.
Figure 32:
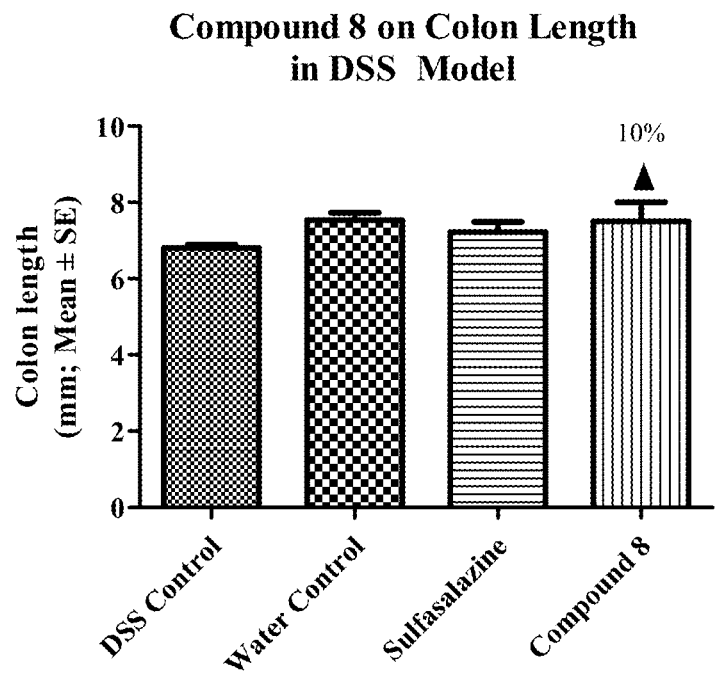
FIG. 32 shows that at the end of the study period of 21 days, the group of mice administered with Compound 8 showed a 10% increase in colon length, compared with the vehicle DSS group.
Figure 33:
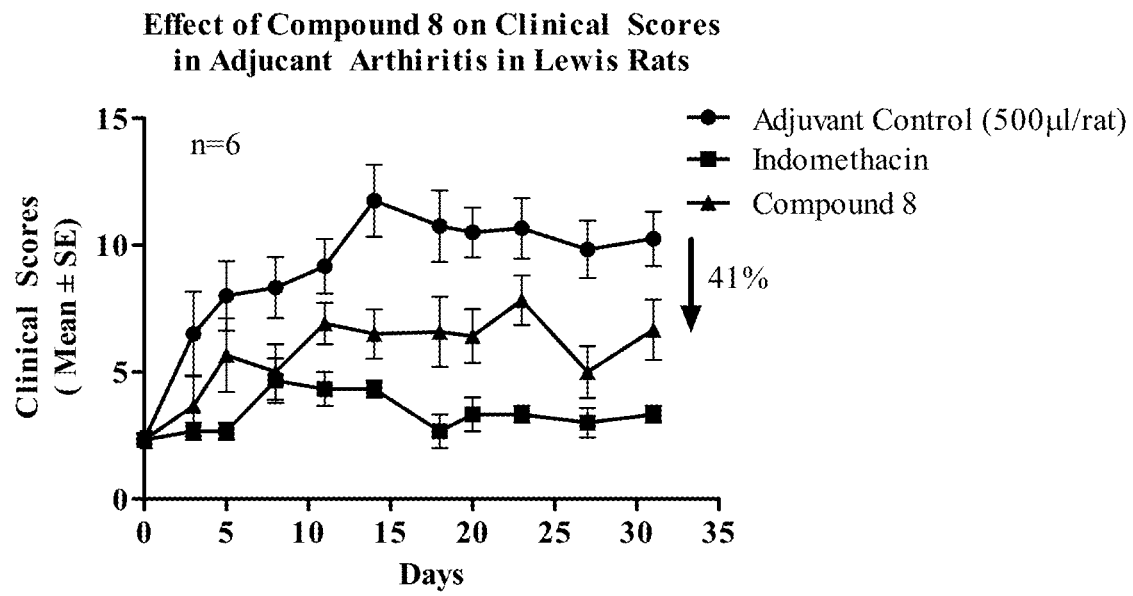
FIG. 33 shows that at the end of the study period of 30 days, the group of rats administered with Compound 8 showed a significant (P<0.02) decrease by 41%, from the vehicle control group in clinical scores
Figure 34:
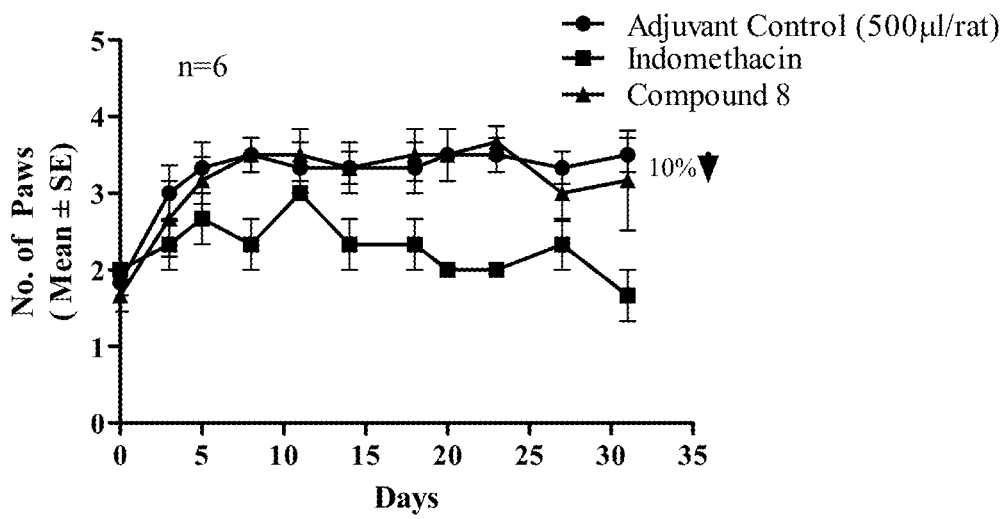
FIG. 34 shows that at the end of the study period of 30 days, the group of rats administered with Compound 8 showed a decrease by 10% in their number of limbs showing arthritic symptoms, from the vehicle control group.
Figure 35:
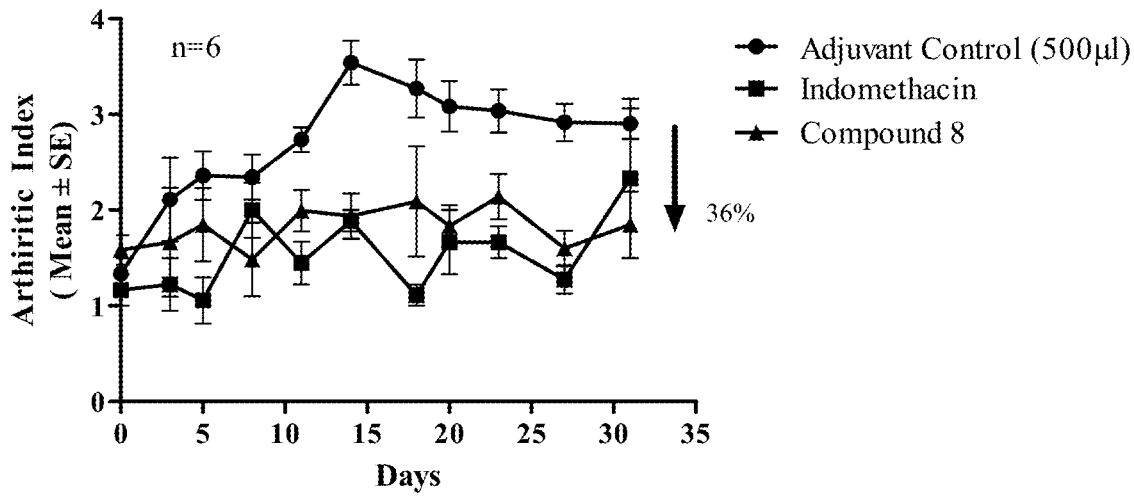
FIG. 35 shows that at the end of the study period of 30 days, the group of rats administered with Compound 8 showed a significant (P<0.0003) decrease by 36% in their Arthritic Index, from the vehicle control group.
Figure 36:
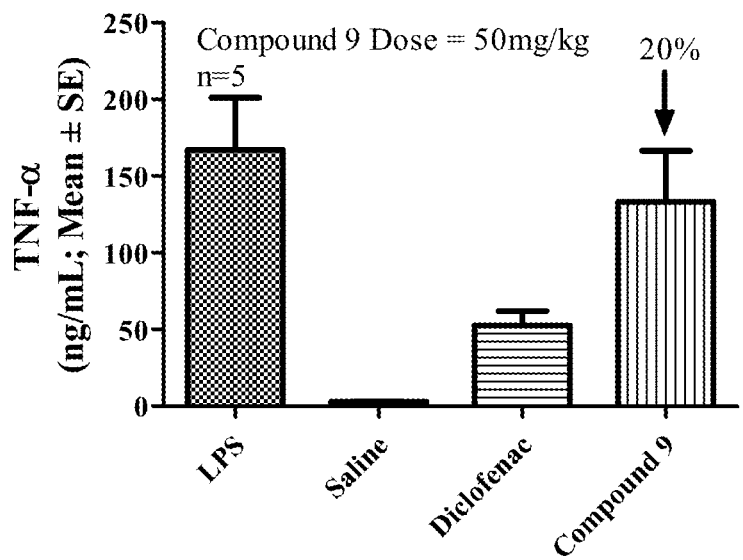
FIG. 36 shows that mice administered with Compound 9 showed a 20% decrease in TNF-α from the LPS group.
Figure 37:
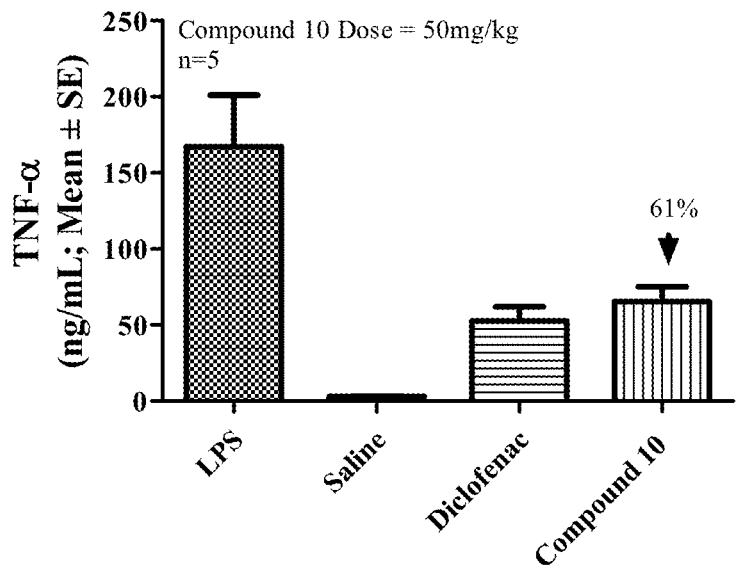
FIG. 37 shows that mice administered with Compound 10 showed a 61% decrease in TNF-α from the LPS group.
Figure 38:
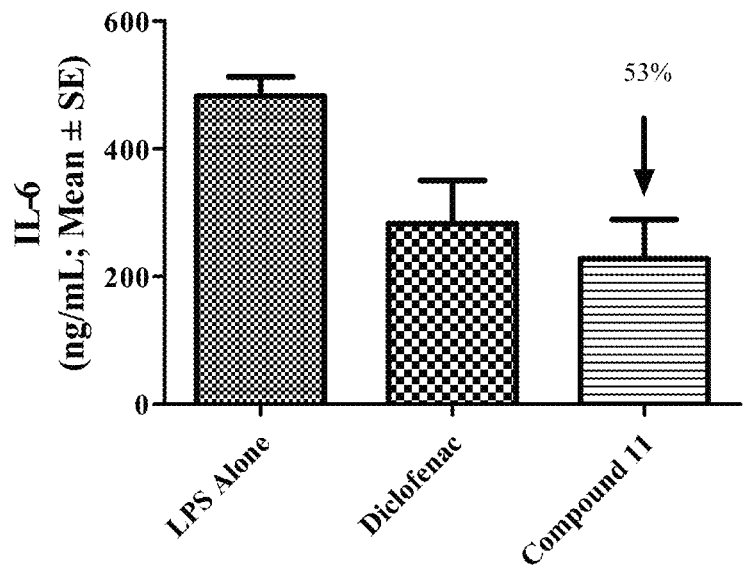
FIG. 38 shows that mice administered with Compound 10 showed a 53% decrease in IL-6 from the LPS group.
Figure 39:
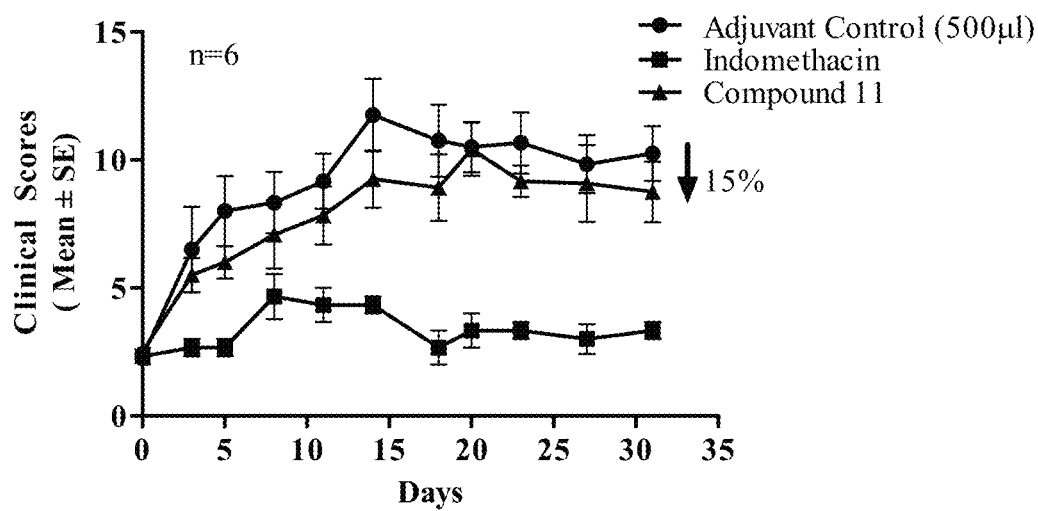
FIG. 39 shows that at the end of the study period of 30 days, the group of rats administered with Compound 11 showed a significant (P<0.02) decrease by 15%, from the vehicle control group in clinical scores
Figure 40:
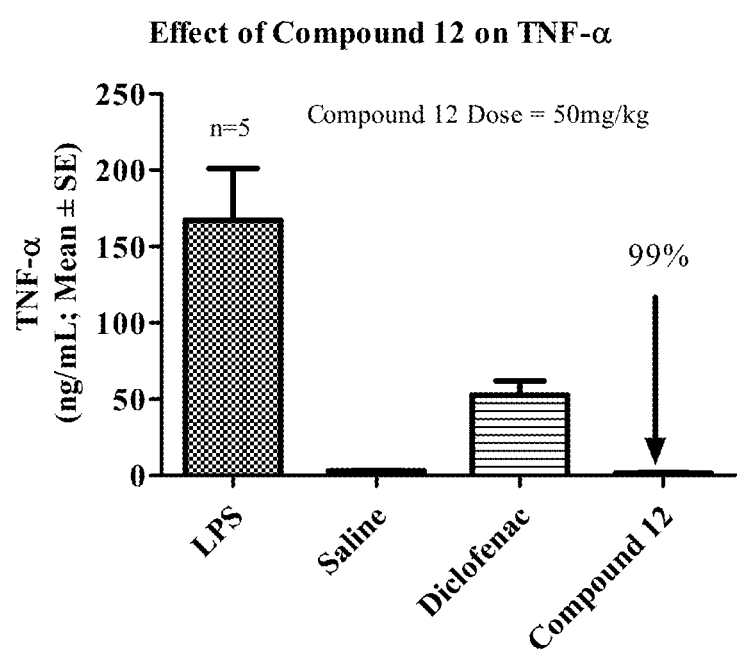
FIG. 40 shows that the group of mice administered with Compound 12 showed a significant decrease (P<0.0001) by 99% of TNF-α from the Control LPS group.
Figure 41A:
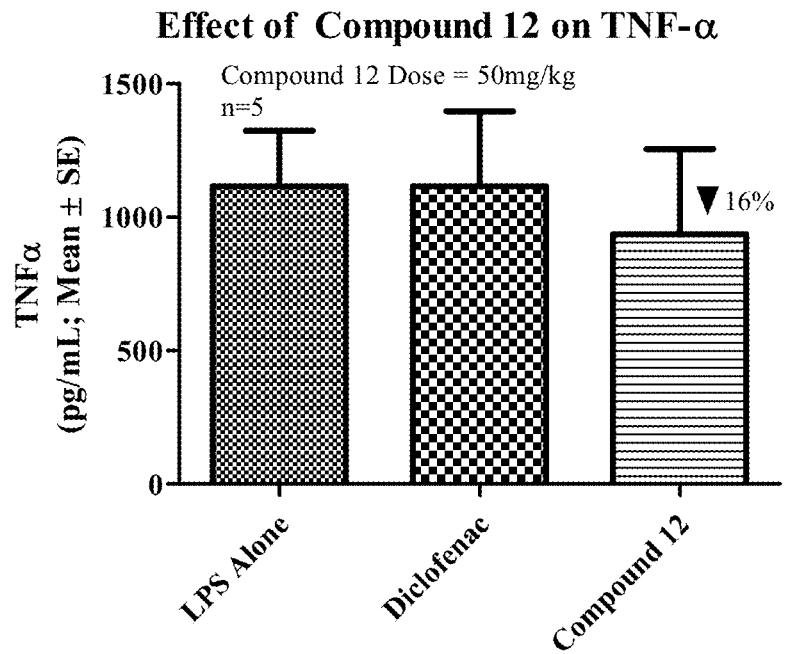
FIG. 41 shows that mice administered with Compound 12 showed a decrease by 16% of TNF-α(FIG. 41A) and a significant decrease (P<0.015) by 60% of IL-6 (FIG. 41B), compared from the control LPS group.
Figure 41B:
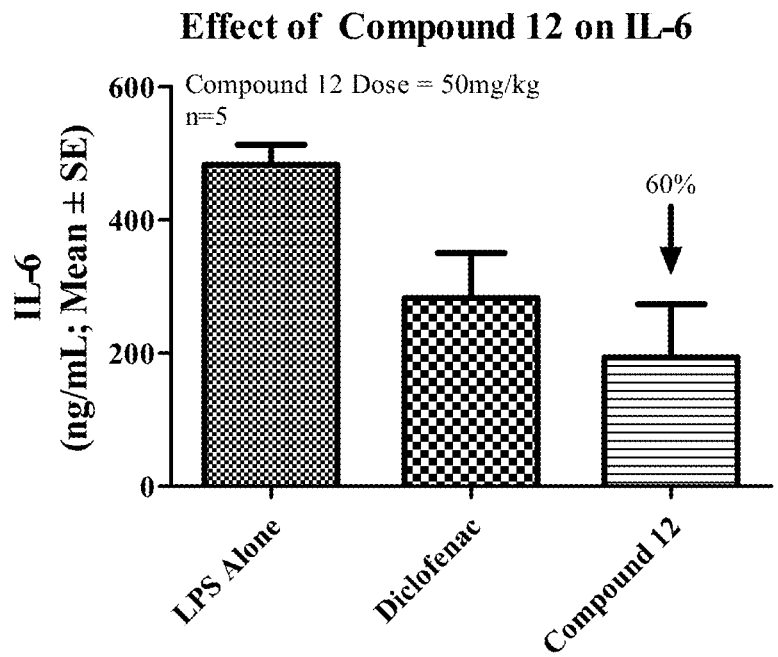
Figure 42:
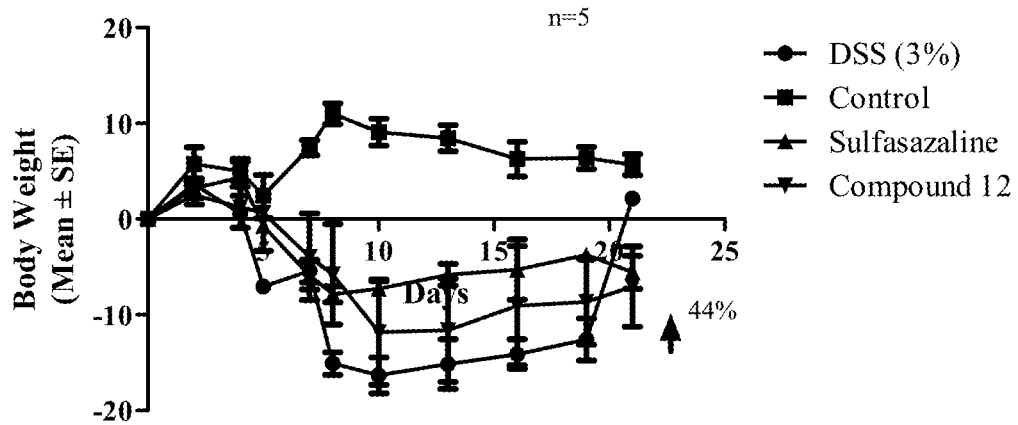
FIG. 42 shows that at the end of the study period of 21 days, the group of mice administered with Compound 12 showed an increase by 44% in body weight, compared with the vehicle DSS group.
Figure 43:
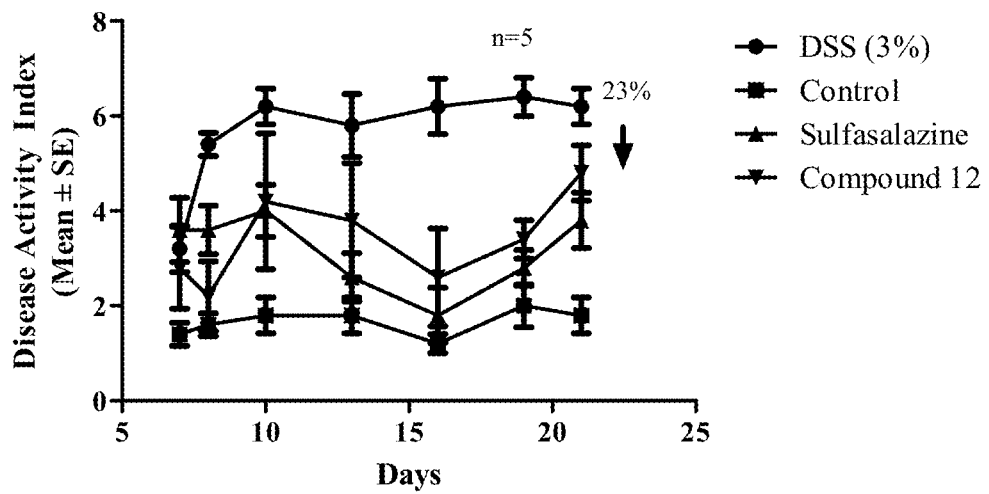
FIG. 43 shows that at the end of the study period of 21 days, the group of mice administered with Compound 12 showed a significant (P<0.002) decrease by 23% in Disease Activity Index, compared with the vehicle DSS group.
Figure 44:
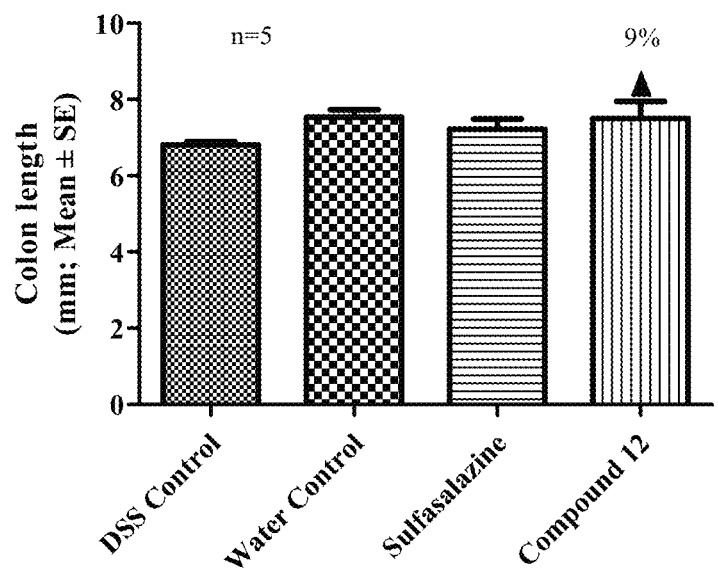
FIG. 44 shows that at the end of the study period of 21 days, the group of mice administered with Compound 12 showed a 9% increase in colon length, compared with the vehicle DSS group.
Figure 45:
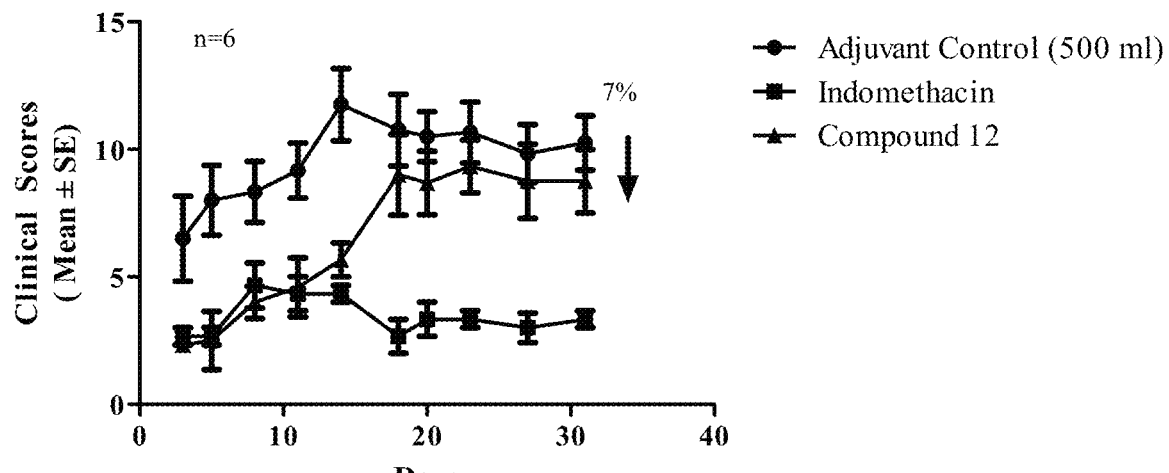
FIG. 45 shows that at the end of the study period of 30 days, the group of rats administered with Compound 12 showed a decrease by 7%, from the vehicle control group in the clinical scores.

In an embodiment of the present invention, the amino acid group represented by $R_4$ is selected from alaninie, glycine, arginine, aspargine, cysteine, glutamic acid, glutamine, histidine, isoleucine, leucine, lysine, methionine, ornithine, proline, serine, threonine, tryptophan, tyrosine and the like, which may be unsubstituted or substituted and their derivatives such as ester and amides of carboxylic acid. The preferred substituents are selected from halogen, alkyl, alkoxy, aryl, heteroaryl, amino and the like. $R_4$ always condenses through the free amino group of the amino acid as represented by N—$R_4$ in FIG. 1.

In an embodiment of the present invention, the group $R_4$ is represented by unsubstituted or substituted aryl amines, pyridyl amine and amino benzoic acid wherein the free amine group condenses to form the Halogenated Benzylidene compound.

Pharmaceutically acceptable salts forming part of this invention include base addition salts such as alkali metal salts like Li, Na, and K salts, alkaline earth metal salts like Ca and Mg salts, salts of organic bases such as lysine, arginine, guanidine, diethanolamine, chlorine and the like, ammonium or substituted ammonium salts. Salts may include acid addition salts which are sulphates, nitrates, phosphates, perchlorates, borates, hydrohalides, acetates, tartarates, maleates, citrates, succinates, palmoates, methanesulphonates, benzoates, ascorbates, glycerophosphates, ketoglutarates and the like. Pharmaceutically acceptable solvates may be hydrates or comprising other solvents of crystallization such as alcohols.

More preferably, the present innovation relates to novel Halogenated Benzylidene derivatives of formula (I),

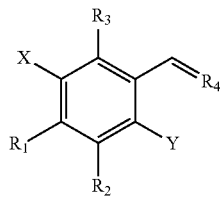

their derivatives, their analogs, their tautomeric forms, their stereoisomers, their polymorphs, their pharmaceutically acceptable salts, their pharmaceutically acceptable solvates, novel intermediates and pharmaceutical composites containing them, wherein, the group represented as X is always selected from halogens such as Fluorine, Chlorine, Bromine and Iodine, and Y is selected from hydrogen, halogen such as fluorine, chlorine, bromine or iodine; hydroxyl, nitro, cyano, formyl, amino or sulfonyl groups and the like, the groups represented by $R_1$ and $R_3$ are preferentially Hydrogen but can also be selected from linear or branched, substituted or unsubstituted ($C_1$ to $C_{12}$) alkyl groups such as methyl, ethyl, propyl, isopropyl, n-butyl, isobutyl, t-butyl, pentyl, hexyl, octyl, nonyl and the like; substituted or unsubstituted ($C_1$ to $C_{12}$) alkoxy group such as methoxy, ethoxy, propoxy, butoxy and the like; $R_2$ corresponds to a free hydroxyl group or extended chain through an alkyloxy ester or un-substituted or substituted aryloxy ester groups; and the amine group represented by $R_4$ is selected from amino acids such as alaninie, glycine, arginine, aspargine, cysteine, glutamic acid, glutamine, histidine, isoleucine, leucine, lysine, methionine, ornithine, proline, serine, threonine, tryptophan, tyrosine and the like, which may be substituted or unsubstituted and their derivatives such as ester and amides of carboxylic acid. The preferred substituents are selected from halogen, alkyl, alkoxy, aryl, heteroaryl, amino and the like and also $R_4$ corresponds to un-substituted or substituted aryl amines, pyridyl amine and amino benzoic acid wherein the free amine group condenses to form the Halogenated Benzylidene compounds. The double bond to $R_4$ can in some compounds be saturated and they are also included in the list of patented compounds.

The formula of the useful compounds synthesized in this present are listed below.

2-[(5-Bromo-2-hydroxy-benzylidene)-amino-3-(4-hydroxy phenyl)-propionic acid methyl ester (Compound 1)
2-[(5-Bromo-2-hydroxy-benzylidene)-amino-3-methyl butyric acid methyl ester (Compound 2)
2-(5-Bromo-2-hydroxy-benzylamino]-3-(4-hydroxy-phenyl)-propionic acid methyl ester (Compound 3)
2-[(5-Bromo-2-hydroxy-benzylidene)-amino-3-(4-hydroxy phenyl)-propionic acid
4-Bromo-2-{[2-hydroxy-1-(4-hydroxy benzyl)-ethylamino]-Methyl}-phenol (Compound 4)
2-(5-Bromo-2-hydroxy-benzylamino)-3-methyl-butyric acid methyl ester (Compound 5)
2-[(5-Bromo-2-hydroxy-benzylidene)-amino]-3-methyl-butyric acid (Compound 6)
4-Bromo-2-[(1-hydroxymethyl-2-methyl-propylimino)-methyl]-phenol (Compound 7)
(E)-4-bromo-2-((2,4-dichlorophenylimino)methyl) phenyl 4-methylbenzoate (Compound 8)
(E)-4-bromo-2-((4-chlorophenylimino)methyl)phenyl 4-methylbenzoate (Compound 9)
(E)-4-bromo-2-((2,3-dichlorophenylimino)methyl) phenyl 3-methylbenzoate (Compound 10)
(E)-4-bromo-2-((3,4-dichlorophenylimino)methyl) phenyl 4-methylbenzoate
(E)-4-bromo-2-((3,5-dichlorophenylimino)methyl) phenyl 4-methylbenzoate
(E)-4-bromo-2-((phenethylimino)methyl)phenyl 3-methylbenzoate
(E)-4-bromo-2-((phenethylimino)methyl)phenyl 4-methylbenzoate
(E)-4-bromo-2-((pyridin-3-ylimino)methyl)phenyl 4-methylbenzoate
(E)-4-bromo-2-((pyridin-3-ylimino)methyl)phenyl 3-methylbenzoate (Compound 11)
(E)-3-(5-bromo-2-(nicotinoyloxy)benzylideneamino) benzoic acid (Compound 12)
(E)-4-bromo-2-((phenethylimino)methyl)phenyl isobutyrate
2-[(5-Bromo-2-isobutyryloxy-benzylidene)-amino]-3-(4-isobutyryloxy phenyl propionic acid methyl ester
(E)-4-bromo-2-((4-((diethylamino)methyl)phenylimino) methyl)phenol
(E)-1-(3-chlorobenzylideneamino)-2-methylpropan-1-ol
(E)-1-(3-bromobenzylideneamino)-2-methylpropan-1-ol
(E)-4-chloro-2-((1-hydroxy-2-methylpropylimino)methyl) phenol
(E)-4-bromo-2-((1-hydroxy-2-methylpropylimino)methyl) phenol
(E)-4-chloro-2-((1-hydroxy-2-methylpropylimino)methyl) phenyl isobutyrate
(E)-4-bromo-2-((1-hydroxy-2-methylpropylimino)methyl) phenyl isobutyrate
(E)-3-chloro-5-((1-hydroxy-2-methylpropylimino)methyl) phenyl 4-methylbenzoate
(E)-3-bromo-5-((1-hydroxy-2-methylpropylimino)methyl) phenyl 4-methylbenzoate
(E)-5-chloro-2-hydroxy-3-((1-hydroxy-2-methylpropylimino)methyl)phenyl 4-methylbenzoate
(E)-5-bromo-2-hydroxy-3-((1-hydroxy-2-methylpropylimino)methyl)phenyl 4-methylbenzoate
(E)-5-chloro-3-((1-hydroxy-2-methylpropylimino)methyl)-2-(isobutyryloxy)phenyl 4-methylbenzoate
(E)-5-bromo-3-((1-hydroxy-2-methylpropylimino)methyl)-2-(isobutyryloxy)phenyl 4-methylbenzoate
(E)-3-chloro-5-((1-hydroxy-2-methylpropylimino)methyl) phenyl 3-methylbenzoate
(E)-3-bromo-5-((1-hydroxy-2-methylpropylimino)methyl) phenyl 3-methylbenzoate
(E)-5-chloro-2-hydroxy-3-((1-hydroxy-2-methylpropylimino)methyl)phenyl 3-methylbenzoate
(E)-5-bromo-2-hydroxy-3-((1-hydroxy-2-methylpropylimino)methyl)phenyl 3-methylbenzoate
(E)-5-chloro-3-((1-hydroxy-2-methylpropylimino)methyl)-2-(isobutyryloxy)phenyl 3-methylbenzoate
(E)-5-bromo-3-((1-hydroxy-2-methylpropylimino)methyl)-2-(isobutyryloxy)phenyl 3-methylbenzoate
(E)-3-chloro-5-((1-hydroxy-2-methylpropylimino)methyl) phenyl nicotinate
(E)-3-bromo-5-((1-hydroxy-2-methylpropylimino)methyl) phenyl nicotinate
(E)-5-chloro-2-hydroxy-3-((1-hydroxy-2-methylpropylimino)methyl)phenyl nicotinate
(E)-5-bromo-2-hydroxy-3-((1-hydroxy-2-methylpropylimino)methyl)phenyl nicotinate
(E)-5-chloro-3-((1-hydroxy-2-methylpropylimino)methyl)-2-(isobutyryloxy)phenyl nicotinate
(E)-5-bromo-3-((1-hydroxy-2-methylpropylimino)methyl)-2-(isobutyryloxy)phenyl nicotinate
(E)-3-chloro-5-((1-hydroxy-2-methylpropylimino)methyl) phenyl isobutyrate
(E)-3-bromo-5-((1-hydroxy-2-methylpropylimino)methyl) phenyl isobutyrate
(E)-5-chloro-2-hydroxy-3-((1-hydroxy-2-methylpropylimino)methyl)phenyl isobutyrate
(E)-5-bromo-2-hydroxy-3-((1-hydroxy-2-methylpropylimino)methyl)phenyl isobutyrate
(E)-5-chloro-2-isobutroxy-3-((1-hydroxy-2-methylpropylimino)methyl)phenyl isobutyrate
(E)-5-bromo-2-isobutroxy-3-((1-hydroxy-2-methylpropylimino)methyl)phenyl isobutyrate
(E)-3-chloro-5-((1-hydroxy-2-methylpropylimino)methyl) phenol
(E)-3-bromo-5-((1-hydroxy-2-methylpropylimino)methyl) phenol
(E)-5-chloro-3-((1-hydroxy-2-methylpropylimino)methyl) benzene-1,2-diol
(E)-5-bromo-3-((1-hydroxy-2-methylpropylimino)methyl) benzene-1,2-diol
(E)-4-chloro-2-hydroxy-6-((1-hydroxy-2-methylpropylimino)methyl)phenyl isobutyrate
(E)-4-bromo-2-hydroxy-6-((1-hydroxy-2-methylpropylimino)methyl)phenyl isobutyrate
methyl 2-(3-chlorobenzylideneamino)-3-methylbutanoate
methyl 2-(3-bromobenzylideneamino)-3-methylbutanoate methyl 2-(5-chloro-2-hydroxybenzylideneamino)-3-methylbutanoate
methyl 2-(5-bromo-2-hydroxybenzylideneamino)-3-methylbutanoate
methyl 2-(5-chloro-2-(isobutyryloxy)benzylideneamino)-3-methylbutanoate
methyl 2-(5-bromo-2-(isobutyryloxy)benzylideneamino)-3-methylbutanoate
3-chloro-5-((1-methoxy-3-methyl-1-oxobutan-2-ylimino)methyl)phenyl 4-methylbenzoate
3-bromo-5-((1-methoxy-3-methyl-1-oxobutan-2-ylimino)methyl)phenyl 4-methylbenzoate
5-chloro-2-hydroxy-3-((1-methoxy-3-methyl-1-oxobutan-2-ylimino)methyl)phenyl 4-methylbenzoate
5-bromo-2-hydroxy-3-((1-methoxy-3-methyl-1-oxobutan-2-ylimino)methyl)phenyl 4-methylbenzoate
5-chloro-2-(isobutyryloxy)-3-((1-methoxy-3-methyl-1-oxobutan-2-ylimino)methyl)phenyl 4-methylbenzoate
5-bromo-2-(isobutyryloxy)-3-((1-methoxy-3-methyl-1-oxobutan-2-ylimino)methyl)phenyl 4-methylbenzoate
3-chloro-5-((1-methoxy-3-methyl-1-oxobutan-2-ylimino)methyl)phenyl 3-methylbenzoate
3-bromo-5-((1-methoxy-3-methyl-1-oxobutan-2-ylimino)methyl)phenyl 3-methylbenzoate
5-chloro-2-hydroxy-3-((1-methoxy-3-methyl-1-oxobutan-2-ylimino)methyl)phenyl 3-methylbenzoate
5-bromo-2-hydroxy-3-((1-methoxy-3-methyl-1-oxobutan-2-ylimino)methyl)phenyl 3-methylbenzoate
5-chloro-2-(isobutyryloxy)-3-((1-methoxy-3-methyl-1-oxobutan-2-ylimino)methyl)phenyl 3-methylbenzoate
5-bromo-2-(isobutyryloxy)-3-((1-methoxy-3-methyl-1-oxobutan-2-ylimino)methyl)phenyl 3-methylbenzoate
3-chloro-5-((1-methoxy-3-methyl-1-oxobutan-2-ylimino)methyl)phenyl nicotinate
3-bromo-5-((1-methoxy-3-methyl-1-oxobutan-2-ylimino)methyl)phenyl nicotinate
5-chloro-2-hydroxy-3-((1-methoxy-3-methyl-1-oxobutan-2-ylimino)methyl)phenyl nicotinate
5-bromo-2-hydroxy-3-((1-methoxy-3-methyl-1-oxobutan-2-ylimino)methyl)phenyl nicotinate
5-chloro-2-(isobutyryloxy)-3-((1-methoxy-3-methyl-1-oxobutan-2-ylimino)methyl)phenyl nicotinate
5-bromo-2-(isobutyryloxy)-3-((1-methoxy-3-methyl-1-oxobutan-2-ylimino)methyl)phenyl nicotinate
methyl 2-(3-chloro-5-(isobutyryloxy)benzylideneamino)-3-methylbutanoate
methyl 2-(3-bromo-5-(isobutyryloxy)benzylideneamino)-3-methylbutanoate
methyl 2-(5-chloro-2-hydroxy-3-(isobutyryloxy)benzylideneamino)-3-methylbutanoate
methyl 2-(5-bromo-2-hydroxy-3-(isobutyryloxy)benzylideneamino)-3-methylbutanoate
methyl 2-(5-chloro-2,3-bis(isobutyryloxy)benzylideneamino)-3-methylbutanoate
methyl 2-(5-bromo-2,3-bis(isobutyryloxy)benzylideneamino)-3-methylbutanoate
methyl 2-(3-chloro-5-hydroxybenzylideneamino)-3-methylbutanoate
methyl 2-(3-bromo-5-hydroxybenzylideneamino)-3-methylbutanoate
methyl 2-(5-chloro-2,3-dihydroxybenzylideneamino)-3-methylbutanoate
methyl 2-(5-bromo-2,3-dihydroxybenzylideneamino)-3-methylbutanoate
methyl 2-(5-chloro-3-hydroxy-2-(3-methylbut-1-en-2-yloxy)benzylideneamino)-3-methylbutanoate
methyl 2-(5-bromo-3-hydroxy-2-(3-methylbut-1-en-2-yloxy)benzylideneamino)-3-methylbutanoate
2-(3-chlorobenzylideneamino)-3-methylbutanoic acid
2-(3-bromobenzylideneamino)-3-methylbutanoic acid
2-(5-chloro-2-hydroxybenzylideneamino)-3-methylbutanoic acid
2-(5-bromo-2-hydroxybenzylideneamino)-3-methylbutanoic acid
2-(5-chloro-2-(isobutyryloxy)benzylideneamino)-3-methylbutanoic acid
2-(5-bromo-2-(isobutyryloxy)benzylideneamino)-3-methylbutanoic acid
2-(3-chloro-5-(4-methylbenzoyloxy)benzylideneamino)-3-methylbutanoic acid
2-(3-bromo-5-(4-methylbenzoyloxy)benzylideneamino)-3-methylbutanoic acid
2-(5-chloro-2-hydroxy-3-(4-methylbenzoyloxy)benzylideneamino)-3-methylbutanoic acid
2-(5-bromo-2-hydroxy-3-(4-methylbenzoyloxy)benzylideneamino)-3-methylbutanoic acid
2-(5-chloro-2-(isobutyryloxy)-3-(4-methylbenzoyloxy)benzylideneamino)-3-methylbutanoic acid
2-(5-bromo-2-(isobutyryloxy)-3-(4-methylbenzoyloxy)benzylideneamino)-3-methylbutanoic acid
2-(3-chloro-5-(3-methylbenzoyloxy)benzylideneamino)-3-methylbutanoic acid
2-(3-bromo-5-(3-methylbenzoyloxy)benzylideneamino)-3-methylbutanoic acid
2-(5-chloro-2-hydroxy-3-(3-methylbenzoyloxy)benzylideneamino)-3-methylbutanoic acid
2-(5-bromo-2-hydroxy-3-(3-methylbenzoyloxy)benzylideneamino)-3-methylbutanoic acid
2-(5-chloro-2-(isobutyryloxy)-3-(3-methylbenzoyloxy)benzylideneamino)-3-methylbutanoic acid
2-(5-bromo-2-(isobutyryloxy)-3-(3-methylbenzoyloxy)benzylideneamino)-3-methylbutanoic acid
2-(3-chloro-5-(nicotinoyloxy)benzylideneamino)-3-methylbutanoic acid
2-(3-bromo-5-(nicotinoyloxy)benzylideneamino)-3-methylbutanoic acid
2-(5-chloro-2-hydroxy-3-(nicotinoyloxy)benzylideneamino)-3-methylbutanoic acid
2-(5-bromo-2-hydroxy-3-(nicotinoyloxy)benzylideneamino)-3-methylbutanoic acid
2-(5-chloro-2-(isobutyryloxy)-3-(nicotinoyloxy)benzylideneamino)-3-methylbutanoic acid
2-(5-bromo-2-(isobutyryloxy)-3-(nicotinoyloxy)benzylideneamino)-3-methylbutanoic acid
2-(3-chloro-5-(isobutyryloxy)benzylideneamino)-3-methylbutanoic acid
2-(3-bromo-5-(isobutyryloxy)benzylideneamino)-3-methylbutanoic acid
2-(5-chloro-2-hydroxy-3-(isobutyryloxy)benzylideneamino)-3-methylbutanoic acid
2-(5-bromo-2-hydroxy-3-(isobutyryloxy)benzylideneamino)-3-methylbutanoic acid
2-(5-chloro-2,3-bis(isobutyryloxy)benzylideneamino)-3-methylbutanoic acid
2-(5-bromo-2,3-bis(isobutyryloxy)benzylideneamino)-3-methylbutanoic acid
2-(3-chloro-5-hydroxybenzylideneamino)-3-methylbutanoic acid
2-(3-bromo-5-hydroxybenzylideneamino)-3-methylbutanoic acid
2-(5-chloro-2,3-dihydroxybenzylideneamino)-3-methylbutanoic acid 2-(5-bromo-2,3-dihydroxybenzylideneamino)-3-methylbutanoic acid
2-(5-chloro-3-hydroxy-2-(isobutyryloxy)benzylideneamino)-3-methylbutanoic acid
2-(5-bromo-3-hydroxy-2-(isobutyryloxy)benzylideneamino)-3-methylbutanoic acid
methyl 2-(3-chlorobenzylideneamino)-3-(4-hydroxyphenyl)propanoate
methyl 2-(3-bromobenzylideneamino)-3-(4-hydroxyphenyl)propanoate
methyl 2-(5-chloro-2-hydroxybenzylideneamino)-3-(4-hydroxyphenyl)propanoate
methyl 2-(5-bromo-2-hydroxybenzylideneamino)-3-(4-hydroxyphenyl)propanoate
methyl 2-(2-isobutricoxy-5-chlorobenzylideneamino)-3-(4-hydroxyphenyl)propanoate
methyl 2-(2-isobutricoxy-5-bromobenzylideneamino)-3-(4-hydroxyphenyl)propanoate
3-chloro-5-((3-(4-hydroxyphenyl)-1-methoxy-1-oxopropan-2-ylimino)methyl)phenyl 4-methylbenzoate
3-bromo-5-((3-(4-hydroxyphenyl)-1-methoxy-1-oxopropan-2-ylimino)methyl)phenyl 4-methylbenzoate
5-chloro-2-hydroxy-3-((3-(4-hydroxyphenyl)-1-methoxy-1-oxopropan-2-ylimino)methyl)phenyl 4-methylbenzoate
5-bromo-2-hydroxy-3-((3-(4-hydroxyphenyl)-1-methoxy-1-oxopropan-2-ylimino)methyl)phenyl 4-methylbenzoate
5-chloro-3-((3-(4-hydroxyphenyl)-1-methoxy-1-oxopropan-2-ylimino)methyl)-2-(isobutyryloxy)phenyl 4-methylbenzoate
5-bromo-3-((3-(4-hydroxyphenyl)-1-methoxy-1-oxopropan-2-ylimino)methyl)-2-(isobutyryloxy)phenyl 4-methylbenzoate
3-chloro-5-((3-(4-hydroxyphenyl)-1-methoxy-1-oxopropan-2-ylimino)methyl)phenyl 3-methylbenzoate
3-bromo-5-((3-(4-hydroxyphenyl)-1-methoxy-1-oxopropan-2-ylimino)methyl)phenyl 3-methylbenzoate
5-chloro-2-hydroxy-3-((3-(4-hydroxyphenyl)-1-methoxy-1-oxopropan-2-ylimino)methyl)phenyl 3-methylbenzoate
5-bromo-2-hydroxy-3-((3-(4-hydroxyphenyl)-1-methoxy-1-oxopropan-2-ylimino)methyl)phenyl 3-methylbenzoate
5-chloro-3-((3-(4-hydroxyphenyl)-1-methoxy-1-oxopropan-2-ylimino)methyl)-2-(isobutyryloxy)phenyl 3-methylbenzoate
5-bromo-3-((3-(4-hydroxyphenyl)-1-methoxy-1-oxopropan-2-ylimino)methyl)-2-(isobutyryloxy)phenyl 3-methylbenzoate
3-chloro-5-((3-(4-hydroxyphenyl)-1-methoxy-1-oxopropan-2-ylimino)methyl)phenyl nicotinate
3-bromo-5-((3-(4-hydroxyphenyl)-1-methoxy-1-oxopropan-2-ylimino)methyl)phenyl nicotinate
5-chloro-2-hydroxy-3-((3-(4-hydroxyphenyl)-1-methoxy-1-oxopropan-2-ylimino)methyl)phenyl nicotinate
5-bromo-2-hydroxy-3-((3-(4-hydroxyphenyl)-1-methoxy-1-oxopropan-2-ylimino)methyl)phenyl nicotinate
5-chloro-3-((3-(4-hydroxyphenyl)-1-methoxy-1-oxopropan-2-ylimino)methyl)-2-(isobutyryloxy)phenyl nicotinate
5-bromo-3-((3-(4-hydroxyphenyl)-1-methoxy-1-oxopropan-2-ylimino)methyl)-2-(isobutyryloxy)phenyl nicotinate
methyl 2-(3-isobutryateoxy-5-chlorobenzylideneamino)-3-(4-hydroxyphenyl)propanoate
methyl 2-(3-isobutryateoxy-5-bromobenzylideneamino)-3-(4-hydroxyphenyl)propanoate
methyl 2-(3-isobutryateoxy-5-chloro-2-hydroxybenzylideneamino)-3-(4-hydroxyphenyl)propanoate
methyl 2-(3-isobutryateoxy-5-bromo-2-hydroxybenzylideneamino)-3-(4-hydroxyphenyl)propanoate
methyl 2-(5-chloro-2,3-bisisobutrateoxybenzylideneamino)-3-(4-hydroxyphenyl)propanoate
methyl 2-(5-bromo-2,3-bisisobutrateoxybenzylideneamino)-3-(4-hydroxyphenyl)propanoate
methyl 2-(3-chloro-5-hydroxybenzylideneamino)-3-(4-hydroxyphenyl)propanoate
methyl 2-(3-bromo-5-hydroxybenzylideneamino)-3-(4-hydroxyphenyl)propanoate
methyl 2-(5-chloro-2,3-dihydroxybenzylideneamino)-3-(4-hydroxyphenyl)propanoate
methyl 2-(5-bromo-2,3-dihydroxybenzylideneamino)-3-(4-hydroxyphenyl)propanoate
methyl 2-(5-chloro-2-isobutrateoxy-3-hydroxybenzylideneamino)-3-(4-hydroxyphenyl)propanoate
methyl 2-(5-bromo-2-isobutrateoxy-3-hydroxybenzylideneamino)-3-(4-hydroxyphenyl)propanoate
2-(3-chlorobenzylideneamino)-3-(4-hydroxyphenyl)propanoic acid
2-(3-bromobenzylideneamino)-3-(4-hydroxyphenyl)propanoic acid
2-(5-chloro-2-hydroxybenzylideneamino)-3-(4-hydroxyphenyl)propanoic acid
2-(5-bromo-2-hydroxybenzylideneamino)-3-(4-hydroxyphenyl)propanoic acid
2-(5-chloro-2-(isobutyryloxy)benzylideneamino)-3-(4-hydroxyphenyl)propanoic acid
2-(5-bromo-2-(isobutyryloxy)benzylideneamino)-3-(4-hydroxyphenyl)propanoic acid
2-(3-chloro-5-(4-methylbenzoyloxy)benzylideneamino)-3-(4-hydroxyphenyl)propanoic acid
2-(3-bromo-5-(4-methylbenzoyloxy)benzylideneamino)-3-(4-hydroxyphenyl)propanoic acid
2-(5-chloro-2-hydroxy-3-(4-methylbenzoyloxy)benzylideneamino)-3-(4-hydroxyphenyl)propanoic acid
2-(5-bromo-2-hydroxy-3-(4-methylbenzoyloxy)benzylideneamino)-3-(4-hydroxyphenyl)propanoic acid
2-(5-chloro-2-(isobutyryloxy)-3-(4-methylbenzoyloxy)benzylideneamino)-3-(4-hydroxyphenyl)propanoic acid
2-(5-bromo-2-(isobutyryloxy)-3-(4-methylbenzoyloxy)benzylideneamino)-3-(4-hydroxyphenyl)propanoic acid
2-(3-chloro-5-(3-methylbenzoyloxy)benzylideneamino)-3-(4-hydroxyphenyl)propanoic acid
2-(3-bromo-5-(3-methylbenzoyloxy)benzylideneamino)-3-(4-hydroxyphenyl)propanoic acid
2-(5-chloro-2-hydroxy-3-(3-methylbenzoyloxy)benzylideneamino)-3-(4-hydroxyphenyl)propanoic acid
2-(5-bromo-2-hydroxy-3-(3-methylbenzoyloxy)benzylideneamino)-3-(4-hydroxyphenyl)propanoic acid
2-(5-chloro-2-(isobutyryloxy)-3-(3-methylbenzoyloxy)benzylideneamino)-3-(4-hydroxyphenyl)propanoic acid
2-(5-bromo-2-(isobutyryloxy)-3-(3-methylbenzoyloxy)benzylideneamino)-3-(4-hydroxyphenyl)propanoic acid
2-(3-chloro-5-(nicotinoyloxy)benzylideneamino)-3-(4-hydroxyphenyl)propanoic acid
2-(3-bromo-5-(nicotinoyloxy)benzylideneamino)-3-(4-hydroxyphenyl)propanoic acid
2-(5-chloro-2-hydroxy-3-(nicotinoyloxy)benzylideneamino)-3-(4-hydroxyphenyl)propanoic acid
2-(5-bromo-2-hydroxy-3-(nicotinoyloxy)benzylideneamino)-3-(4-hydroxyphenyl)propanoic acid
2-(5-chloro-2-(isobutyryloxy)-3-(nicotinoyloxy)benzylideneamino)-3-(4-hydroxyphenyl)propanoic acid
2-(5-bromo-2-(isobutyryloxy)-3-(nicotinoyloxy)benzylideneamino)-3-(4-hydroxyphenyl)propanoic acid 2-(3-chloro-5-(isobutyryloxy)benzylideneamino)-3-(4-hydroxyphenyl)propanoic acid
2-(3-bromo-5-(isobutyryloxy)benzylideneamino)-3-(4-hydroxyphenyl)propanoic acid
2-(5-chloro-2-hydroxy-3-(isobutyryloxy)benzylideneamino)-3-(4-hydroxyphenyl)propanoic acid
2-(5-bromo-2-hydroxy-3-(isobutyryloxy)benzylideneamino)-3-(4-hydroxyphenyl)propanoic acid
2-(5-chloro-2,3-bis(isobutyryloxy)benzylideneamino)-3-(4-hydroxyphenyl)propanoic acid
2-(5-bromo-2,3-bis(isobutyryloxy)benzylideneamino)-3-(4-hydroxyphenyl)propanoic acid
2-(3-chloro-5-hydroxybenzylideneamino)-3-(4-hydroxyphenyl)propanoic acid
2-(3-bromo-5-hydroxybenzylideneamino)-3-(4-hydroxyphenyl)propanoic acid
2-(5-chloro-2,3-dihydroxybenzylideneamino)-3-(4-hydroxyphenyl)propanoic acid
2-(5-bromo-2,3-dihydroxybenzylideneamino)-3-(4-hydroxyphenyl)propanoic acid
2-(5-chloro-3-hydroxy-2-(isobutyryloxy)benzylideneamino)-3-(4-hydroxyphenyl)propanoic acid
2-(5-bromo-3-hydroxy-2-(isobutyryloxy)benzylideneamino)-3-(4-hydroxyphenyl)propanoic acid
(Z)-3-(3-chlorobenzylideneamino)-1-hydroxy-4-(4-hydroxyphenyl)butan-2-one
(Z)-3-(3-bromobenzylideneamino)-1-hydroxy-4-(4-hydroxyphenyl)butan-2-one
(Z)-3-(5-chloro-2-hydroxybenzylideneamino)-1-hydroxy-4-(4-hydroxyphenyl)butan-2-one
(Z)-3-(5-bromo-2-hydroxybenzylideneamino)-1-hydroxy-4-(4-hydroxyphenyl)butan-2-one
(Z)-4-chloro-2-((4-hydroxy-1-(4-hydroxyphenyl)-3-oxobutan-2-ylimino)methyl)phenyl isobutyrate
(Z)-4-bromo-2-((4-hydroxy-1-(4-hydroxyphenyl)-3-oxobutan-2-ylimino)methyl)phenyl isobutyrate
(Z)-3-chloro-5-((4-hydroxy-1-(4-hydroxyphenyl)-3-oxobutan-2-ylimino)methyl)phenyl 4-methylbenzoate
(Z)-3-bromo-5-((4-hydroxy-1-(4-hydroxyphenyl)-3-oxobutan-2-ylimino)methyl)phenyl 4-methylbenzoate
(Z)-5-chloro-2-hydroxy-3-((4-hydroxy-1-(4-hydroxyphenyl)-3-oxobutan-2-ylimino)methyl)phenyl 4-methylbenzoate
(Z)-5-bromo-2-hydroxy-3-((4-hydroxy-1-(4-hydroxyphenyl)-3-oxobutan-2-ylimino)methyl)phenyl 4-methylbenzoate
(Z)-5-chloro-3-((4-hydroxy-1-(4-hydroxyphenyl)-3-oxobutan-2-ylimino)methyl)-2-(isobutyryloxy)phenyl 4-methylbenzoate
(Z)-5-bromo-3-((4-hydroxy-1-(4-hydroxyphenyl)-3-oxobutan-2-ylimino)methyl)-2-(isobutyryloxy)phenyl 4-methylbenzoate
(Z)-3-chloro-5-((4-hydroxy-1-(4-hydroxyphenyl)-3-oxobutan-2-ylimino)methyl)phenyl 3-methylbenzoate
(Z)-3-bromo-5-((4-hydroxy-1-(4-hydroxyphenyl)-3-oxobutan-2-ylimino)methyl)phenyl 3-methylbenzoate
5-chloro-2-hydroxy-3-((4-hydroxy-1-(4-hydroxyphenyl)-3-oxobutan-2-ylimino)methyl)phenyl 3-methylbenzoate
5-bromo-2-hydroxy-3-((4-hydroxy-1-(4-hydroxyphenyl)-3-oxobutan-2-ylimino)methyl)phenyl 3-methylbenzoate
5-chloro-3-((4-hydroxy-1-(4-hydroxyphenyl)-3-oxobutan-2-ylimino)methyl)-2-(isobutyryloxy)phenyl 3-methylbenzoate
5-bromo-3-((4-hydroxy-1-(4-hydroxyphenyl)-3-oxobutan-2-ylimino)methyl)-2-(isobutyryloxy)phenyl 3-methylbenzoate
3-chloro-5-((4-hydroxy-1-(4-hydroxyphenyl)-3-oxobutan-2-ylimino)methyl)phenyl nicotinate
3-bromo-5-((4-hydroxy-1-(4-hydroxyphenyl)-3-oxobutan-2-ylimino)methyl)phenyl nicotinate
5-chloro-2-hydroxy-3-((4-hydroxy-1-(4-hydroxyphenyl)-3-oxobutan-2-ylimino)methyl)phenyl nicotinate
5-bromo-2-hydroxy-3-((4-hydroxy-1-(4-hydroxyphenyl)-3-oxobutan-2-ylimino)methyl)phenyl nicotinate
5-chloro-3-((4-hydroxy-1-(4-hydroxyphenyl)-3-oxobutan-2-ylimino)methyl)-2-(isobutyryloxy)phenyl nicotinate
5-bromo-3-((4-hydroxy-1-(4-hydroxyphenyl)-3-oxobutan-2-ylimino)methyl)-2-(isobutyryloxy)phenyl nicotinate
3-chloro-5-((4-hydroxy-1-(4-hydroxyphenyl)-3-oxobutan-2-ylimino)methyl)phenyl isobutyrate
3-bromo-5-((4-hydroxy-1-(4-hydroxyphenyl)-3-oxobutan-2-ylimino)methyl)phenyl isobutyrate
5-chloro-2-hydroxy-3-((4-hydroxy-1-(4-hydroxyphenyl)-3-oxobutan-2-ylimino)methyl)phenyl isobutyrate
5-bromo-2-hydroxy-3-((4-hydroxy-1-(4-hydroxyphenyl)-3-oxobutan-2-ylimino)methyl)phenyl isobutyrate
3-(5-chloro-2,3-bisisobutryloxybenzylideneamino)-1-hydroxy-4-(4-hydroxyphenyl)butan-2-one
3-(5-bromo-2,3-bisisobutryloxybenzylideneamino)-1-hydroxy-4-(4-hydroxyphenyl)butan-2-one
3-(3-chloro-5-hydroxybenzylideneamino)-1-hydroxy-4-(4-hydroxyphenyl)butan-2-one
3-(3-bromo-5-hydroxybenzylideneamino)-1-hydroxy-4-(4-hydroxyphenyl)butan-2-one
3-(5-chloro-2,3-dihydroxybenzylideneamino)-1-hydroxy-4-(4-hydroxyphenyl)butan-2-one
3-(5-bromo-2,3-dihydroxybenzylideneamino)-1-hydroxy-4-(4-hydroxyphenyl)butan-2-one
4-chloro-2-hydroxy-6-((4-hydroxy-1-(4-hydroxyphenyl)-3-oxobutan-2-ylimino)methyl)phenyl isobutyrate
4-bromo-2-hydroxy-6-((4-hydroxy-1-(4-hydroxyphenyl)-3-oxobutan-2-ylimino)methyl)phenyl isobutyrate
4-(2-(3-chlorobenzylideneamino)-4-methoxy-3-oxobutyl)phenyl isobutyrate
4-(2-(3-bromobenzylideneamino)-4-methoxy-3-oxobutyl)phenyl isobutyrate
4-(2-(5-chloro-2-hydroxybenzylideneamino)-4-methoxy-3-oxobutyl)phenyl isobutyrate
4-(2-(5-bromo-2-hydroxybenzylideneamino)-4-methoxy-3-oxobutyl)phenyl isobutyrate
4-(2-(2-isobutryloxy-5-chlorobenzylideneamino)-4-methoxy-3-oxobutyl)phenyl isobutyrate
4-(2-(2-isobutryloxy-5-bromobenzylideneamino)-4-methoxy-3-oxobutyl)phenyl isobutyrate
3-chloro-5-((1-(4-(isobutyryloxy)phenyl)-4-methoxy-3-oxobutan-2-ylimino)methyl)phenyl 4-methylbenzoate
3-bromo-5-((1-(4-(isobutyryloxy)phenyl)-4-methoxy-3-oxobutan-2-ylimino)methyl)phenyl 4-methylbenzoate
5-chloro-2-hydroxy-3-((1-(4-(isobutyryloxy)phenyl)-4-methoxy-3-oxobutan-2-ylimino)methyl)phenyl 4-methylbenzoate
5-bromo-2-hydroxy-3-((1-(4-(isobutyryloxy)phenyl)-4-methoxy-3-oxobutan-2-ylimino)methyl)phenyl 4-methylbenzoate
5-chloro-2-(isobutyryloxy)-3-((1-(4-(isobutyryloxy)phenyl)-4-methoxy-3-oxobutan-2-ylimino)methyl)phenyl 4-methylbenzoate
5-bromo-2-(isobutyryloxy)-3-((1-(4-(isobutyryloxy)phenyl)-4-methoxy-3-oxobutan-2-ylimino)methyl)phenyl 4-methylbenzoate
3-chloro-5-((1-(4-(isobutyryloxy)phenyl)-4-methoxy-3-oxobutan-2-ylimino)methyl)phenyl 3-methylbenzoate 3-bromo-5-((1-(4-(isobutyryloxy)phenyl)-4-methoxy-3-oxobutan-2-ylimino)methyl)phenyl 3-methylbenzoate
5-chloro-2-hydroxy-3-((1-(4-(isobutyryloxy)phenyl)-4-methoxy-3-oxobutan-2-ylimino)methyl)phenyl 3-methylbenzoate
5-bromo-2-hydroxy-3-((1-(4-(isobutyryloxy)phenyl)-4-methoxy-3-oxobutan-2-ylimino)methyl)phenyl 3-methylbenzoate
5-chloro-2-(isobutyryloxy)-3-((1-(4-(isobutyryloxy)phenyl)-4-methoxy-3-oxobutan-2-ylimino)methyl)phenyl 3-methylbenzoate
5-bromo-2-(isobutyryloxy)-3-((1-(4-(isobutyryloxy)phenyl)-4-methoxy-3-oxobutan-2-ylimino)methyl)phenyl 3-methylbenzoate
3-chloro-5-((1-(4-(isobutyryloxy)phenyl)-4-methoxy-3-oxobutan-2-ylimino)methyl)phenyl nicotinate
3-bromo-5-((1-(4-(isobutyryloxy)phenyl)-4-methoxy-3-oxobutan-2-ylimino)methyl)phenyl nicotinate
5-chloro-2-hydroxy-3-((1-(4-(isobutyryloxy)phenyl)-4-methoxy-3-oxobutan-2-ylimino)methyl)phenyl nicotinate
5-bromo-2-hydroxy-3-((1-(4-(isobutyryloxy)phenyl)-4-methoxy-3-oxobutan-2-ylimino)methyl)phenyl nicotinate
5-chloro-2-(isobutyryloxy)-3-((1-(4-(isobutyryloxy)phenyl)-4-methoxy-3-oxobutan-2-ylimino)methyl)phenyl nicotinate
5-bromo-2-(isobutyryloxy)-3-((1-(4-(isobutyryloxy)phenyl)-4-methoxy-3-oxobutan-2-ylimino)methyl)phenyl nicotinate
4-(2-(3-isobutryloxy-5-chlorobenzylideneamino)-4-methoxy-3-oxobutyl)phenyl isobutyrate
4-(2-(3-isobutryloxy-5-bromobenzylideneamino)-4-methoxy-3-oxobutyl)phenyl isobutyrate
4-(2-(3-isobutryloxy-5-chloro-2-hydroxybenzylideneamino)-4-methoxy-3-oxobutyl)phenyl isobutyrate
4-(2-(3-isobutryloxy-5-bromo-2-hydroxybenzylideneamino)-4-methoxy-3-oxobutyl)phenyl isobutyrate
4-(2-(2,3-bis(isobutryloxy)-5-chlorobenzylideneamino)-4-methoxy-3-oxobutyl)phenyl isobutyrate
4-(2-(2,3-bis(isobutryloxy)-5-chlorobenzylideneamino)-4-methoxy-3-oxobutyl)phenyl isobutyrate
4-(2-(3-chloro-5-hydroxybenzylideneamino)-4-methoxy-3-oxobutyl)phenyl isobutyrate
4-(2-(3-bromo-5-hydroxybenzylideneamino)-4-methoxy-3-oxobutyl)phenyl isobutyrate
4-(2-(5-chloro-2,3-dihydroxybenzylideneamino)-4-methoxy-3-oxobutyl)phenyl isobutyrate
4-(2-(5-bromo-2,3-dihydroxybenzylideneamino)-4-methoxy-3-oxobutyl)phenyl isobutyrate
4-(2-(2-isobutryloxy-5-chloro-3-hydroxybenzylideneamino)-4-methoxy-3-oxobutyl)phenyl isobutyrate
4-(2-(2-isobutryloxy-5-bromo-3-hydroxybenzylideneamino)-4-methoxy-3-oxobutyl)phenyl isobutyrate
N-(3-chlorobenzylidene)-2,4-dichlorobenzenamine
N-(3-bromobenzylidene)-2,4-dichlorobenzenamine
4-chloro-2-((2,4-dichlorophenylimino)methyl)phenol
4-bromo-2-((2,4-dichlorophenylimino)methyl)phenol
4-chloro-2-((2,4-dichlorophenylimino)methyl)phenyl isobutyrate
4-bromo-2-((2,4-dichlorophenylimino)methyl)phenyl isobutyrate
3-chloro-5-((2,4-dichlorophenylimino)methyl)phenyl 4-methylbenzoate
3-bromo-5-((2,4-dichlorophenylimino)methyl)phenyl 4-methylbenzoate
5-chloro-3-((2,4-dichlorophenylimino)methyl)-2-hydroxyphenyl 4-methylbenzoate
5-bromo-3-((2,4-dichlorophenylimino)methyl)-2-hydroxyphenyl 4-methylbenzoate
5-chloro-3-((2,4-dichlorophenylimino)methyl)-2-(isobutyryloxy)phenyl 4-methylbenzoate
5-bromo-3-((2,4-dichlorophenylimino)methyl)-2-(isobutyryloxy)phenyl 4-methylbenzoate
3-chloro-5-((2,4-dichlorophenylimino)methyl)phenyl 3-methylbenzoate
3-bromo-5-((2,4-dichlorophenylimino)methyl)phenyl 3-methylbenzoate
5-chloro-3-((2,4-dichlorophenylimino)methyl)-2-hydroxyphenyl 3-methylbenzoate
5-bromo-3-((2,4-dichlorophenylimino)methyl)-2-hydroxyphenyl 3-methylbenzoate
5-chloro-3-((2,4-dichlorophenylimino)methyl)-2-(isobutyryloxy)phenyl 3-methylbenzoate
5-bromo-3-((2,4-dichlorophenylimino)methyl)-2-(isobutyryloxy)phenyl 3-methylbenzoate
3-chloro-5-((2,4-dichlorophenylimino)methyl)phenyl nicotinate
3-bromo-5-((2,4-dichlorophenylimino)methyl)phenyl nicotinate
5-chloro-3-((2,4-dichlorophenylimino)methyl)-2-hydroxyphenyl nicotinate
5-bromo-3-((2,4-dichlorophenylimino)methyl)-2-hydroxyphenyl nicotinate
5-chloro-3-((2,4-dichlorophenylimino)methyl)-2-(isobutyryloxy)phenyl nicotinate
5-bromo-3-((2,4-dichlorophenylimino)methyl)-2-(isobutyryloxy)phenyl nicotinate
3-chloro-5-((2,4-dichlorophenylimino)methyl)phenyl isobutyrate
3-bromo-5-((2,4-dichlorophenylimino)methyl)phenyl isobutyrate
5-chloro-3-((2,4-dichlorophenylimino)methyl)-2-hydroxyphenyl isobutyrate
5-bromo-3-((2,4-dichlorophenylimino)methyl)-2-hydroxyphenyl isobutyrate
N-(2,3-bis(isobutryloxy)-5-chlorobenzylidene)-2,4-dichlorobenzenamine
N-(2,3-bis(isobutryloxy)-5-bromobenzylidene)-2,4-dichlorobenzenamine
3-chloro-5-((2,4-dichlorophenylimino)methyl)phenol
3-bromo-5-((2,4-dichlorophenylimino)methyl)phenol
5-chloro-3-((2,4-dichlorophenylimino)methyl)benzene-1,2-diol
5-bromo-3-((2,4-dichlorophenylimino)methyl)benzene-1,2-diol
4-chloro-2-((2,4-dichlorophenylimino)methyl)-6-hydroxyphenyl isobutyrate
4-bromo-2-((2,4-dichlorophenylimino)methyl)-6-hydroxyphenyl isobutyrate
N-(3-chlorobenzylidene)-4-chlorobenzenamine
N-(3-bromobenzylidene)-4-chlorobenzenamine
4-chloro-2-((4-chlorophenylimino)methyl)phenol
4-bromo-2-((4-chlorophenylimino)methyl)phenol
4-chloro-2-((4-chlorophenylimino)methyl)phenyl isobutyrate
4-bromo-2-((4-chlorophenylimino)methyl)phenyl isobutyrate
3-chloro-5-((4-chlorophenylimino)methyl)phenyl 4-methylbenzoate
3-bromo-5-((4-chlorophenylimino)methyl)phenyl 4-methylbenzoate
5-chloro-3-((4-chlorophenylimino)methyl)-2-hydroxyphenyl 4-methylbenzoate 5-bromo-3-((4-chlorophenylimino)methyl)-2-hydroxyphenyl 4-methylbenzoate
5-chloro-3-((4-chlorophenylimino)methyl)-2-(isobutyryloxy)phenyl 4-methylbenzoate
5-bromo-3-((4-chlorophenylimino)methyl)-2-(isobutyryloxy)phenyl 4-methylbenzoate
3-chloro-5-((4-chlorophenylimino)methyl)phenyl 3-methylbenzoate
3-bromo-5-((4-chlorophenylimino)methyl)phenyl 3-methylbenzoate
5-chloro-3-((4-chlorophenylimino)methyl)-2-hydroxyphenyl 3-methylbenzoate
5-bromo-3-((4-chlorophenylimino)methyl)-2-hydroxyphenyl 3-methylbenzoate
5-chloro-3-((4-chlorophenylimino)methyl)-2-(isobutyryloxy)phenyl 3-methylbenzoate
5-bromo-3-((4-chlorophenylimino)methyl)-2-(isobutyryloxy)phenyl 3-methylbenzoate
3-chloro-5-((4-chlorophenylimino)methyl)phenyl nicotinate
3-bromo-5-((4-chlorophenylimino)methyl)phenyl nicotinate
5-chloro-3-((4-chlorophenylimino)methyl)-2-hydroxyphenyl nicotinate
5-bromo-3-((4-chlorophenylimino)methyl)-2-hydroxyphenyl nicotinate
5-chloro-3-((4-chlorophenylimino)methyl)-2-(isobutyryloxy)phenyl nicotinate
5-bromo-3-((4-chlorophenylimino)methyl)-2-(isobutyryloxy)phenyl nicotinate
3-chloro-5-((4-chlorophenylimino)methyl)phenyl isobutyrate
3-bromo-5-((4-chlorophenylimino)methyl)phenyl isobutyrate
5-chloro-3-((4-chlorophenylimino)methyl)-2-hydroxyphenyl isobutyrate
5-bromo-3-((4-chlorophenylimino)methyl)-2-hydroxyphenyl isobutyrate
N-(2,3-bis(isobutryloxy)-5-chlorobenzylidene)-4-chlorobenzenamine
N-(2,3-bis(isobutryloxy)-5-bromobenzylidene)-4-chlorobenzenamine
3-chloro-5-((4-chlorophenylimino)methyl)phenol
3-bromo-5-((4-chlorophenylimino)methyl)phenol
5-chloro-3-((4-chlorophenylimino)methyl)benzene-1,2-diol
5-bromo-3-((4-chlorophenylimino)methyl)benzene-1,2-diol
4-chloro-2-((4-chlorophenylimino)methyl)-6-hydroxyphenyl isobutyrate
4-bromo-2-((4-chlorophenylimino)methyl)-6-hydroxyphenyl isobutyrate
N-(3-chlorobenzylidene)-2,3-dichlorobenzenamine
N-(3-bromobenzylidene)-2,3-dichlorobenzenamine
4-chloro-2-((2,3-dichlorophenylimino)methyl)phenol
4-bromo-2-((2,3-dichlorophenylimino)methyl)phenol
4-chloro-2-((2,3-dichlorophenylimino)methyl)phenyl isobutyrate
4-bromo-2-((2,3-dichlorophenylimino)methyl)phenyl isobutyrate
3-chloro-5-((2,3-dichlorophenylimino)methyl)phenyl 4-methylbenzoate
3-bromo-5-((2,3-dichlorophenylimino)methyl)phenyl 4-methylbenzoate
5-chloro-3-((2,3-dichlorophenylimino)methyl)-2-hydroxyphenyl 4-methylbenzoate
5-bromo-3-((2,3-dichlorophenylimino)methyl)-2-hydroxyphenyl 4-methylbenzoate
5-chloro-3-((2,3-dichlorophenylimino)methyl)-2-(isobutyryloxy)phenyl 4-methylbenzoate
5-bromo-3-((2,3-dichlorophenylimino)methyl)-2-(isobutyryloxy)phenyl 4-methylbenzoate
3-chloro-5-((2,3-dichlorophenylimino)methyl)phenyl 3-methylbenzoate
3-bromo-5-((2,3-dichlorophenylimino)methyl)phenyl 3-methylbenzoate
5-chloro-3-((2,3-dichlorophenylimino)methyl)-2-hydroxyphenyl 3-methylbenzoate
5-bromo-3-((2,3-dichlorophenylimino)methyl)-2-hydroxyphenyl 3-methylbenzoate
5-chloro-3-((2,3-dichlorophenylimino)methyl)-2-(isobutyryloxy)phenyl 3-methylbenzoate
5-bromo-3-((2,3-dichlorophenylimino)methyl)-2-(isobutyryloxy)phenyl 3-methylbenzoate
3-chloro-5-((2,3-dichlorophenylimino)methyl)phenyl nicotinate
3-bromo-5-((2,3-dichlorophenylimino)methyl)phenyl nicotinate
5-chloro-3-((2,3-dichlorophenylimino)methyl)-2-hydroxyphenyl nicotinate
5-bromo-3-((2,3-dichlorophenylimino)methyl)-2-hydroxyphenyl nicotinate
5-chloro-3-((2,3-dichlorophenylimino)methyl)-2-(isobutyryloxy)phenyl nicotinate
5-bromo-3-((2,3-dichlorophenylimino)methyl)-2-(isobutyryloxy)phenyl nicotinate
3-chloro-5-((2,3-dichlorophenylimino)methyl)phenyl isobutyrate
3-bromo-5-((2,3-dichlorophenylimino)methyl)phenyl isobutyrate
5-chloro-3-((2,3-dichlorophenylimino)methyl)-2-hydroxyphenyl isobutyrate
5-bromo-3-((2,3-dichlorophenylimino)methyl)-2-hydroxyphenyl isobutyrate
N-(2,3-bis(isobutryloxy)-5-chlorobenzylidene)-2,3-dichlorobenzenamine
N-(2,3-bis(isobutryloxy)-5-bromobenzylidene)-2,3-dichlorobenzenamine
3-chloro-5-((2,3-dichlorophenylimino)methyl)phenol
3-bromo-5-((2,3-dichlorophenylimino)methyl)phenol
5-chloro-3-((2,3-dichlorophenylimino)methyl)benzene-1,2-diol
5-bromo-3-((2,3-dichlorophenylimino)methyl)benzene-1,2-diol
4-chloro-2-((2,3-dichlorophenylimino)methyl)-6-hydroxyphenyl isobutyrate
4-bromo-2-((2,3-dichlorophenylimino)methyl)-6-hydroxyphenyl isobutyrate
N-(3-chlorobenzylidene)-3,5-dichlorobenzenamine
N-(3-bromobenzylidene)-3,5-dichlorobenzenamine
4-chloro-2-((3,5-dichlorophenylimino)methyl)phenol
4-bromo-2-((3,5-dichlorophenylimino)methyl)phenol
4-chloro-2-((3,5-dichlorophenylimino)methyl)phenyl isobutyrate
4-bromo-2-((3,5-dichlorophenylimino)methyl)phenyl isobutyrate
3-chloro-5-((3,5-dichlorophenylimino)methyl)phenyl 4-methylbenzoate
3-bromo-5-((3,5-dichlorophenylimino)methyl)phenyl 4-methylbenzoate
5-chloro-3-((3,5-dichlorophenylimino)methyl)-2-hydroxyphenyl 4-methylbenzoate
5-bromo-3-((3,5-dichlorophenylimino)methyl)-2-hydroxyphenyl 4-methylbenzoate
5-chloro-3-((3,5-dichlorophenylimino)methyl)-2-(isobutyryloxy)phenyl 4-methylbenzoate 5-bromo-3-((3,5-dichlorophenylimino)methyl)-2-(isobutyryloxy)phenyl 4-methylbenzoate
5-chloro-3-((3,5-dichlorophenylimino)methyl)-2-(isobutyryloxy)phenyl 3-methylbenzoate
5-bromo-3-((3,5-dichlorophenylimino)methyl)-2-(isobutyryloxy)phenyl 3-methylbenzoate
5-chloro-3-((3,5-dichlorophenylimino)methyl)-2-hydroxyphenyl 3-methylbenzoate
5-bromo-3-((3,5-dichlorophenylimino)methyl)-2-hydroxyphenyl 3-methylbenzoate
5-chloro-3-((3,5-dichlorophenylimino)methyl)-2-(isobutyryloxy)phenyl 3-methylbenzoate
5-bromo-3-((3,5-dichlorophenylimino)methyl)-2-(isobutyryloxy)phenyl 3-methylbenzoate
3-chloro-5-((3,5-dichlorophenylimino)methyl)phenyl nicotinate
3-bromo-5-((3,5-dichlorophenylimino)methyl)phenyl nicotinate
5-chloro-3-((3,5-dichlorophenylimino)methyl)-2-hydroxyphenyl nicotinate
5-bromo-3-((3,5-dichlorophenylimino)methyl)-2-hydroxyphenyl nicotinate
5-chloro-3-((3,5-dichlorophenylimino)methyl)-2-(isobutyryloxy)phenyl nicotinate
5-bromo-3-((3,5-dichlorophenylimino)methyl)-2-(isobutyryloxy)phenyl nicotinate
3-chloro-5-((3,5-dichlorophenylimino)methyl)phenyl isobutyrate
3-bromo-5-((3,5-dichlorophenylimino)methyl)phenyl isobutyrate
5-chloro-3-((3,5-dichlorophenylimino)methyl)-2-hydroxyphenyl isobutyrate
5-bromo-3-((3,5-dichlorophenylimino)methyl)-2-hydroxyphenyl isobutyrate
N-(2,3-bis(isobutryloxy)-5-chlorobenzylidene)-3,5-dichlorobenzenamine
N-(2,3-bis(isobutryloxy)-5-bromobenzylidene)-3,5-dichlorobenzenamine
3-chloro-5-((3,5-dichlorophenylimino)methyl)phenol
3-bromo-5-((3,5-dichlorophenylimino)methyl)phenol
5-chloro-3-((3,5-dichlorophenylimino)methyl)benzene-1,2-diol
5-bromo-3-((3,5-dichlorophenylimino)methyl)benzene-1,2-diol
4-chloro-2-((3,5-dichlorophenylimino)methyl)-6-hydroxyphenyl isobutyrate
4-bromo-2-((3,5-dichlorophenylimino)methyl)-6-hydroxyphenyl isobutyrate
N-(3-chlorobenzylidene)-2-phenylethanamine
N-(3-bromobenzylidene)-2-phenylethanamine
4-chloro-2-((phenethylimino)methyl)phenol
4-bromo-2-((phenethylimino)methyl)phenol
4-chloro-2-((phenethylimino)methyl)phenyl isobutyrate
4-bromo-2-((phenethylimino)methyl)phenyl isobutyrate
3-chloro-5-((phenethylimino)methyl)phenyl 4-methylbenzoate
3-bromo-5-((phenethylimino)methyl)phenyl 4-methylbenzoate
5-chloro-2-hydroxy-3-((phenethylimino)methyl)phenyl 4-methylbenzoate
5-bromo-2-hydroxy-3-((phenethylimino)methyl)phenyl 4-methylbenzoate
5-chloro-2-(isobutyryloxy)-3-((phenethylimino)methyl)phenyl 4-methylbenzoate
5-bromo-2-(isobutyryloxy)-3-((phenethylimino)methyl)phenyl 4-methylbenzoate
3-chloro-5-((phenethylimino)methyl)phenyl 3-methylbenzoate
3-bromo-5-((phenethylimino)methyl)phenyl 3-methylbenzoate
5-chloro-2-hydroxy-3-((phenethylimino)methyl)phenyl 3-methylbenzoate
5-bromo-2-hydroxy-3-((phenethylimino)methyl)phenyl 3-methylbenzoate
5-chloro-2-(isobutyryloxy)-3-((phenethylimino)methyl)phenyl 3-methylbenzoate
5-bromo-2-(isobutyryloxy)-3-((phenethylimino)methyl)phenyl 3-methylbenzoate
3-chloro-5-((phenethylimino)methyl)phenyl nicotinate
3-bromo-5-((phenethylimino)methyl)phenyl nicotinate
5-chloro-2-hydroxy-3-((phenethylimino)methyl)phenyl nicotinate
5-bromo-2-hydroxy-3-((phenethylimino)methyl)phenyl nicotinate
5-chloro-2-(isobutyryloxy)-3-((phenethylimino)methyl)phenyl nicotinate
5-bromo-2-(isobutyryloxy)-3-((phenethylimino)methyl)phenyl nicotinate
3-chloro-5-((phenethylimino)methyl)phenyl isobutyrate
3-bromo-5-((phenethylimino)methyl)phenyl isobutyrate
5-chloro-2-hydroxy-3-((phenethylimino)methyl)phenyl isobutyrate
5-bromo-2-hydroxy-3-((phenethylimino)methyl)phenyl isobutyrate
N-(2,3-bis(isobutrylloxy)-5-chlorobenzylidene)-2-phenylethanamine
N-(2,3-bis(isobutrylloxy)-5-bromobenzylidene)-2-phenylethanamine
3-chloro-5-((phenethylimino)methyl)phenol
3-bromo-5-((phenethylimino)methyl)phenol
5-chloro-3-((phenethylimino)methyl)benzene-1,2-diol
5-bromo-3-((phenethylimino)methyl)benzene-1,2-diol
4-chloro-2-hydroxy-6-((phenethylimino)methyl)phenyl isobutyrate
4-bromo-2-hydroxy-6-((phenethylimino)methyl)phenyl isobutyrate
N-(3-chlorobenzylidene)-4-((diethylamino)methyl)benzenamine
N-(3-bromobenzylidene)-4-((diethylamino)methyl)benzenamine
4-chloro-2-((4-((diethylamino)methyl)phenylimino)methyl)phenol
4-bromo-2-((4-((diethylamino)methyl)phenylimino)methyl)phenol
4-chloro-2-((4-((diethylamino)methyl)phenylimino)methyl)phenyl isobutyrate
4-bromo-2-((4-((diethylamino)methyl)phenylimino)methyl)phenyl isobutyrate
3-chloro-5-((4-((diethylamino)methyl)phenylimino)methyl)phenyl 4-methylbenzoate
3-bromo-5-((4-((diethylamino)methyl)phenylimino)methyl)phenyl 4-methylbenzoate
5-chloro-3-((4-((diethylamino)methyl)phenylimino)methyl)-2-hydroxyphenyl 4-methylbenzoate
5-bromo-3-((4-((diethylamino)methyl)phenylimino)methyl)-2-hydroxyphenyl 4-methylbenzoate
5-chloro-3-((4-((diethylamino)methyl)phenylimino)methyl)-2-(isobutyryloxy)phenyl 4-methylbenzoate
5-bromo-3-((4-((diethylamino)methyl)phenylimino)methyl)-2-(isobutyryloxy)phenyl 4-methylbenzoate
3-chloro-5-((4-((diethylamino)methyl)phenylimino)methyl)phenyl 3-methylbenzoate 3-bromo-5-((4-((diethylamino)methyl)phenylimino)methyl)phenyl 3-methylbenzoate
5-chloro-3-((4-((diethylamino)methyl)phenylimino)methyl)-2-hydroxyphenyl 3-methylbenzoate
5-bromo-3-((4-((diethylamino)methyl)phenylimino)methyl)-2-hydroxyphenyl 3-methylbenzoate
5-chloro-3-((4-((diethylamino)methyl)phenylimino)methyl)-2-(isobutyryloxy)phenyl 3-methylbenzoate
5-bromo-3-((4-((diethylamino)methyl)phenylimino)methyl)-2-(isobutyryloxy)phenyl 3-methylbenzoate
3-chloro-5-((4-((diethylamino)methyl)phenylimino)methyl)phenyl nicotinate
3-bromo-5-((4-((diethylamino)methyl)phenylimino)methyl)phenyl nicotinate
5-chloro-3-((4-((diethylamino)methyl)phenylimino)methyl)-2-hydroxyphenyl nicotinate
5-bromo-3-((4-((diethylamino)methyl)phenylimino)methyl)-2-hydroxyphenyl nicotinate
5-chloro-3-((4-((diethylamino)methyl)phenylimino)methyl)-2-(isobutyryloxy)phenyl nicotinate
5-bromo-3-((4-((diethylamino)methyl)phenylimino)methyl)-2-(isobutyryloxy)phenyl nicotinate
3-chloro-5-((4-((diethylamino)methyl)phenylimino)methyl)phenyl isobutyrate
3-bromo-5-((4-((diethylamino)methyl)phenylimino)methyl)phenyl isobutyrate
5-chloro-3-((4-((diethylamino)methyl)phenylimino)methyl)-2-hydroxyphenyl isobutyrate
5-bromo-3-((4-((diethylamino)methyl)phenylimino)methyl)-2-hydroxyphenyl isobutyrate
N-(2,3-bis(isobutryloxy)-5-chlorobenzylidene)-4-((diethylamino)methyl)benzenamine
N-(2,3-bis(isobutryloxy)-5-bromobenzylidene)-4-((diethylamino)methyl)benzenamine
3-chloro-5-((4-((diethylamino)methyl)phenylimino)methyl)phenol
3-bromo-5-((4-((diethylamino)methyl)phenylimino)methyl)phenol
5-chloro-3-((4-((diethylamino)methyl)phenylimino)methyl)benzene-1,2-diol
5-bromo-3-((4-((diethylamino)methyl)phenylimino)methyl)benzene-1,2-diol
4-chloro-2-((4-((diethylamino)methyl)phenylimino)methyl)-6-hydroxyphenyl isobutyrate
4-bromo-2-((4-((diethylamino)methyl)phenylimino)methyl)-6-hydroxyphenyl isobutyrate
N-(3-chlorobenzylidene)pyridin-3-amine
N-(3-bromobenzylidene)pyridin-3-amine
4-chloro-2-((pyridin-3-ylimino)methyl)phenol
4-bromo-2-((pyridin-3-ylimino)methyl)phenol
4-chloro-2-((pyridin-3-ylimino)methyl)phenyl isobutyrate
4-bromo-2-((pyridin-3-ylimino)methyl)phenyl isobutyrate
3-chloro-5-((pyridin-3-ylimino)methyl)phenyl 4-methylbenzoate
3-bromo-5-((pyridin-3-ylimino)methyl)phenyl 4-methylbenzoate
5-chloro-2-hydroxy-3-((pyridin-3-ylimino)methyl)phenyl 4-methylbenzoate
5-bromo-2-hydroxy-3-((pyridin-3-ylimino)methyl)phenyl 4-methylbenzoate
5-chloro-2-(isobutyryloxy)-3-((pyridin-3-ylimino)methyl)phenyl 4-methylbenzoate
5-bromo-2-(isobutyryloxy)-3-((pyridin-3-ylimino)methyl)phenyl 4-methylbenzoate
3-chloro-5-((pyridin-3-ylimino)methyl)phenyl 3-methylbenzoate
3-bromo-5-((pyridin-3-ylimino)methyl)phenyl 3-methylbenzoate
5-chloro-2-hydroxy-3-((pyridin-3-ylimino)methyl)phenyl 3-methylbenzoate
5-bromo-2-hydroxy-3-((pyridin-3-ylimino)methyl)phenyl 3-methylbenzoate
5-chloro-2-(isobutyryloxy)-3-((pyridin-3-ylimino)methyl)phenyl 3-methylbenzoate
5-bromo-2-(isobutyryloxy)-3-((pyridin-3-ylimino)methyl)phenyl 3-methylbenzoate
3-chloro-5-((pyridin-3-ylimino)methyl)phenyl nicotinate
3-bromo-5-((pyridin-3-ylimino)methyl)phenyl nicotinate
5-chloro-2-hydroxy-3-((pyridin-3-ylimino)methyl)phenyl nicotinate
5-bromo-2-hydroxy-3-((pyridin-3-ylimino)methyl)phenyl nicotinate
5-chloro-2-(isobutyryloxy)-3-((pyridin-3-ylimino)methyl)phenyl nicotinate
5-bromo-2-(isobutyryloxy)-3-((pyridin-3-ylimino)methyl)phenyl nicotinate
3-chloro-5-((pyridin-3-ylimino)methyl)phenyl isobutyrate
3-bromo-5-((pyridin-3-ylimino)methyl)phenyl isobutyrate
5-chloro-2-hydroxy-3-((pyridin-3-ylimino)methyl)phenyl isobutyrate
5-bromo-2-hydroxy-3-((pyridin-3-ylimino)methyl)phenyl isobutyrate
N-(2,3-bis(isobutryloxy)-5-chlorobenzylidene)pyridin-3-amine
N-(2,3-bis(isobutryloxy)-5-bromobenzylidene)pyridin-3-amine
3-chloro-5-((pyridin-3-ylimino)methyl)phenol
3-bromo-5-((pyridin-3-ylimino)methyl)phenol
5-chloro-3-((pyridin-3-ylimino)methyl)benzene-1,2-diol
5-bromo-3-((pyridin-3-ylimino)methyl)benzene-1,2-diol
4-chloro-2-hydroxy-6-((pyridin-3-ylimino)methyl)phenyl isobutyrate
4-bromo-2-hydroxy-6-((pyridin-3-ylimino)methyl)phenyl isobutyrate
3-(3-chlorobenzylideneamino)benzoic acid
3-(3-bromobenzylideneamino)benzoic acid
3-(5-chloro-2-hydroxybenzylideneamino)benzoic acid
3-(5-bromo-2-hydroxybenzylideneamino)benzoic acid
3-(5-chloro-2-(isobutyryloxy)benzylideneamino)benzoic acid
3-(5-bromo-2-(isobutyryloxy)benzylideneamino)benzoic acid
3-(3-chloro-5-(4-methylbenzoyloxy)benzylideneamino)benzoic acid
3-(3-bromo-5-(4-methylbenzoyloxy)benzylideneamino)benzoic acid
3-(5-chloro-2-hydroxy-3-(4-methylbenzoyloxy)benzylideneamino)benzoic acid
3-(5-bromo-2-hydroxy-3-(4-methylbenzoyloxy)benzylideneamino)benzoic acid
3-(5-chloro-2-(isobutyryloxy)-3-(4-methylbenzoyloxy)benzylideneamino)benzoic acid
3-(5-bromo-2-(isobutyryloxy)-3-(4-methylbenzoyloxy)benzylideneamino)benzoic acid
3-(3-chloro-5-(3-methylbenzoyloxy)benzylideneamino)benzoic acid
3-(3-bromo-5-(3-methylbenzoyloxy)benzylideneamino)benzoic acid
3-(5-chloro-2-hydroxy-3-(3-methylbenzoyloxy)benzylideneamino)benzoic acid
3-(5-bromo-2-hydroxy-3-(3-methylbenzoyloxy)benzylideneamino)benzoic acid 3-(5-chloro-2-(isobutyryloxy)-3-(3-methylbenzoyloxy)benzylideneamino)benzoic acid
3-(5-bromo-2-(isobutyryloxy)-3-(3-methylbenzoyloxy)benzylideneamino)benzoic acid
3-(3-chloro-5-(nicotinoyloxy)benzylideneamino)benzoic acid
3-(3-bromo-5-(nicotinoyloxy)benzylideneamino)benzoic acid
3-(5-chloro-2-hydroxy-3-(nicotinoyloxy)benzylideneamino)benzoic acid
3-(5-bromo-2-hydroxy-3-(nicotinoyloxy)benzylideneamino)benzoic acid
3-(5-chloro-2-(isobutyryloxy)-3-(nicotinoyloxy)benzylideneamino)benzoic acid
3-(5-bromo-2-(isobutyryloxy)-3-(nicotinoyloxy)benzylideneamino)benzoic acid
3-(3-chloro-5-(isobutyryloxy)benzylideneamino)benzoic acid
3-(3-bromo-5-(isobutyryloxy)benzylideneamino)benzoic acid
3-(5-chloro-2-hydroxy-3-(isobutyryloxy)benzylideneamino)benzoic acid
3-(5-bromo-2-hydroxy-3-(isobutyryloxy)benzylideneamino)benzoic acid
3-(2,3-bis(isobutryloxy)-5-chlorobenzylideneamino)benzoic acid
3-(2,3-bis(isobutryloxy)-5-bromobenzylideneamino)benzoic acid
3-(3-chloro-5-hydroxybenzylideneamino)benzoic acid
3-(3-bromo-5-hydroxybenzylideneamino)benzoic acid
3-(5-chloro-2,3-dihydroxybenzylideneamino)benzoic acid
3-(5-bromo-2,3-dihydroxybenzylideneamino)benzoic acid
3-(5-chloro-3-hydroxy-2-(isobutyryloxy)benzylideneamino)benzoic acid
3-(5-bromo-3-hydroxy-2-(isobutyryloxy)benzylideneamino)benzoic acid

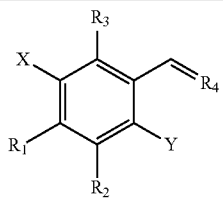

$R_1 = R_3 = H$ $R_4$ is bonded though N, $R_2$ in cases is bonded through O

| S.No | R4 | R2 | Y | X |
|---|---|---|---|---|
| 1. | HO-CH(iPr)-N | H | H | Cl |
| 2. | HO-CH(iPr)-N | H | H | Br |
| 3. | HO-CH(iPr)-N | H | OH | Cl |
| 4. | HO-CH(iPr)-N | H | OH | Br |
| 5. | HO-CH(iPr)-N | H | O-C(=O)-CH(CH3)2 | Cl |
| 6. | HO-CH(iPr)-N | H | O-C(=O)-CH(CH3)2 | Br |
| 7. | HO-CH(iPr)-N | O-C(=O)-(4-methylphenyl) | H | Cl |

-continued

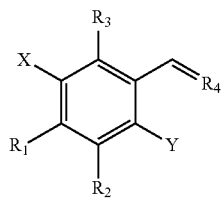

R1 = R3 = H

R4 is bonded though N, R2 in cases is bonded through O

| S.No | R4 | R2 | Y | X |
|---|---|---|---|---|
| 8. | HO-CH(iPr)-N | 4-methylbenzoate (O-linked) | H | Br |
| 9. | HO-CH(iPr)-N | 4-methylbenzoate (O-linked) | OH | Cl |
| 10. | HO-CH(iPr)-N | 4-methylbenzoate (O-linked) | OH | Br |
| 11. | HO-CH(iPr)-N | 4-methylbenzoate (O-linked) | isobutyrate (O-linked) | Cl |
| 12. | HO-CH(iPr)-N | 4-methylbenzoate (O-linked) | isobutyrate (O-linked) | Br |
| 13. | HO-CH(iPr)-N | 3-methylbenzoate (O-linked) | H | Cl |
| 14. | HO-CH(iPr)-N | 3-methylbenzoate (O-linked) | H | Br |

-continued
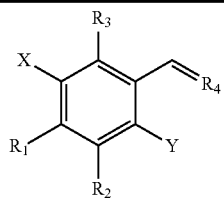
R1 = R3 = H
R4 is bonded though N, R2 in cases is bonded through O
| S.No | R4 | R2 | Y | X |
|---|---|---|---|---|
| 15. | HO-CH(iPr)-N | 3-carboxylatobenzoate | OH | Cl |
| 16. | HO-CH(iPr)-N | 3-carboxylatobenzoate | OH | Br |
| 17. | HO-CH(iPr)-N | 3-carboxylatobenzoate | isobutyryloxy | Cl |
| 18. | HO-CH(iPr)-N | 3-carboxylatobenzoate | isobutyryloxy | Br |
| 19. | HO-CH(iPr)-N | nicotinate | H | Cl |
| 20. | HO-CH(iPr)-N | nicotinate | H | Br |
| 21. | HO-CH(iPr)-N | nicotinate | OH | Cl |

-continued
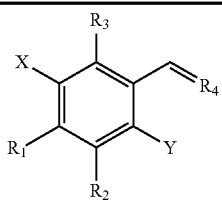
R1 = R3 = H
R4 is bonded though N, R2 in cases is bonded through O
| S.No | R4 | R2 | Y | X |
|---|---|---|---|---|
| 22. | HO-CH(iPr)-N | nicotinoyloxy (O-C(=O)-pyridin-3-yl) | OH | Br |
| 23. | HO-CH(iPr)-N | nicotinoyloxy | O-C(=O)-iPr | Cl |
| 24. | HO-CH(iPr)-N | nicotinoyloxy | O-C(=O)-iPr | Br |
| 25. | HO-CH(iPr)-N | O-C(=O)-iPr | H | Cl |
| 26. | HO-CH(iPr)-N | O-C(=O)-iPr | H | Br |
| 27. | HO-CH(iPr)-N | O-C(=O)-iPr | OH | Cl |
| 28. | HO-CH(iPr)-N | O-C(=O)-iPr | OH | Br |
| 29. | HO-CH(iPr)-N | O-C(=O)-iPr | O-C(=O)-iPr | Cl |
| 30. | HO-CH(iPr)-N | O-C(=O)-iPr | O-C(=O)-iPr | Br |
| 31. | HO-CH(iPr)-N | OH | H | Cl |

-continued
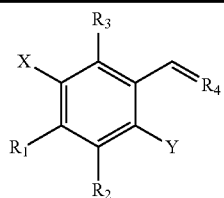
R1 = R3 = H
R4 is bonded though N, R2 in cases is bonded through O
| S.No | R4 | R2 | Y | X |
|---|---|---|---|---|
| 32. | HO-CH(N)-CH(CH3)2 | OH | H | Br |
| 33. | HO-CH(N)-CH(CH3)2 | OH | OH | Cl |
| 34. | HO-CH(N)-CH(CH3)2 | OH | OH | Br |
| 35. | HO-CH(N)-CH(CH3)2 | OH | O-C(=O)-CH(CH3) | Cl |
| 36. | HO-CH(N)-CH(CH3)2 | OH | O-C(=O)-CH(CH3) | Br |
| 37. | N-CH(iPr)-C(=O)-O-CH3 | H | H | Cl |
| 38. | N-CH(iPr)-C(=O)-O-CH3 | H | H | Br |
| 39. | N-CH(iPr)-C(=O)-O-CH3 | H | OH | Cl |
| 40. | N-CH(iPr)-C(=O)-O-CH3 | H | OH | Br |
| 41. | N-CH(iPr)-C(=O)-O-CH3 | H | O-C(=O)-CH(CH3) | Cl |

-continued
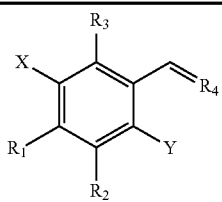
R1 = R3 = H
R4 is bonded though N, R2 in cases is bonded through O
| S.No | R4 | R2 | Y | X |
|---|---|---|---|---|
| 42. | N-CH(CH(CH3)2)-C(=O)-O-CH3 | H | O-C(=O)-CH(CH3)2 | Br |
| 43. | N-CH(CH(CH3)2)-C(=O)-O-CH3 | O-C(=O)-C6H4-CH3 | H | Cl |
| 44. | N-CH(CH(CH3)2)-C(=O)-O-CH3 | O-C(=O)-C6H4-CH3 | H | Br |
| 45. | N-CH(CH(CH3)2)-C(=O)-O-CH3 | O-C(=O)-C6H4-CH3 | OH | Cl |
| 46. | N-CH(CH(CH3)2)-C(=O)-O-CH3 | O-C(=O)-C6H4-CH3 | OH | Br |
| 47. | N-CH(CH(CH3)2)-C(=O)-O-CH3 | O-C(=O)-C6H4-CH3 | O-C(=O)-CH(CH3)2 | Cl |
| 48. | N-CH(CH(CH3)2)-C(=O)-O-CH3 | O-C(=O)-C6H4-CH3 | O-C(=O)-CH(CH3)2 | Br |
| 49. | N-CH(CH(CH3)2)-C(=O)-O-CH3 | O-C(=O)-C6H4(m-CH3) | H | Cl |

-continued
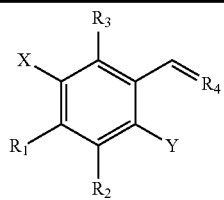
R1 = R3 = H
R4 is bonded though N, R2 in cases is bonded through O
| S.No | R4 | R2 | Y | X |
|---|---|---|---|---|
| 50. | N-CH(iPr)-C(=O)-O-CH3 | 3-carboxybenzoate | H | Br |
| 51. | N-CH(iPr)-C(=O)-O-CH3 | 3-carboxybenzoate | OH | Cl |
| 52. | N-CH(iPr)-C(=O)-O-CH3 | 3-carboxybenzoate | OH | Br |
| 53. | N-CH(iPr)-C(=O)-O-CH3 | 3-carboxybenzoate | O-C(=O)-CH(CH3)2 | Cl |
| 54. | N-CH(iPr)-C(=O)-O-CH3 | 3-carboxybenzoate | O-C(=O)-CH(CH3)2 | Br |
| 55. | N-CH(iPr)-C(=O)-O-CH3 | nicotinate | H | Cl |
| 56. | N-CH(iPr)-C(=O)-O-CH3 | nicotinate | H | Br |

-continued

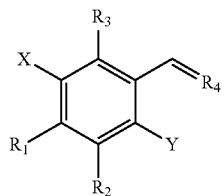

R1 = R3 = H

R4 is bonded though N, R2 in cases is bonded through O

| S.No | R4 | R2 | Y | X |
|---|---|---|---|---|
| 57. | valine methyl ester (N-bonded) | nicotinate (O-bonded) | OH | Cl |
| 58. | valine methyl ester (N-bonded) | nicotinate (O-bonded) | OH | Br |
| 59. | valine methyl ester (N-bonded) | nicotinate (O-bonded) | isobutyrate | Cl |
| 60. | valine methyl ester (N-bonded) | nicotinate (O-bonded) | isobutyrate | Br |
| 61. | valine methyl ester (N-bonded) | isobutyrate | H | Cl |
| 62. | valine methyl ester (N-bonded) | isobutyrate | H | Br |
| 63. | valine methyl ester (N-bonded) | isobutyrate | OH | Cl |
| 64. | valine methyl ester (N-bonded) | isobutyrate | OH | Br |

-continued
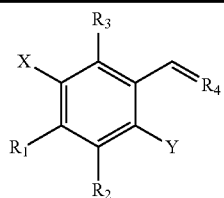
R1 = R3 = H
R4 is bonded though N, R2 in cases is bonded through O
| S.No | R4 | R2 | Y | X |
|---|---|---|---|---|
| 65. | N-CH(iPr)-C(=O)-O-CH3 | O-C(=O)-CH(CH3)2 | O-C(=O)-CH(CH3)2 | Cl |
| 66. | N-CH(iPr)-C(=O)-O-CH3 | O-C(=O)-CH(CH3)2 | O-C(=O)-CH(CH3)2 | Br |
| 67. | N-CH(iPr)-C(=O)-O-CH3 | OH | H | Cl |
| 68. | N-CH(iPr)-C(=O)-O-CH3 | OH | H | Br |
| 69. | N-CH(iPr)-C(=O)-O-CH3 | OH | OH | Cl |
| 70. | N-CH(iPr)-C(=O)-O-CH3 | OH | OH | Br |
| 71. | N-CH(iPr)-C(=O)-O-CH3 | OH | O-C(=O)-CH(CH3)2 | Cl |
| 72. | N-CH(iPr)-C(=O)-O-CH3 | OH | O-C(=O)-CH(CH3)2 | Br |
| 73. | N-CH(iPr)-C(=O)-OH | H | H | Cl |

-continued
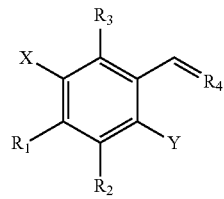
R1 = R3 = H
R4 is bonded though N, R2 in cases is bonded through O
| S.No | R4 | R2 | Y | X |
|---|---|---|---|---|
| 74. | N-CH(iPr)-COOH | H | H | Br |
| 75. | N-CH(iPr)-COOH | H | OH | Cl |
| 76. | N-CH(iPr)-COOH | H | OH | Br |
| 77. | N-CH(iPr)-COOH | H | O-CO-CH(CH3)2 | Cl |
| 78. | N-CH(iPr)-COOH | H | O-CO-CH(CH3)2 | Br |
| 79. | N-CH(iPr)-COOH | O-CO-C6H4-CH3 | H | Cl |
| 80. | N-CH(iPr)-COOH | O-CO-C6H4-CH3 | H | Br |
| 81. | N-CH(iPr)-COOH | O-CO-C6H4-CH3 | OH | Cl |

-continued
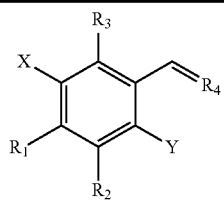
R1 = R3 = H
R4 is bonded though N, R2 in cases is bonded through O
| S.No | R4 | R2 | Y | X |
|---|---|---|---|---|
| 82. | valine | 4-methylbenzoate | OH | Br |
| 83. | valine | 4-methylbenzoate | isobutyrate | Cl |
| 84. | valine | 4-methylbenzoate | isobutyrate | Br |
| 85. | valine | 3-methylbenzoate | H | Cl |
| 86. | valine | 3-methylbenzoate | H | Br |
| 87. | valine | 3-methylbenzoate | OH | Cl |
| 88. | valine | 3-methylbenzoate | OH | Br |

-continued
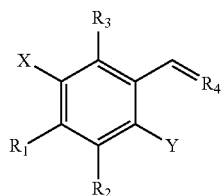
R1 = R3 = H
R4 is bonded though N, R2 in cases is bonded through O
| S.No | R4 | R2 | Y | X |
|---|---|---|---|---|
| 89. | Valine | 3-methylbenzoate | isobutyrate | Cl |
| 90. | Valine | 3-methylbenzoate | isobutyrate | Br |
| 91. | Valine | nicotinate | H | Cl |
| 92. | Valine | nicotinate | H | Br |
| 93. | Valine | nicotinate | OH | Cl |
| 94. | Valine | nicotinate | OH | Br |
| 95. | Valine | nicotinate | isobutyrate | Cl |

-continued
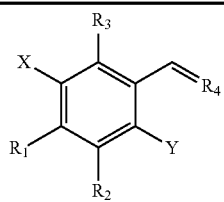
R1 = R3 = H
R4 is bonded though N, R2 in cases is bonded through O
| S.No | R4 | R2 | Y | X |
|---|---|---|---|---|
| 96. | N-CH(iPr)-COOH (valine) | nicotinoyloxy (O-C(=O)-pyridin-3-yl) | O-C(=O)-iPr | Br |
| 97. | N-CH(iPr)-COOH | O-C(=O)-iPr | H | Cl |
| 98. | N-CH(iPr)-COOH | O-C(=O)-iPr | H | Br |
| 99. | N-CH(iPr)-COOH | O-C(=O)-iPr | OH | Cl |
| 100. | N-CH(iPr)-COOH | O-C(=O)-iPr | OH | Br |
| 101. | N-CH(iPr)-COOH | O-C(=O)-iPr | O-C(=O)-iPr | Cl |
| 102. | N-CH(iPr)-COOH | O-C(=O)-iPr | O-C(=O)-iPr | Br |
| 103. | N-CH(iPr)-COOH | OH | H | Cl |
| 104. | N-CH(iPr)-COOH | OH | H | Br |

-continued

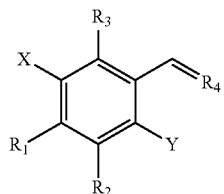

R1 = R3 = H

R4 is bonded though N, R2 in cases is bonded through O

| S.No | R4 | R2 | Y | X |
|---|---|---|---|---|
| 105. | N-CH(iPr)-C(=O)OH (valine, N-linked) | OH | OH | Cl |
| 106. | N-CH(iPr)-C(=O)OH (valine, N-linked) | OH | OH | Br |
| 107. | N-CH(iPr)-C(=O)OH (valine, N-linked) | OH | O-C(=O)-CH(CH3)2 | Cl |
| 108. | N-CH(iPr)-C(=O)OH (valine, N-linked) | OH | O-C(=O)-CH(CH3)2 | Br |
| 109. | N-CH(CH2-C6H4-OH)-C(=O)OCH3 (tyrosine methyl ester, N-linked) | H | H | Cl |
| 110. | N-CH(CH2-C6H4-OH)-C(=O)OCH3 (tyrosine methyl ester, N-linked) | H | H | Br |
| 111. | N-CH(CH2-C6H4-OH)-C(=O)OCH3 (tyrosine methyl ester, N-linked) | H | OH | Cl |

-continued
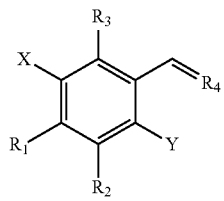
R1 = R3 = H
R₄ is bonded though N, R₂ in cases is bonded through O
| S.No | R4 | R2 | Y | X |
|---|---|---|---|---|
| 112. | 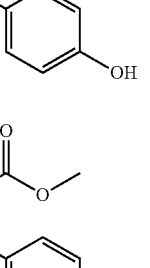 | H | OH | Br |
| 113. | 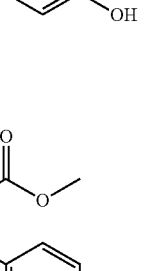 | H |  | Cl |
| 114. | 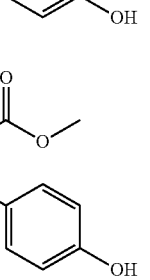 | H | 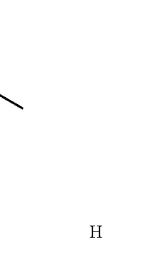 | Br |
| 115. | 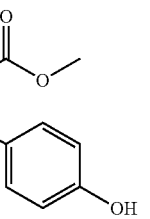 | 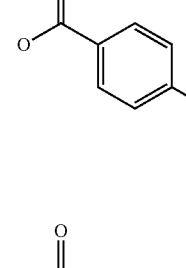 | H | Cl |
| 116. | 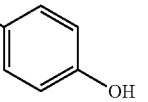 | 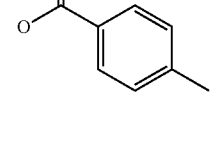 | H | Br |

-continued

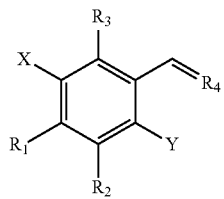

R1 = R3 = H

R4 is bonded though N, R2 in cases is bonded through O

| S.No | R4 | R2 | Y | X |
|---|---|---|---|---|
| 117. | methyl 2-amino-3-(4-hydroxyphenyl)propanoate (N-linked) | 4-methylbenzoate (O-linked) | OH | Cl |
| 118. | methyl 2-amino-3-(4-hydroxyphenyl)propanoate (N-linked) | 4-methylbenzoate (O-linked) | OH | Br |
| 119. | methyl 2-amino-3-(4-hydroxyphenyl)propanoate (N-linked) | 4-methylbenzoate (O-linked) | isobutyrate (O-linked) | Cl |
| 120. | methyl 2-amino-3-(4-hydroxyphenyl)propanoate (N-linked) | 4-methylbenzoate (O-linked) | isobutyrate (O-linked) | Br |
| 121. | methyl 2-amino-3-(4-hydroxyphenyl)propanoate (N-linked) | 3-methylbenzoate (O-linked) | H | Cl |

-continued

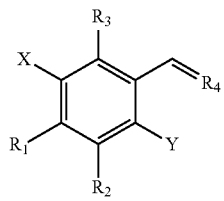

R1 = R3 = H

R₄ is bonded though N, R₂ in cases is bonded through O

| S.No | R4 | R2 | Y | X |
|---|---|---|---|---|
| 122. | methyl tyrosinate (N-linked) | 3-methylbenzoate (O-linked) | H | Br |
| 123. | methyl tyrosinate (N-linked) | 3-methylbenzoate (O-linked) | OH | Cl |
| 124. | methyl tyrosinate (N-linked) | 3-methylbenzoate (O-linked) | OH | Br |
| 125. | methyl tyrosinate (N-linked) | 3-methylbenzoate (O-linked) | isobutyryloxy | Cl |
| 126. | methyl tyrosinate (N-linked) | 3-methylbenzoate (O-linked) | isobutyryloxy | Br |

-continued
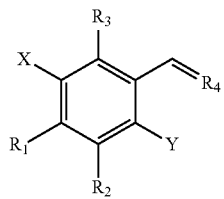
R1 = R3 = H
R4 is bonded though N, R2 in cases is bonded through O
| S.No | R4 | R2 | Y | X |
|---|---|---|---|---|
| 127. | methyl tyrosinate (N-linked) | nicotinate | H | Cl |
| 128. | methyl tyrosinate (N-linked) | nicotinate | H | Br |
| 129. | methyl tyrosinate (N-linked) | nicotinate | OH | Cl |
| 130. | methyl tyrosinate (N-linked) | nicotinate | OH | Br |
| 131. | methyl tyrosinate (N-linked) | nicotinate | isobutyrate | Cl |

-continued

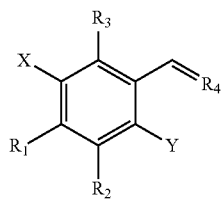

R1 = R3 = H

R4 is bonded though N, R2 in cases is bonded through O

| S.No | R4 | R2 | Y | X |
|---|---|---|---|---|
| 132. | methyl 2-amino-3-(4-hydroxyphenyl)propanoate (N-linked) | nicotinoyloxy | isobutyryloxy | Br |
| 133. | methyl 2-amino-3-(4-hydroxyphenyl)propanoate (N-linked) | isobutyryloxy | H | Cl |
| 134. | methyl 2-amino-3-(4-hydroxyphenyl)propanoate (N-linked) | isobutyryloxy | H | Br |
| 135. | methyl 2-amino-3-(4-hydroxyphenyl)propanoate (N-linked) | isobutyryloxy | OH | Cl |
| 136. | methyl 2-amino-3-(4-hydroxyphenyl)propanoate (N-linked) | isobutyryloxy | OH | Br |

-continued

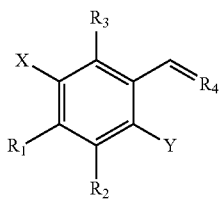

R1 = R3 = H

R4 is bonded though N, R2 in cases is bonded through O

| S.No | R4 | R2 | Y | X |
|---|---|---|---|---|
| 137. | methyl 2-amino-3-(4-hydroxyphenyl)propanoate (N-bonded) | isobutyryloxy (O-bonded) | isobutyryloxy (O-bonded) | Cl |
| 138. | methyl 2-amino-3-(4-hydroxyphenyl)propanoate (N-bonded) | isobutyryloxy (O-bonded) | isobutyryloxy (O-bonded) | Br |
| 139. | methyl 2-amino-3-(4-hydroxyphenyl)propanoate (N-bonded) | OH | H | Cl |
| 140. | methyl 2-amino-3-(4-hydroxyphenyl)propanoate (N-bonded) | OH | H | Br |
| 141. | methyl 2-amino-3-(4-hydroxyphenyl)propanoate (N-bonded) | OH | OH | Cl |

-continued

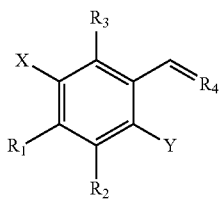

R1 = R3 = H

R₄ is bonded though N, R₂ in cases is bonded through O

| S.No | R4 | R2 | Y | X |
|---|---|---|---|---|
| 142. | methyl 2-amino-3-(4-hydroxyphenyl)propanoate (N-bonded) | OH | OH | Br |
| 143. | methyl 2-amino-3-(4-hydroxyphenyl)propanoate (N-bonded) | OH | O-C(=O)-CH(CH₃)₂ | Cl |
| 144. | methyl 2-amino-3-(4-hydroxyphenyl)propanoate (N-bonded) | OH | O-C(=O)-CH(CH₃)₂ | Br |
| 145. | 2-amino-3-(4-hydroxyphenyl)propanoic acid (N-bonded) | H | H | Cl |
| 146. | 2-amino-3-(4-hydroxyphenyl)propanoic acid (N-bonded) | H | H | Br |

-continued
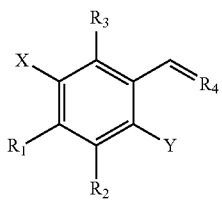
R1 = R3 = H
R4 is bonded though N, R2 in cases is bonded through O
| S.No | R4 | R2 | Y | X |
|---|---|---|---|---|
| 147. | N-CH(COOH)-CH2-C6H4-OH | H | OH | Cl |
| 148. | N-CH(COOH)-CH2-C6H4-OH | H | OH | Br |
| 149. | N-CH(COOH)-CH2-C6H4-OH | H | O-C(=O)-CH(CH3)2 | Cl |
| 150. | N-CH(COOH)-CH2-C6H4-OH | H | O-C(=O)-CH(CH3)2 | Br |
| 151. | N-CH(COOH)-CH2-C6H4-OH | O-C(=O)-C6H4-CH3 | H | Cl |

-continued
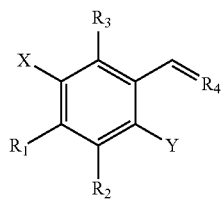
R1 = R3 = H
R4 is bonded though N, R2 in cases is bonded through O
| S.No | R4 | R2 | Y | X |
|---|---|---|---|---|
| 152. | N-CH(COOH)-CH2-C6H4-OH | O-CO-C6H4-CH3 | H | Br |
| 153. | N-CH(COOH)-CH2-C6H4-OH | O-CO-C6H4-CH3 | OH | Cl |
| 154. | N-CH(COOH)-CH2-C6H4-OH | O-CO-C6H4-CH3 | OH | Br |
| 155. | N-CH(COOH)-CH2-C6H4-OH | O-CO-C6H4-CH3 | O-CO-CH(CH3)2 | Cl |
| 156. | N-CH(COOH)-CH2-C6H4-OH | O-CO-C6H4-CH3 | O-CO-CH(CH3)2 | Br |

-continued
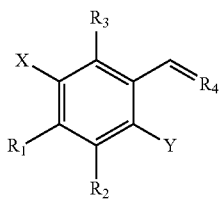
R1 = R3 = H
R4 is bonded though N, R2 in cases is bonded through O
| S.No | R4 | R2 | Y | X |
|---|---|---|---|---|
| 157. | N-CH(CH2-C6H4-OH)-COOH (tyrosine) | 3-methylbenzoate | H | Cl |
| 158. | N-CH(CH2-C6H4-OH)-COOH (tyrosine) | 3-methylbenzoate | H | Br |
| 159. | N-CH(CH2-C6H4-OH)-COOH (tyrosine) | 3-methylbenzoate | OH | Cl |
| 160. | N-CH(CH2-C6H4-OH)-COOH (tyrosine) | 3-methylbenzoate | OH | Br |
| 161. | N-CH(CH2-C6H4-OH)-COOH (tyrosine) | 3-methylbenzoate | O-C(=O)-CH(CH3)2 | Cl |

-continued
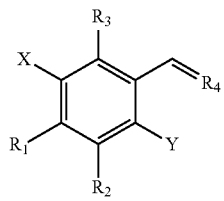
R1 = R3 = H
R4 is bonded though N, R2 in cases is bonded through O
| S.No | R4 | R2 | Y | X |
|---|---|---|---|---|
| 162. | tyrosine (N-bonded) | 3-methylbenzoate (O-bonded) | isobutyrate (O-bonded) | Br |
| 163. | tyrosine (N-bonded) | nicotinate (O-bonded) | H | Cl |
| 164. | tyrosine (N-bonded) | nicotinate (O-bonded) | H | Br |
| 165. | tyrosine (N-bonded) | nicotinate (O-bonded) | OH | Cl |
| 166. | tyrosine (N-bonded) | nicotinate (O-bonded) | OH | Br |

-continued
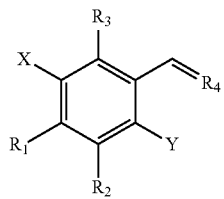
R1 = R3 = H
R4 is bonded though N, R2 in cases is bonded through O
| S.No | R4 | R2 | Y | X |
|---|---|---|---|---|
| 167. | N-CH(CH2-C6H4-OH)-COOH (tyrosine) | nicotinoyloxy | isobutyryloxy | Cl |
| 168. | N-CH(CH2-C6H4-OH)-COOH (tyrosine) | nicotinoyloxy | isobutyryloxy | Br |
| 169. | N-CH(CH2-C6H4-OH)-COOH (tyrosine) | isobutyryloxy | H | Cl |
| 170. | N-CH(CH2-C6H4-OH)-COOH (tyrosine) | isobutyryloxy | H | Br |
| 171. | N-CH(CH2-C6H4-OH)-COOH (tyrosine) | isobutyryloxy | OH | Cl |

-continued
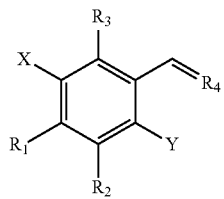
R1 = R3 = H
R4 is bonded though N, R2 in cases is bonded through O
| S.No | R4 | R2 | Y | X |
|------|----|----|---|---|
| 172. | N-CH(COOH)-CH2-C6H4-OH | isobutyryl-O | OH | Br |
| 173. | N-CH(COOH)-CH2-C6H4-OH | isobutyryl-O | isobutyryl-O | Cl |
| 174. | N-CH(COOH)-CH2-C6H4-OH | isobutyryl-O | isobutyryl-O | Br |
| 175. | N-CH(COOH)-CH2-C6H4-OH | OH | H | Cl |
| 176. | N-CH(COOH)-CH2-C6H4-OH | OH | H | Br |

-continued
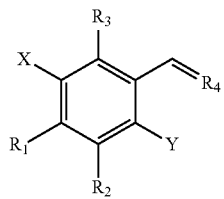
R1 = R3 = H
R4 is bonded though N, R2 in cases is bonded through O
| S.No | R4 | R2 | Y | X |
|---|---|---|---|---|
| 177. | N-CH(COOH)-CH2-C6H4-OH | OH | OH | Cl |
| 178. | N-CH(COOH)-CH2-C6H4-OH | OH | OH | Br |
| 179. | N-CH(COOH)-CH2-C6H4-OH | OH | O-C(=O)-CH(CH3)2 | Cl |
| 180. | N-CH(COOH)-CH2-C6H4-OH | OH | O-C(=O)-CH(CH3)2 | Br |
| 181. | N-CH(C(=O)CH2OH)-CH2-C6H4-OH | H | H | Cl |

-continued
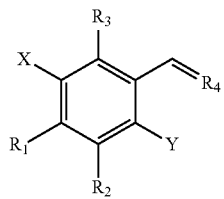
R1 = R3 = H
R4 is bonded though N, R2 in cases is bonded through O
| S.No | R4 | R2 | Y | X |
|---|---|---|---|---|
| 182. | N-CH(CH2-C6H4-OH)-C(O)-CH2OH | H | H | Br |
| 183. | N-CH(CH2-C6H4-OH)-C(O)-CH2OH | H | OH | Cl |
| 184. | N-CH(CH2-C6H4-OH)-C(O)-CH2OH | H | OH | Br |
| 185. | N-CH(CH2-C6H4-OH)-C(O)-CH2OH | H | O-C(O)-CH(CH3)2 | Cl |
| 186. | N-CH(CH2-C6H4-OH)-C(O)-CH2OH | H | O-C(O)-CH(CH3)2 | Br |

-continued
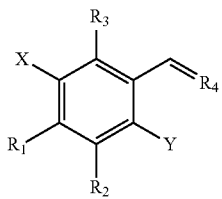
R1 = R3 = H
R₄ is bonded though N, R₂ in cases is bonded through O
| S.No | R4 | R2 | Y | X |
|---|---|---|---|---|
| 187. | N-CH(CH₂-C₆H₄-OH)-C(O)-CH₂OH | 4-methylbenzoate (O-linked) | H | Cl |
| 188. | N-CH(CH₂-C₆H₄-OH)-C(O)-CH₂OH | 4-methylbenzoate (O-linked) | H | Br |
| 189. | N-CH(CH₂-C₆H₄-OH)-C(O)-CH₂OH | 4-methylbenzoate (O-linked) | OH | Cl |
| 190. | N-CH(CH₂-C₆H₄-OH)-C(O)-CH₂OH | 4-methylbenzoate (O-linked) | OH | Br |
| 191. | N-CH(CH₂-C₆H₄-OH)-C(O)-CH₂OH | 4-methylbenzoate (O-linked) | isobutyrate (O-linked) | Cl |

-continued
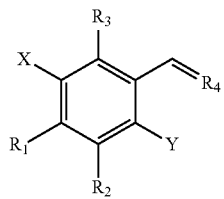
R1 = R3 = H
R4 is bonded though N, R2 in cases is bonded through O
| S.No | R4 | R2 | Y | X |
|---|---|---|---|---|
| 192. | N-CH(CH2-C6H4-OH)-C(=O)-CH2OH | 4-methylbenzoate (O-linked) | isobutyryloxy | Br |
| 193. | N-CH(CH2-C6H4-OH)-C(=O)-CH2OH | 3-methylbenzoate (O-linked) | H | Cl |
| 194. | N-CH(CH2-C6H4-OH)-C(=O)-CH2OH | 3-methylbenzoate (O-linked) | H | Br |
| 195. | N-CH(CH2-C6H4-OH)-C(=O)-CH2OH | 3-methylbenzoate (O-linked) | OH | Cl |
| 196. | N-CH(CH2-C6H4-OH)-C(=O)-CH2OH | 3-methylbenzoate (O-linked) | OH | Br |

-continued
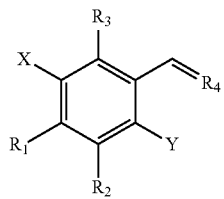
R1 = R3 = H
R4 is bonded though N, R2 in cases is bonded through O
| S.No | R4 | R2 | Y | X |
|---|---|---|---|---|
| 197. | N-CH(CH2-C6H4-OH)-C(O)-CH2OH | 3-methylbenzoate (O-linked) | isobutyryloxy | Cl |
| 198. | N-CH(CH2-C6H4-OH)-C(O)-CH2OH | 3-methylbenzoate (O-linked) | isobutyryloxy | Br |
| 199. | N-CH(CH2-C6H4-OH)-C(O)-CH2OH | nicotinate (O-linked) | H | Cl |
| 200. | N-CH(CH2-C6H4-OH)-C(O)-CH2OH | nicotinate (O-linked) | H | Br |
| 201. | N-CH(CH2-C6H4-OH)-C(O)-CH2OH | nicotinate (O-linked) | OH | Cl |

-continued
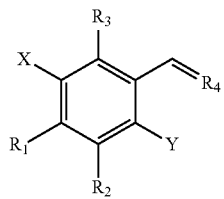
R1 = R3 = H
R4 is bonded though N, R2 in cases is bonded through O
| S.No | R4 | R2 | Y | X |
|---|---|---|---|---|
| 202. | N-CH(CH2-C6H4-OH)-C(=O)-CH2OH | nicotinate (O-C(=O)-pyridin-3-yl) | OH | Br |
| 203. | N-CH(CH2-C6H4-OH)-C(=O)-CH2OH | nicotinate | isobutyrate | Cl |
| 204. | N-CH(CH2-C6H4-OH)-C(=O)-CH2OH | nicotinate | isobutyrate | Br |
| 205. | N-CH(CH2-C6H4-OH)-C(=O)-CH2OH | isobutyrate | H | Cl |
| 206. | N-CH(CH2-C6H4-OH)-C(=O)-CH2OH | isobutyrate | H | Br |

-continued
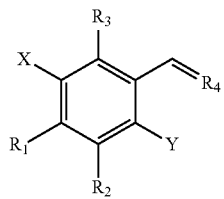
R1 = R3 = H
R4 is bonded though N, R2 in cases is bonded through O
| S.No | R4 | R2 | Y | X |
|------|----|----|----|----|
| 207. | N-CH(CH2-C6H4-OH)-C(=O)-CH2OH | OC(=O)CH(CH3)2 | OH | Cl |
| 208. | N-CH(CH2-C6H4-OH)-C(=O)-CH2OH | OC(=O)CH(CH3)2 | OH | Br |
| 209. | N-CH(CH2-C6H4-OH)-C(=O)-CH2OH | OC(=O)CH(CH3)2 | OC(=O)CH(CH3)2 | Cl |
| 210. | N-CH(CH2-C6H4-OH)-C(=O)-CH2OH | OC(=O)CH(CH3)2 | OC(=O)CH(CH3)2 | Br |
| 211. | N-CH(CH2-C6H4-OH)-C(=O)-CH2OH | OH | H | Cl |

-continued

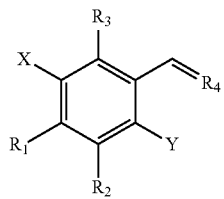

R1 = R3 = H

R4 is bonded though N, R2 in cases is bonded through O

| S.No | R4 | R2 | Y | X |
|---|---|---|---|---|
| 212. | *tyrosine-derived group with N, C=O, CH, CH2-OH, and 4-hydroxyphenyl* | OH | H | Br |
| 213. | *tyrosine-derived group with N, C=O, CH, CH2-OH, and 4-hydroxyphenyl* | OH | OH | Cl |
| 214. | *tyrosine-derived group with N, C=O, CH, CH2-OH, and 4-hydroxyphenyl* | OH | OH | Br |
| 215. | *tyrosine-derived group with N, C=O, CH, CH2-OH, and 4-hydroxyphenyl* | OH | isobutyryloxy (O-C(=O)-CH(CH3)2) | Cl |
| 216. | *tyrosine-derived group with N, C=O, CH, CH2-OH, and 4-hydroxyphenyl* | OH | isobutyryloxy (O-C(=O)-CH(CH3)2) | Br |

-continued
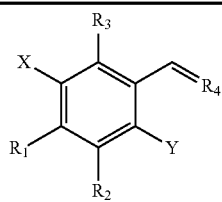
R1 = R3 = H
R4 is bonded though N, R2 in cases is bonded through O
| S.No | R4 | R2 | Y | X |
|---|---|---|---|---|
| 217. | | H | H | Cl |
| 218. | | H | H | Br |
| 219. | | H | OH | Cl |
| 220. | | H | OH | Br |
| 221. | | H | | Cl |

-continued
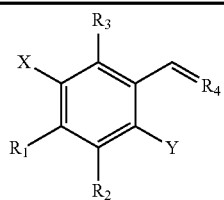
R1 = R3 = H
R4 is bonded though N, R2 in cases is bonded through O
| S.No | R4 | R2 | Y | X |
|---|---|---|---|---|
| 222. | | H | | Br |
| 223. | | | H | Cl |
| 224. | | | H | Br |
| 225. | | | OH | Cl |
| 226. | | | OH | Br |

-continued
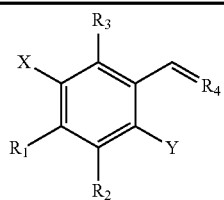
R1 = R3 = H
R₄ is bonded though N, R₂ in cases is bonded through O
| S.No | R4 | R2 | Y | X |
|---|---|---|---|---|
| 227. | | | | Cl |
| 228. | | | | Br |
| 229. | | | H | Cl |
| 230. | | | H | Br |
| 231. | | | OH | Cl |

-continued
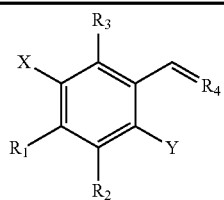
R1 = R3 = H
R4 is bonded though N, R2 in cases is bonded through O
| S.No | R4 | R2 | Y | X |
|---|---|---|---|---|
| 232. | | | OH | Br |
| 233. | | | Cl | |
| 234. | | | Br | |
| 235. | | | H | Cl |
| 236. | | | H | Br |

-continued
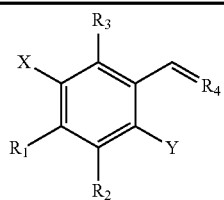
R1 = R3 = H
R4 is bonded though N, R2 in cases is bonded through O
| S.No | R4 | R2 | Y | X |
|---|---|---|---|---|
| 237. | | | OH | Cl |
| 238. | | | OH | Br |
| 239. | | | | Cl |
| 240. | | | | Br |
| 241. | | | H | Cl |

-continued
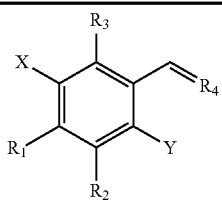
R1 = R3 = H
R4 is bonded though N, R2 in cases is bonded through O
| S.No | R4 | R2 | Y | X |
|---|---|---|---|---|
| 242. | | | H | Br |
| 243. | | | OH | Cl |
| 244. | | | OH | Br |
| 245. | | | | Cl |
| 246. | | | | Br |

-continued
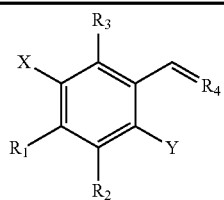
R1 = R3 = H
R4 is bonded though N, R2 in cases is bonded through O
| S.No | R4 | R2 | Y | X |
|---|---|---|---|---|
| 247. | | OH | H | Cl |
| 248. | | OH | H | Br |
| 249. | | OH | OH | Cl |
| 250. | | OH | OH | Br |
| 251. | | OH | | Cl |

-continued
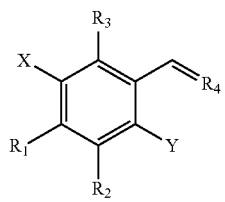
R1 = R3 = H
R4 is bonded though N, R2 in cases is bonded through O
| S.No | R4 | R2 | Y | X |
|---|---|---|---|---|
| 252. | N-CH(CH2-C6H4-O-C(=O)-CH(CH3)2)-C(=O)-CH2-O-CH3 | OH | O-C(=O)-CH(CH3)2 | Br |
| 253. | 2,4-dichloroanilino | H | H | Cl |
| 254. | 2,4-dichloroanilino | H | H | Br |
| 255. | 2,4-dichloroanilino | H | OH | Cl |
| 256. | 2,4-dichloroanilino | H | OH | Br |
| 257. | 2,4-dichloroanilino | H | O-C(=O)-CH(CH3)2 | Cl |
| 258. | 2,4-dichloroanilino | H | O-C(=O)-CH(CH3)2 | Br |
| 259. | 2,4-dichloroanilino | O-C(=O)-C6H4-CH3 | H | Cl |

-continued

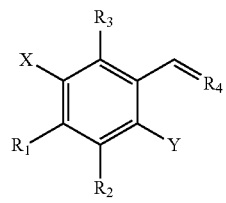

R1 = R3 = H

R4 is bonded though N, R2 in cases is bonded through O

| S.No | R4 | R2 | Y | X |
|---|---|---|---|---|
| 260. | N-(2,4-dichlorophenyl) | 4-methylbenzoate | H | Br |
| 261. | N-(2,4-dichlorophenyl) | 4-methylbenzoate | OH | Cl |
| 262. | N-(2,4-dichlorophenyl) | 4-methylbenzoate | OH | Br |
| 263. | N-(2,4-dichlorophenyl) | 4-methylbenzoate | isobutyryloxy | Cl |
| 264. | N-(2,4-dichlorophenyl) | 4-methylbenzoate | isobutyryloxy | Br |
| 265. | N-(2,4-dichlorophenyl) | 3-methylbenzoate | H | Cl |
| 266. | N-(2,4-dichlorophenyl) | 3-methylbenzoate | H | Br |

-continued

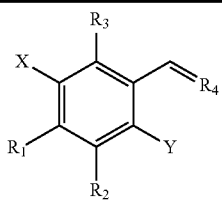

R1 = R3 = H

R4 is bonded though N, R2 in cases is bonded through O

| S.No | R4 | R2 | Y | X |
|---|---|---|---|---|
| 267. | 2,4-dichlorophenyl-N | 3-methylbenzoate-O | OH | Cl |
| 268. | 2,4-dichlorophenyl-N | 3-methylbenzoate-O | OH | Br |
| 269. | 2,4-dichlorophenyl-N | 3-methylbenzoate-O | isobutyryloxy | Cl |
| 270. | 2,4-dichlorophenyl-N | 3-methylbenzoate-O | isobutyryloxy | Br |
| 271. | 2,4-dichlorophenyl-N | nicotinate-O | H | Cl |
| 272. | 2,4-dichlorophenyl-N | nicotinate-O | H | Br |
| 273. | 2,4-dichlorophenyl-N | nicotinate-O | OH | Cl |

-continued

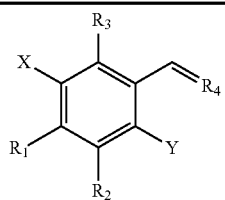

R1 = R3 = H

R4 is bonded though N, R2 in cases is bonded through O

| S.No | R4 | R2 | Y | X |
|---|---|---|---|---|
| 274. | 2,4-dichlorophenyl-N | nicotinoyloxy | OH | Br |
| 275. | 2,4-dichlorophenyl-N | nicotinoyloxy | isobutyryloxy | Cl |
| 276. | 2,4-dichlorophenyl-N | nicotinoyloxy | isobutyryloxy | Br |
| 277. | 2,4-dichlorophenyl-N | isobutyryloxy | H | Cl |
| 278. | 2,4-dichlorophenyl-N | isobutyryloxy | H | Br |
| 279. | 2,4-dichlorophenyl-N | isobutyryloxy | OH | Cl |
| 280. | 2,4-dichlorophenyl-N | isobutyryloxy | OH | Br |
| 281. | 2,4-dichlorophenyl-N | isobutyryloxy | isobutyryloxy | Cl |
| 282. | 2,4-dichlorophenyl-N | isobutyryloxy | isobutyryloxy | Br |

-continued
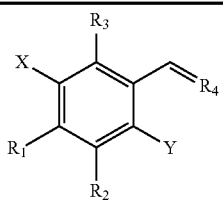
R1 = R3 = H
R₄ is bonded though N, R₂ in cases is bonded through O
| S.No | R4 | R2 | Y | X |
|---|---|---|---|---|
| 283. | 2,4-dichlorophenyl-N | OH | H | Cl |
| 284. | 2,4-dichlorophenyl-N | OH | H | Br |
| 285. | 2,4-dichlorophenyl-N | OH | OH | Cl |
| 286. | 2,4-dichlorophenyl-N | OH | OH | Br |
| 287. | 2,4-dichlorophenyl-N | OH | OC(O)CH(CH₃)₂ | Cl |
| 288. | 2,4-dichlorophenyl-N | OH | OC(O)CH(CH₃)₂ | Br |
| 289. | 4-chlorophenyl-N | H | H | Cl |
| 290. | 4-chlorophenyl-N | H | H | Br |
| 291. | 4-chlorophenyl-N | H | OH | Cl |
| 292. | 4-chlorophenyl-N | H | OH | Br |

-continued
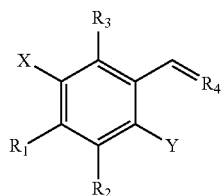
R1 = R3 = H
R4 is bonded though N, R2 in cases is bonded through O
| S.No | R4 | R2 | Y | X |
|---|---|---|---|---|
| 293. | 4-Cl-C6H4-N | H | OC(O)CH(CH3)2 | Cl |
| 294. | 4-Cl-C6H4-N | H | OC(O)CH(CH3)2 | Br |
| 295. | 4-Cl-C6H4-N | OC(O)-C6H4-4-CH3 | H | Cl |
| 296. | 4-Cl-C6H4-N | OC(O)-C6H4-4-CH3 | H | Br |
| 297. | 4-Cl-C6H4-N | OC(O)-C6H4-4-CH3 | OH | Cl |
| 298. | 4-Cl-C6H4-N | OC(O)-C6H4-4-CH3 | OH | Br |
| 299. | 4-Cl-C6H4-N | OC(O)-C6H4-4-CH3 | OC(O)CH(CH3)2 | Cl |
| 300. | 4-Cl-C6H4-N | OC(O)-C6H4-4-CH3 | OC(O)CH(CH3)2 | Br |

-continued
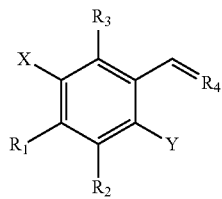
R1 = R3 = H
R4 is bonded though N, R2 in cases is bonded through O
| S.No | R4 | R2 | Y | X |
|---|---|---|---|---|
| 301. | 4-chlorophenyl-N | 3-methylbenzoate-O | H | Cl |
| 302. | 4-chlorophenyl-N | 3-methylbenzoate-O | H | Br |
| 303. | 4-chlorophenyl-N | 3-methylbenzoate-O | OH | Cl |
| 304. | 4-chlorophenyl-N | 3-methylbenzoate-O | OH | Br |
| 305. | 4-chlorophenyl-N | 3-methylbenzoate-O | isobutyryloxy | Cl |
| 306. | 4-chlorophenyl-N | 3-methylbenzoate-O | isobutyryloxy | Br |

-continued

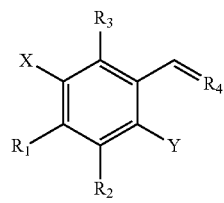

R1 = R3 = H

R4 is bonded though N, R2 in cases is bonded through O

| S.No | R4 | R2 | Y | X |
|---|---|---|---|---|
| 307. | N-C6H4-Cl (4-chloroanilino) | nicotinoyloxy | H | Cl |
| 308. | N-C6H4-Cl (4-chloroanilino) | nicotinoyloxy | H | Br |
| 309. | N-C6H4-Cl (4-chloroanilino) | nicotinoyloxy | OH | Cl |
| 310. | N-C6H4-Cl (4-chloroanilino) | nicotinoyloxy | OH | Br |
| 311. | N-C6H4-Cl (4-chloroanilino) | nicotinoyloxy | isobutyryloxy | Cl |
| 312. | N-C6H4-Cl (4-chloroanilino) | nicotinoyloxy | isobutyryloxy | Br |
| 313. | N-C6H4-Cl (4-chloroanilino) | isobutyryloxy | H | Cl |
| 314. | N-C6H4-Cl (4-chloroanilino) | isobutyryloxy | H | Br |

-continued
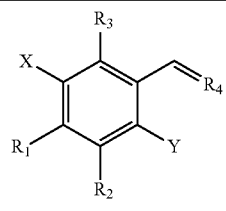
R1 = R3 = H
R4 is bonded though N, R2 in cases is bonded through O
| S.No | R4 | R2 | Y | X |
|---|---|---|---|---|
| 315. | N-C6H4-Cl | isobutyryloxy | OH | Cl |
| 316. | N-C6H4-Cl | isobutyryloxy | OH | Br |
| 317. | N-C6H4-Cl | isobutyryloxy | isobutyryloxy | Cl |
| 318. | N-C6H4-Cl | isobutyryloxy | isobutyryloxy | Br |
| 319. | N-C6H4-Cl | OH | H | Cl |
| 320. | N-C6H4-Cl | OH | H | Br |
| 321. | N-C6H4-Cl | OH | OH | Cl |
| 322. | N-C6H4-Cl | OH | OH | Br |
| 323. | N-C6H4-Cl | OH | isobutyryloxy | Cl |
| 324. | N-C6H4-Cl | OH | isobutyryloxy | Br |

-continued
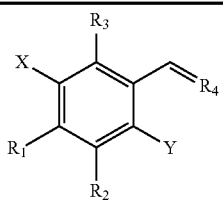
R1 = R3 = H
R4 is bonded though N, R2 in cases is bonded through O
| S.No | R4 | R2 | Y | X |
|---|---|---|---|---|
| 325. | N-(2,3-dichlorophenyl) | H | H | Cl |
| 326. | N-(2,3-dichlorophenyl) | H | H | Br |
| 327. | N-(2,3-dichlorophenyl) | H | OH | Cl |
| 328. | N-(2,3-dichlorophenyl) | H | OH | Br |
| 329. | N-(2,3-dichlorophenyl) | H | O-C(=O)-CH(CH3)- | Cl |
| 330. | N-(2,3-dichlorophenyl) | H | O-C(=O)-CH(CH3)- | Br |
| 331. | N-(2,3-dichlorophenyl) | O-C(=O)-C6H4-CH3 | H | Cl |
| 332. | N-(2,3-dichlorophenyl) | O-C(=O)-C6H4-CH3 | H | Br |

-continued

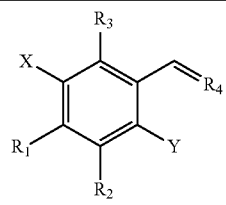

R1 = R3 = H

R4 is bonded though N, R2 in cases is bonded through O

| S.No | R4 | R2 | Y | X |
|---|---|---|---|---|
| 333. | 2,3-dichloroaniline (N-linked) | 4-methylbenzoate (O-linked) | OH | Cl |
| 334. | 2,3-dichloroaniline (N-linked) | 4-methylbenzoate (O-linked) | OH | Br |
| 335. | 2,3-dichloroaniline (N-linked) | 4-methylbenzoate (O-linked) | isobutyryloxy | Cl |
| 336. | 2,3-dichloroaniline (N-linked) | 4-methylbenzoate (O-linked) | isobutyryloxy | Br |
| 337. | 2,3-dichloroaniline (N-linked) | 3-methylbenzoate (O-linked) | H | Cl |
| 338. | 2,3-dichloroaniline (N-linked) | 3-methylbenzoate (O-linked) | H | Br |
| 339. | 2,3-dichloroaniline (N-linked) | 3-methylbenzoate (O-linked) | OH | Cl |

-continued

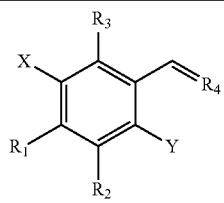

R1 = R3 = H

R4 is bonded though N, R2 in cases is bonded through O

| S.No | R4 | R2 | Y | X |
|---|---|---|---|---|
| 340. | 2,3-dichlorophenyl-N | 3-carboxylatophenyl-O | OH | Br |
| 341. | 2,3-dichlorophenyl-N | 3-carboxylatophenyl-O | O-C(=O)-CH(CH₃)₂ | Cl |
| 342. | 2,3-dichlorophenyl-N | 3-carboxylatophenyl-O | O-C(=O)-CH(CH₃)₂ | Br |
| 343. | 2,3-dichlorophenyl-N | nicotinate-O | H | Cl |
| 344. | 2,3-dichlorophenyl-N | nicotinate-O | H | Br |
| 345. | 2,3-dichlorophenyl-N | nicotinate-O | OH | Cl |
| 346. | 2,3-dichlorophenyl-N | nicotinate-O | OH | Br |

-continued

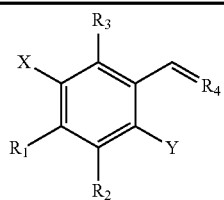

R1 = R3 = H

R₄ is bonded though N, R₂ in cases is bonded through O

| S.No | R4 | R2 | Y | X |
|------|-----|-----|-----|-----|
| 347. | 2,3-dichlorophenyl-N | nicotinoyloxy | isobutyryloxy | Cl |
| 348. | 2,3-dichlorophenyl-N | nicotinoyloxy | isobutyryloxy | Br |
| 349. | 2,3-dichlorophenyl-N | isobutyryloxy | H | Cl |
| 350. | 2,3-dichlorophenyl-N | isobutyryloxy | H | Br |
| 351. | 2,3-dichlorophenyl-N | isobutyryloxy | OH | Cl |
| 352. | 2,3-dichlorophenyl-N | isobutyryloxy | OH | Br |
| 353. | 2,3-dichlorophenyl-N | isobutyryloxy | isobutyryloxy | Cl |
| 354. | 2,3-dichlorophenyl-N | isobutyryloxy | isobutyryloxy | Br |

-continued
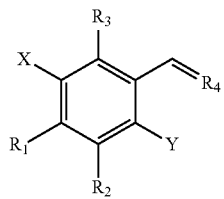
R1 = R3 = H
R4 is bonded though N, R2 in cases is bonded through O
| S.No | R4 | R2 | Y | X |
|---|---|---|---|---|
| 355. | 2,3-dichlorophenyl-N | OH | H | Cl |
| 356. | 2,3-dichlorophenyl-N | OH | H | Br |
| 357. | 2,3-dichlorophenyl-N | OH | OH | Cl |
| 358. | 2,3-dichlorophenyl-N | OH | OH | Br |
| 359. | 2,3-dichlorophenyl-N | OH | OC(O)CH(CH3)2 | Cl |
| 360. | 2,3-dichlorophenyl-N | OH | OC(O)CH(CH3)2 | Br |
| 361. | 3,5-dichlorophenyl-N | H | H | Cl |

-continued
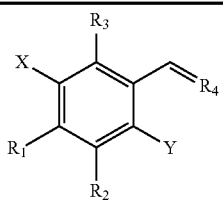
R1 = R3 = H
R4 is bonded though N, R2 in cases is bonded through O
| S.No | R4 | R2 | Y | X |
|---|---|---|---|---|
| 362. | N-(3,5-dichlorophenyl) | H | H | Br |
| 363. | N-(3,5-dichlorophenyl) | H | OH | Cl |
| 364. | N-(3,5-dichlorophenyl) | H | OH | Br |
| 365. | N-(3,5-dichlorophenyl) | H | O-C(=O)-CH(CH3)2 | Cl |
| 366. | N-(3,5-dichlorophenyl) | H | O-C(=O)-CH(CH3)2 | Br |
| 367. | N-(3,5-dichlorophenyl) | O-C(=O)-(4-methylphenyl) | H | Cl |
| 368. | N-(3,5-dichlorophenyl) | O-C(=O)-(4-methylphenyl) | H | Br |
| 369. | N-(3,5-dichlorophenyl) | O-C(=O)-(4-methylphenyl) | OH | Cl |

-continued

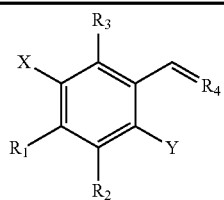

R1 = R3 = H

R4 is bonded though N, R2 in cases is bonded through O

| S.No | R4 | R2 | Y | X |
|---|---|---|---|---|
| 370. | N-(3,5-dichlorophenyl) | 4-methylbenzoate | OH | Br |
| 371. | N-(3,5-dichlorophenyl) | 4-methylbenzoate | isobutyryloxy-Cl | Cl |
| 372. | N-(3,5-dichlorophenyl) | 4-methylbenzoate | isobutyryloxy-Br | Br |
| 373. | N-(3,5-dichlorophenyl) | 3-methylbenzoate | H | Cl |
| 374. | N-(3,5-dichlorophenyl) | 3-methylbenzoate | H | Br |
| 375. | N-(3,5-dichlorophenyl) | 3-methylbenzoate | OH | Cl |
| 376. | N-(3,5-dichlorophenyl) | 3-methylbenzoate | OH | Br |

-continued
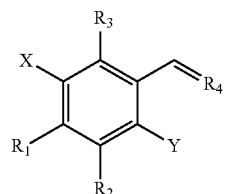
R1 = R3 = H
R4 is bonded though N, R2 in cases is bonded through O
| S.No | R4 | R2 | Y | X |
|---|---|---|---|---|
| 377. | N-(3,5-dichlorophenyl) | 3-methylbenzoate | OC(O)CH(CH3)2 | Cl |
| 378. | N-(3,5-dichlorophenyl) | 3-methylbenzoate | OC(O)CH(CH3)2 | Br |
| 379. | N-(3,5-dichlorophenyl) | nicotinate | H | Cl |
| 380. | N-(3,5-dichlorophenyl) | nicotinate | H | Br |
| 381. | N-(3,5-dichlorophenyl) | nicotinate | OH | Cl |
| 382. | N-(3,5-dichlorophenyl) | nicotinate | OH | Br |
| 383. | N-(3,5-dichlorophenyl) | nicotinate | OC(O)CH(CH3)2 | Cl |

-continued

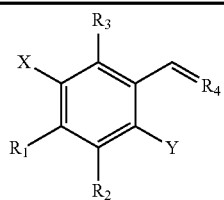

R1 = R3 = H

R4 is bonded though N, R2 in cases is bonded through O

| S.No | R4 | R2 | Y | X |
|---|---|---|---|---|
| 384. | N-(3,5-dichlorophenyl) | nicotinate (pyridine-3-carboxylate) | O-isobutyryl | Br |
| 385. | N-(3,5-dichlorophenyl) | O-isobutyryl | H | Cl |
| 386. | N-(3,5-dichlorophenyl) | O-isobutyryl | H | Br |
| 387. | N-(3,5-dichlorophenyl) | O-isobutyryl | OH | Cl |
| 388. | N-(3,5-dichlorophenyl) | O-isobutyryl | OH | Br |
| 389. | N-(3,5-dichlorophenyl) | O-isobutyryl | O-isobutyryl | Cl |
| 390. | N-(3,5-dichlorophenyl) | O-isobutyryl | O-isobutyryl | Br |
| 391. | N-(3,5-dichlorophenyl) | OH | H | Cl |

-continued
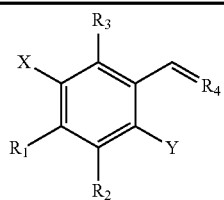
R1 = R3 = H
R₄ is bonded though N, R₂ in cases is bonded through O
| S.No | R4 | R2 | Y | X |
|---|---|---|---|---|
| 392. | 3,5-dichlorophenylamino | OH | H | Br |
| 393. | 3,5-dichlorophenylamino | OH | OH | Cl |
| 394. | 3,5-dichlorophenylamino | OH | OH | Br |
| 395. | 3,5-dichlorophenylamino | OH | OC(O)CH(CH₃)₂ | Cl |
| 396. | 3,5-dichlorophenylamino | OH | OC(O)CH(CH₃)₂ | Br |
| 397. | phenethylamino | H | H | Cl |
| 398. | phenethylamino | H | H | Br |
| 399. | phenethylamino | H | OH | Cl |
| 400. | phenethylamino | H | OH | Br |

-continued
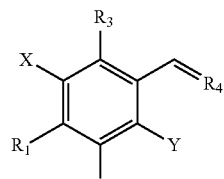
R1 = R3 = H
R4 is bonded though N, R2 in cases is bonded through O
| S.No | R4 | R2 | Y | X |
|---|---|---|---|---|
| 401. | N-CH2CH2-phenyl | H | -O-C(=O)-CH(CH3)2 | Cl |
| 402. | N-CH2CH2-phenyl | H | -O-C(=O)-CH(CH3)2 | Br |
| 403. | N-CH2CH2-phenyl | -O-C(=O)-C6H4-CH3 | H | Cl |
| 404. | N-CH2CH2-phenyl | -O-C(=O)-C6H4-CH3 | H | Br |
| 405. | N-CH2CH2-phenyl | -O-C(=O)-C6H4-CH3 | OH | Cl |
| 406. | N-CH2CH2-phenyl | -O-C(=O)-C6H4-CH3 | OH | Br |
| 407. | N-CH2CH2-phenyl | -O-C(=O)-C6H4-CH3 | -O-C(=O)-CH(CH3)2 | Cl |
| 408. | N-CH2CH2-phenyl | -O-C(=O)-C6H4-CH3 | -O-C(=O)-CH(CH3)2 | Br |

-continued
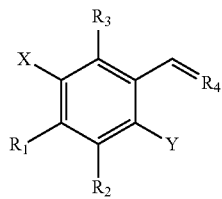
R1 = R3 = H
R₄ is bonded though N, R₂ in cases is bonded through O
| S.No | R4 | R2 | Y | X |
|---|---|---|---|---|
| 409. | N-CH₂CH₂-Ph | 3-methylbenzoate (O-linked) | H | Cl |
| 410. | N-CH₂CH₂-Ph | 3-methylbenzoate (O-linked) | H | Br |
| 411. | N-CH₂CH₂-Ph | 3-methylbenzoate (O-linked) | OH | Cl |
| 412. | N-CH₂CH₂-Ph | 3-methylbenzoate (O-linked) | OH | Br |
| 413. | N-CH₂CH₂-Ph | 3-methylbenzoate (O-linked) | isobutyrate (O-linked) | Cl |
| 414. | N-CH₂CH₂-Ph | 3-methylbenzoate (O-linked) | isobutyrate (O-linked) | Br |

-continued
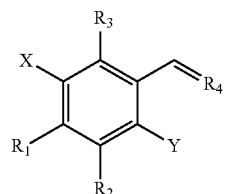
R1 = R3 = H
R4 is bonded though N, R2 in cases is bonded through O
| S.No | R4 | R2 | Y | X |
|---|---|---|---|---|
| 415. | N-CH2CH2-Ph | nicotinoyloxy | H | Cl |
| 416. | N-CH2CH2-Ph | nicotinoyloxy | H | Br |
| 417. | N-CH2CH2-Ph | nicotinoyloxy | OH | Cl |
| 418. | N-CH2CH2-Ph | nicotinoyloxy | OH | Br |
| 419. | N-CH2CH2-Ph | nicotinoyloxy | isobutyryloxy | Cl |
| 420. | N-CH2CH2-Ph | nicotinoyloxy | isobutyryloxy | Br |
| 421. | N-CH2CH2-Ph | isobutyryloxy | H | Cl |
| 422. | N-CH2CH2-Ph | isobutyryloxy | H | Br |

-continued

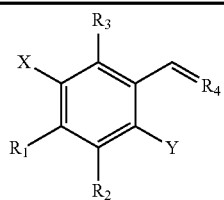

R1 = R3 = H

R4 is bonded though N, R2 in cases is bonded through O

| S.No | R4 | R2 | Y | X |
|---|---|---|---|---|
| 423. | N-CH2CH2-phenyl | OC(O)CH(CH3)2 | OH | Cl |
| 424. | N-CH2CH2-phenyl | OC(O)CH(CH3)2 | OH | Br |
| 425. | N-CH2CH2-phenyl | OC(O)CH(CH3)2 | OC(O)CH(CH3)2 | Cl |
| 426. | N-CH2CH2-phenyl | OC(O)CH(CH3)2 | OC(O)CH(CH3)2 | Br |
| 427. | N-CH2CH2-phenyl | OH | H | Cl |
| 428. | N-CH2CH2-phenyl | OH | H | Br |
| 429. | N-CH2CH2-phenyl | OH | OH | Cl |
| 430. | N-CH2CH2-phenyl | OH | OH | Br |
| 431. | N-CH2CH2-phenyl | OH | OC(O)CH(CH3)2 | Cl |
| 432. | N-CH2CH2-phenyl | OH | OC(O)CH(CH3)2 | Br |
| 433. | N-(4-(N,N-diethylaminomethyl)phenyl) | H | H | Cl |

-continued
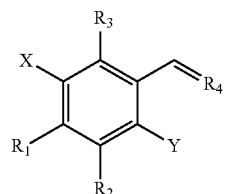
R1 = R3 = H
R4 is bonded though N, R2 in cases is bonded through O
| S.No | R4 | R2 | Y | X |
|---|---|---|---|---|
| 434. | N-C6H4-CH2-N(Et)2 | H | H | Br |
| 435. | N-C6H4-CH2-N(Et)2 | H | OH | Cl |
| 436. | N-C6H4-CH2-N(Et)2 | H | OH | Br |
| 437. | N-C6H4-CH2-N(Et)2 | H | OC(O)CH(CH3)2 | Cl |
| 438. | N-C6H4-CH2-N(Et)2 | H | OC(O)CH(CH3)2 | Br |
| 439. | N-C6H4-CH2-N(Et)2 | 4-methylbenzoate | H | Cl |
| 440. | N-C6H4-CH2-N(Et)2 | 4-methylbenzoate | H | Br |
| 441. | N-C6H4-CH2-N(Et)2 | 4-methylbenzoate | OH | Cl |
| 442. | N-C6H4-CH2-N(Et)2 | 4-methylbenzoate | OH | Br |

-continued
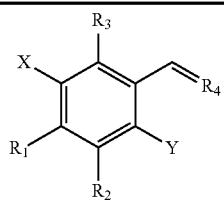
R1 = R3 = H
R₄ is bonded though N, R₂ in cases is bonded through O
| S.No | R4 | R2 | Y | X |
|---|---|---|---|---|
| 443. | N-C6H4-CH2-N(Et)2 | 4-methylbenzoate | OC(O)CH(CH3)2 | Cl |
| 444. | N-C6H4-CH2-N(Et)2 | 4-methylbenzoate | OC(O)CH(CH3)2 | Br |
| 445. | N-C6H4-CH2-N(Et)2 | 3-methylbenzoate | H | Cl |
| 446. | N-C6H4-CH2-N(Et)2 | 3-methylbenzoate | H | Br |
| 447. | N-C6H4-CH2-N(Et)2 | 3-methylbenzoate | OH | Cl |
| 448. | N-C6H4-CH2-N(Et)2 | 3-methylbenzoate | OH | Br |
| 449. | N-C6H4-CH2-N(Et)2 | 3-methylbenzoate | OC(O)CH(CH3)2 | Cl |

-continued

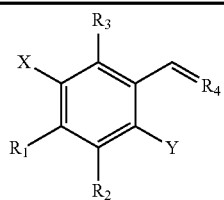

R1 = R3 = H

R4 is bonded though N, R2 in cases is bonded through O

| S.No | R4 | R2 | Y | X |
|---|---|---|---|---|
| 450. | 4-(N,N-diethylaminomethyl)phenyl-N | 3-methylbenzoate | OC(O)CH(CH3)2 | Br |
| 451. | 4-(N,N-diethylaminomethyl)phenyl-N | nicotinate | H | Cl |
| 452. | 4-(N,N-diethylaminomethyl)phenyl-N | nicotinate | H | Br |
| 453. | 4-(N,N-diethylaminomethyl)phenyl-N | nicotinate | OH | Cl |
| 454. | 4-(N,N-diethylaminomethyl)phenyl-N | nicotinate | OH | Br |
| 455. | 4-(N,N-diethylaminomethyl)phenyl-N | nicotinate | OC(O)CH(CH3)2 | Cl |
| 456. | 4-(N,N-diethylaminomethyl)phenyl-N | nicotinate | OC(O)CH(CH3)2 | Br |
| 457. | 4-(N,N-diethylaminomethyl)phenyl-N | isobutyrate | H | Cl |

-continued
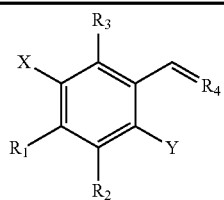
R1 = R3 = H
R4 is bonded though N, R2 in cases is bonded through O
| S.No | R4 | R2 | Y | X |
|---|---|---|---|---|
| 458. | N-C6H4-CH2-N(Et)2 | OC(O)CH(CH3)2 | H | Br |
| 459. | N-C6H4-CH2-N(Et)2 | OC(O)CH(CH3)2 | OH | Cl |
| 460. | N-C6H4-CH2-N(Et)2 | OC(O)CH(CH3)2 | OH | Br |
| 461. | N-C6H4-CH2-N(Et)2 | OC(O)CH(CH3)2 | OC(O)CH(CH3)2 | Cl |
| 462. | N-C6H4-CH2-N(Et)2 | OC(O)CH(CH3)2 | OC(O)CH(CH3)2 | Br |
| 463. | N-C6H4-CH2-N(Et)2 | OH | H | Cl |
| 464. | N-C6H4-CH2-N(Et)2 | OH | H | Br |
| 465. | N-C6H4-CH2-N(Et)2 | OH | OH | Cl |
| 466. | N-C6H4-CH2-N(Et)2 | OH | OH | Br |
| 467. | N-C6H4-CH2-N(Et)2 | OH | OC(O)CH(CH3)2 | Cl |
| 468. | N-C6H4-CH2-N(Et)2 | OH | OC(O)CH(CH3)2 | Br |

-continued
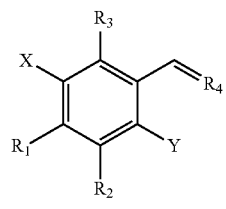
R1 = R3 = H
R4 is bonded though N, R2 in cases is bonded through O
| S.No | R4 | R2 | Y | X |
|---|---|---|---|---|
| 469. | 3-pyridyl-N | | H | H | Cl |
| 470. | 3-pyridyl-N | | H | H | Br |
| 471. | 3-pyridyl-N | | H | OH | Cl |
| 472. | 3-pyridyl-N | | H | OH | Br |
| 473. | 3-pyridyl-N | | H | isobutyryloxy | Cl |
| 474. | 3-pyridyl-N | | H | isobutyryloxy | Br |
| 475. | 3-pyridyl-N | | 4-methylbenzoyloxy | H | Cl |
| 476. | 3-pyridyl-N | | 4-methylbenzoyloxy | H | Br |
| 477. | 3-pyridyl-N | | 4-methylbenzoyloxy | OH | Cl |

-continued
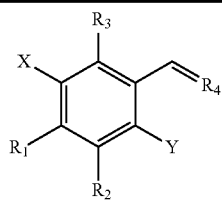
R1 = R3 = H
R4 is bonded though N, R2 in cases is bonded through O
| S.No | R4 | R2 | Y | X |
|---|---|---|---|---|
| 478. | 3-pyridyl-N | 4-methylbenzoate-O | OH | Br |
| 479. | 3-pyridyl-N | 4-methylbenzoate-O | isobutyryl-O | Cl |
| 480. | 3-pyridyl-N | 4-methylbenzoate-O | isobutyryl-O | Br |
| 481. | 3-pyridyl-N | 3-methylbenzoate-O | H | Cl |
| 482. | 3-pyridyl-N | 3-methylbenzoate-O | H | Br |
| 483. | 3-pyridyl-N | 3-methylbenzoate-O | OH | Cl |
| 484. | 3-pyridyl-N | 3-methylbenzoate-O | OH | Br |

-continued

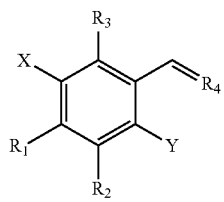

R1 = R3 = H

R4 is bonded though N, R2 in cases is bonded through O

| S.No | R4 | R2 | Y | X |
|---|---|---|---|---|
| 485. | 3-pyridyl (N-linked) | 3-methylbenzoate (O-linked) | OC(O)CH(CH3)2 | Cl |
| 486. | 3-pyridyl (N-linked) | 3-methylbenzoate (O-linked) | OC(O)CH(CH3)2 | Br |
| 487. | 3-pyridyl (N-linked) | nicotinate (O-linked) | H | Cl |
| 488. | 3-pyridyl (N-linked) | nicotinate (O-linked) | H | Br |
| 489. | 3-pyridyl (N-linked) | nicotinate (O-linked) | OH | Cl |
| 490. | 3-pyridyl (N-linked) | nicotinate (O-linked) | OH | Br |
| 491. | 3-pyridyl (N-linked) | nicotinate (O-linked) | OC(O)CH(CH3)2 | Cl |

-continued

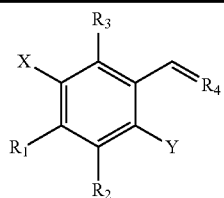

R1 = R3 = H

R4 is bonded though N, R2 in cases is bonded through O

| S.No | R4 | R2 | Y | X |
|---|---|---|---|---|
| 492. | 3-pyridyl-N | nicotinoyloxy | OC(O)CH(CH3)2 | Br |
| 493. | 3-pyridyl-N | isobutyryloxy | H | Cl |
| 494. | 3-pyridyl-N | isobutyryloxy | H | Br |
| 495. | 3-pyridyl-N | isobutyryloxy | OH | Cl |
| 496. | 3-pyridyl-N | isobutyryloxy | OH | Br |
| 497. | 3-pyridyl-N | isobutyryloxy | isobutyryloxy | Cl |
| 498. | 3-pyridyl-N | isobutyryloxy | isobutyryloxy | Br |
| 499. | 3-pyridyl-N | OH | H | Cl |
| 500. | 3-pyridyl-N | OH | H | Br |
| 501. | 3-pyridyl-N | OH | OH | Cl |

-continued
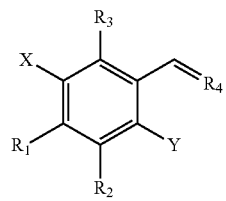
R1 = R3 = H
R₄ is bonded though N, R₂ in cases is bonded through O
| S.No | R4 | R2 | Y | X |
|---|---|---|---|---|
| 502. | 3-pyridyl-N | OH | OH | Br |
| 503. | 3-pyridyl-N | OH | OC(O)CH(CH₃) | Cl |
| 504. | 3-pyridyl-N | OH | OC(O)CH(CH₃) | Br |
| 505. | 3-COOH-phenyl-N | H | H | Cl |
| 506. | 3-COOH-phenyl-N | H | H | Br |
| 507. | 3-COOH-phenyl-N | H | OH | Cl |
| 508. | 3-COOH-phenyl-N | H | OH | Br |
| 509. | 3-COOH-phenyl-N | H | OC(O)CH(CH₃) | Cl |

-continued
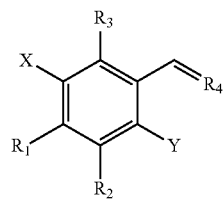
R1 = R3 = H
R4 is bonded though N, R2 in cases is bonded through O
| S.No | R4 | R2 | Y | X |
|---|---|---|---|---|
| 510. | N-C6H4-COOH (meta) | H | O-C(=O)-CH(CH3)2 | Br |
| 511. | N-C6H4-COOH (meta) | O-C(=O)-C6H4-CH3 (para) | H | Cl |
| 512. | N-C6H4-COOH (meta) | O-C(=O)-C6H4-CH3 (para) | H | Br |
| 513. | N-C6H4-COOH (meta) | O-C(=O)-C6H4-CH3 (para) | OH | Cl |
| 514. | N-C6H4-COOH (meta) | O-C(=O)-C6H4-CH3 (para) | OH | Br |
| 515. | N-C6H4-COOH (meta) | O-C(=O)-C6H4-CH3 (para) | O-C(=O)-CH(CH3)2 | Cl |
| 516. | N-C6H4-COOH (meta) | O-C(=O)-C6H4-CH3 (para) | O-C(=O)-CH(CH3)2 | Br |

-continued
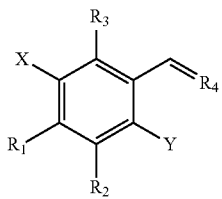
R1 = R3 = H
R4 is bonded though N, R2 in cases is bonded through O
| S.No | R4 | R2 | Y | X |
|---|---|---|---|---|
| 517. | N-C6H4-COOH | O-C(=O)-C6H4-CH3 | H | Cl |
| 518. | N-C6H4-COOH | O-C(=O)-C6H4-CH3 | H | Br |
| 519. | N-C6H4-COOH | O-C(=O)-C6H4-CH3 | OH | Cl |
| 520. | N-C6H4-COOH | O-C(=O)-C6H4-CH3 | OH | Br |
| 521. | N-C6H4-COOH | O-C(=O)-C6H4-CH3 | O-C(=O)-CH(CH3)2 | Cl |
| 522. | N-C6H4-COOH | O-C(=O)-C6H4-CH3 | O-C(=O)-CH(CH3)2 | Br |

-continued
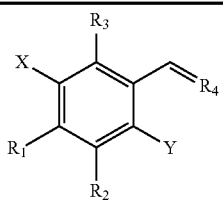
R1 = R3 = H
R4 is bonded though N, R2 in cases is bonded through O
| S.No | R4 | R2 | Y | X |
|---|---|---|---|---|
| 523. | 3-COOH-phenyl-N | nicotinoyl-O | H | Cl |
| 524. | 3-COOH-phenyl-N | nicotinoyl-O | H | Br |
| 525. | 3-COOH-phenyl-N | nicotinoyl-O | OH | Cl |
| 526. | 3-COOH-phenyl-N | nicotinoyl-O | OH | Br |
| 527. | 3-COOH-phenyl-N | nicotinoyl-O | isobutyryl-O | Cl |
| 528. | 3-COOH-phenyl-N | nicotinoyl-O | isobutyryl-O | Br |
| 529. | 3-COOH-phenyl-N | isobutyryl-O | H | Cl |
| 530. | 3-COOH-phenyl-N | isobutyryl-O | H | Br |

-continued
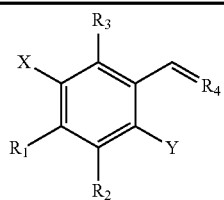
R1 = R3 = H
R4 is bonded though N, R2 in cases is bonded through O
| S.No | R4 | R2 | Y | X |
|---|---|---|---|---|
| 531. | N-(3-carboxyphenyl) | isobutyryloxy | OH | Cl |
| 532. | N-(3-carboxyphenyl) | isobutyryloxy | OH | Br |
| 533. | N-(3-carboxyphenyl) | isobutyryloxy | isobutyryloxy | Cl |
| 534. | N-(3-carboxyphenyl) | isobutyryloxy | isobutyryloxy | Br |
| 535. | N-(3-carboxyphenyl) | OH | H | Cl |
| 536. | N-(3-carboxyphenyl) | OH | H | Br |
| 537. | N-(3-carboxyphenyl) | OH | OH | Cl |
| 538. | N-(3-carboxyphenyl) | OH | OH | Br |

-continued

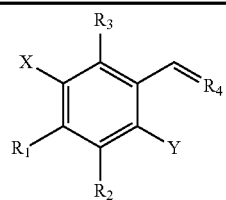

R1 = R3 = H

R$_4$ is bonded though N, R$_2$ in cases is bonded through O

| S.No | R4 | R2 | Y | X |
|------|----|----|----|---|
| 539. | (N-phenyl with COOH at meta) | OH | (isobutyryloxy C(=O)CH(CH$_3$)$_2$) | Cl |
| 540. | (N-phenyl with COOH at meta) | OH | (isobutyryloxy C(=O)CH(CH$_3$)$_2$) | Br |

Compounds where the double bond to R$_4$ is hydrogenated is represented below

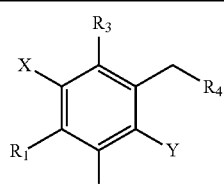

R1 = R3 = H

| S. No | R4 | R2 | Y | X |
|-------|----|----|----|---|
| 541. | (HN-CH(COOCH$_3$)-CH$_2$-C$_6$H$_4$-OH) | H | OH | Br |
| 542. | (HN-CH(COOCH$_3$)-CH(CH$_3$)$_2$) | H | OH | Br |

Preferred salts for the compounds listed above are hydrochloride, hydrobromide, sodium, potassium, or magnesium.

According to another feature of this present invention, there is provided a process for the preparation of the compound represented by the formula I, wherein all symbols are as defined as earlier, as shown in Scheme 1.

Scheme 1

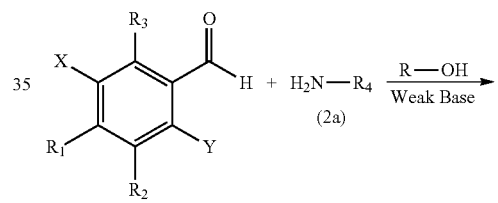

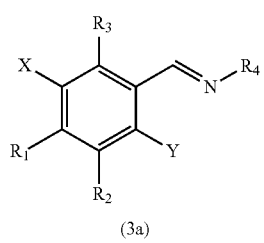

The reaction of a compound of general formula (1a) with a compound of general formula (2a) to produce a compound of the general formula (3a) may be carried out in an inert atmosphere which may be maintained by using inert gases such as nitrogen, argon or helium. The reaction may be carried out in a polar protic solvent like alcohols, preferably methanol or ethanol and in the presence of weak bases like DEA, TEA, Isopropylamine, pyridine, pipridine and the like, but more preferably with a base like TEA. The temperature of the reaction may range between 40 to 80° C., optimally between 60 to 80° C. and the duration may extend between 1 to 10 hours. The schiff base thus formed may be precipitated or could be extracted after suitable workup procedures such as water quenching. The resultant molecule is the halogenated benzylidine derivative of general formula (3a) where the groups have been defined earlier.

The invention is explained in detail in the examples given below which are provided by way of illustration only and therefore should not be construed to limit the scope of the invention.

Example 1

Synthesis of 2-[(5-Bromo-2-hydroxy-benzylidene)-amino]-3-(4-hydroxy-phenyl)-propionic acid methyl ester—(Compound 1)

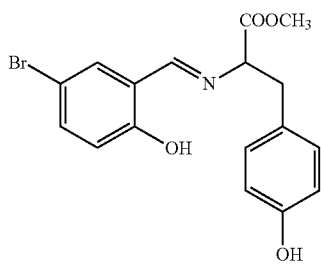 [SMILES: COC(=O)C(Cc1ccc(O)cc1)/N=C/c1cc(Br)ccc1O]

Step (i)

Synthesis of Tyrosine Methyl Ester Hydrochloride

Tyrosine (10.0 g) was taken in a clean and dry round bottom flask and methanol (100 ml) was added. Thionyl chloride (6.17 ml) was introduced in to the reaction mixture and it was refluxed at 70-80° C. for 6 hours with constant stirring. The excess solvent was then removed by distillation and the solid product obtained was stored under nitrogen. Yield—8.20 g

Step (ii)

Synthesis of 2-[(5-Bromo-2-hydroxy-benzylidene)-amino]-3-(4-hydroxy-phenyl)-propionic acid methyl ester Tyrosine methyl ester hydrochloride (8.30 g) and 5-bromo salicaldehyde (7.10 g) were taken in a clean and dry round bottom flask and methanol (100 ml) was added with constant stirring. Triethylamine (3 ml) was introduced in to the mixture and it was refluxed for 8 hours at 65-70° C. The excess solvent was then removed by distillation and the crude product was dissolved in water (150 ml). Ethyl acetate was used to extract the product from the solution and the separated organic layer was dried over sodium sulphate and then removed under reduced pressure to obtain the final product. Yield—3.14 g NMR—8.11 (1H, s), 7.62 (1H, s), 7.29 (1H, d), 6.95 (2H, d), 6.65 (3H, m), 5.0 (2H, s), 4.35 (1H, m), 3.67 (3H, s), 3.30 (1H, m)

Example 2

Synthesis of 2-[(5-Bromo-2-hydroxy-benzylidene)-amino]-3-methyl-butyric acid methyl ester—(Compound 2)

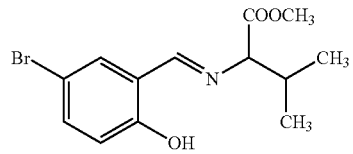 [SMILES: COC(=O)C(/N=C/c1cc(Br)ccc1O)C(C)C]

Step (i)

Synthesis of Valine Methyl Ester Hydrochloride

Valine (50.0 g) was taken in a clean and dry round bottom flask and methanol (150 ml) was added. Thionyl chloride (34.50 ml) was introduced in to the reaction mixture and it was refluxed at 70-80° C. for 6 hours with constant stirring. The excess solvent was then removed by distillation and the solid product obtained was stored under nitrogen. Yield—75.0 g

Step (ii)

Valine methyl ester hydrochloride (75.0 g) and 5-bromo salicaldehyde (50.0 g) were taken in a clean and dry round bottom flask and methanol (250 ml) was added with constant stirring. Triethylamine (50 ml) was introduced in to the mixture and it was refluxed for 8 hours at 65-70° C. Molecular sieves were also added to scavenge the water produced during the reaction. The reaction mass was then dissolved in acetone (200 ml) and filtered to remove the undissolved material. A solid precipitate was obtained when water (500 ml) was added to the filtrate. This was then filtered and dried. Yield—54.6 g.

NMR—8.13 (1H, s), 7.62 (1H, s), 7.29 (1H, d), 6.65 (1H, d), 5.0 (1H, s), 3.95 (1H, s), 3.67 (3H, s), 2.50 (1H, m), 1.10 (1H, d)

Example 3

Synthesis of 2-(5-Bromo-2-hydroxy-benzylamino]-3-(4-hydroxy-phenyl)-propionic acid methyl ester (Compound 3)

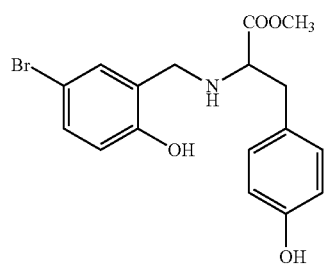 [SMILES: COC(=O)C(Cc1ccc(O)cc1)NCc1cc(Br)ccc1O]

Step (i)

Synthesis of Tyrosine Methyl Ester Hydrochloride

Tyrosine (10.0 g) was taken in a clean and dry round bottom flask and methanol (100 ml) was added. Thionyl chloride (6.17 ml) was introduced in to the reaction mixture and it was refluxed at 70-80° C. for 6 hours with constant stirring. The excess solvent was then removed by distillation and the solid product obtained was stored under nitrogen. Yield—8.20 g Step (ii)

Synthesis of 2-[(5-Bromo-2-hydroxy-benzylidene)-amino]-3-(4-hydroxy-phenyl)-propionic acid methyl ester Tyrosine methyl ester hydrochloride (8.30 g) and 5-bromo salicaldehyde (7.10 g) were taken in a clean and dry round bottom flask and methanol (100 ml) was added with constant stirring. Triethylamine (3 ml) was introduced in to the mixture and it was refluxed for 8 hours at 65-70° C. The excess solvent was then removed by distillation and the crude product was dissolved in water (150 ml). Ethyl acetate was used to extract the product from the solution and the separated organic layer was dried over sodium sulphate and then removed under reduced pressure to obtain the product. Yield—3.14 g Step (iii)

2-[(5-Bromo-2-hydroxy-benzylidene)-amino]-3-(4-hydroxy-phenyl)-propionic acid methyl ester (6.01 g) was taken in a clean and dry round bottom flask and methanol (50 ml) was added with constant stirring. Sodium borohydride (4.05 g) was added lot by lot and the reaction mixture was stirred for 2 hours under room temperature. The solvent was removed completely and the reaction mass was acidified with 20% HCl solution. The product was extracted using ethylacetate and the separated organic layer was washed with water. It was then dried over sodium sulphate and evaporated under nitrogen to obtain the final product. Yield—3.85 g.
NMR—6.50-7.06 (Aromatic), 5.0 (2H, s), 3.81 (3H, s), 3.14 (1H, m), 2.0 (1H, s)

Example 4

Synthesis of 2-[(5-Bromo-2-hydroxy-benzylidene)-amino]-3-(4-hydroxy-phenyl)-propionic acid (Compound 4)

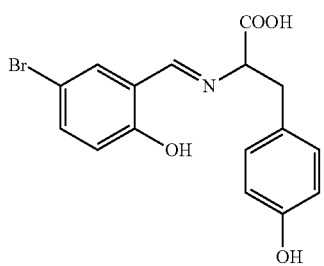 [SMILES: O=C(O)C(Cc1ccc(O)cc1)/N=C/c1cc(Br)ccc1O]

Step (i)

Synthesis of Tyrosine Methyl Ester Hydrochloride

Tyrosine (10.0 g) was taken in a clean and dry round bottom flask and methanol (100 ml) was added. Thionyl chloride (6.17 ml) was introduced in to the reaction mixture and it was refluxed at 70-80° C. for 6 hours with constant stirring. The excess solvent was then removed by distillation and the solid product obtained was stored under nitrogen. Yield—8.20 g Step (ii)

Synthesis of 2-[(5-Bromo-2-hydroxy-benzylidene)-amino]-3-(4-hydroxy-phenyl)-propionic acid methyl ester Tyrosine methyl ester hydrochloride (8.30 g) and 5-bromo salicaldehyde (7.10 g) were taken in a clean and dry round bottom flask and methanol (100 ml) was added with constant stirring. Triethylamine (3 ml) was introduced in to the mixture and it was refluxed for 8 hours at 65-70° C. The excess solvent was then removed by distillation and the crude product was dissolved in water (150 ml). Ethyl acetate was used to extract the product from the solution and the separated organic layer was dried over sodium sulphate and then removed under reduced pressure to obtain the product. Yield—3.14 g Step (iii)

2-[(5-Bromo-2-hydroxy-benzylidene)-amino]-3-(4-hydroxy-phenyl)-propionic acid methyl ester (5.0 g) was taken in a clean and dry round bottom flask and NaOH solution (3.69 g/66 ml) was added to it with constant stirring. Acetone (33 ml) was added and the mixture was maintained at room temperature for 3 hours. The reaction mixture was then cooled to 25° C. and the pH was brought to 5.5 using 1:1 HCl solution. The precipitated solid was filtered, washed with water followed by hexane and dried. Yield 2.50 g
NMR—10.21 (1H, s), 8.11 (1H, s), 6.50-7.62 (Aromatic), 5.0 (2H, s), 4.39 (1H, m), 3.02 (1H)

Example 5

Synthesis of 4-Bromo-2-{[1-hydroxymethyl-2-(4-hydroxy-phenyl)-ethylimino]-methyl}-phenol (Compound 5)

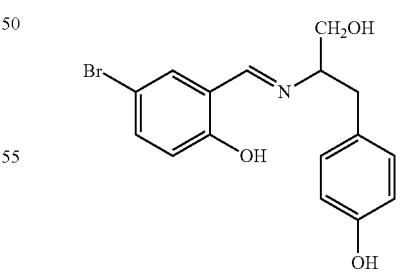

Step (i)

Synthesis of Tyrosinol

Tyrosine (30.0 g) was taken in a clean and dry round bottom flask and tetrahydrofuran (40 ml) was added with constant stirring. Boron trifluoride ethyl ether complex (21 ml) and borane dimethylsulphide (34.5 ml) were added and the reaction mixture was refluxed at 40-50° C. for 18 hours. 6 M NaOH solution was added to the reaction mixture and it was then saturated with potassium carbonate. Chloroform was used to extract the product and the organic layer was washed with water and dried over sodium sulphate. The chloroform was then evaporated to obtain the product. Yield 7.5 g.

Step (ii)

Tyrosinol (7.50 g) and 5-bromo salicaldehyde (4.50 g) were taken in a clean and dry round bottom flask and methanol (100 ml) was added with constant stirring. The mixture was refluxed for 4 hours at 65-70° C. The excess solvent was then removed by distillation and the crude product was dissolved in water (150 ml). Chloroform was used to extract the product from the solution and the separated organic layer was dried over sodium sulphate and then removed under reduced pressure to obtain the final product. Yield—4.36 g NMR—10.21 (1H, s), 8.11 (1H, s), 6.50-7.62 (Aromatic), 5.0 (2H, s), 4.39 (1H, m), 3.02 (1H)

Example 6

Synthesis of 2-(5-Bromo-2-hydroxy-benzylamino)-3-methyl-butyric acid methyl ester (Compound 6)

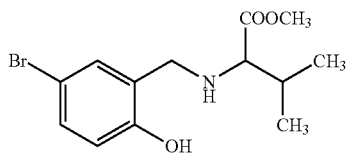 [SMILES: COC(=O)C(NCc1cc(Br)ccc1O)C(C)C]

Step (i)

Synthesis of Valine Methyl Ester Hydrochloride

Valine (50.0 g) was taken in a clean and dry round bottom flask and methanol (150 ml) was added. Thionyl chloride (34.50 ml) was introduced in to the reaction mixture and it was refluxed at 70-80° C. for 6 hours with constant stirring. The excess solvent was then removed by distillation and the solid product obtained was stored under nitrogen. Yield—75.0 g Step (ii)

Valine methyl ester hydrochloride (75.0 g) and 5-bromo salicaldehyde (50.0 g) were taken in a clean and dry round bottom flask and methanol (250 ml) was added with constant stirring. Triethylamine (50 ml) was introduced in to the mixture and it was refluxed for 8 hours at 65-70° C. Molecular sieves were also added to scavenge the water produced during the reaction. The reaction mass was then dissolved in acetone (200 ml) and filtered to remove the undissolved material. A solid precipitate was obtained when water (500 ml) was added to the filtrate. This was then filtered and dried. Yield—54.6 g.

Step (iii)

2-[(5-Bromo-2-hydroxy-benzylidene)-amino]-3-methyl-butyric acid methyl ester (1.3 g) was taken in a clean and dry round bottom flask and methanol (50 ml) was added with constant stirring. Sodium borohydride (0.8 g) was added lot by lot and the reaction mixture was stirred for 2 hours under room temperature. The solvent was removed completely and the reaction mass was acidified with 20% HCl solution. The product was extracted using ethylacetate and the separated organic layer was washed with water. It was then dried over sodium sulphate and evaporated under nitrogen to obtain the final product. Yield—1.0 g.

NMR—6.50-7.07 (Aromatic), 5.0 (1H, s), 3.81 (2H, d), 3.67 (3H, s), 3.44 (1H, d), 2.70 (1H, m), 2.0 (1H, d), 1.12 (6H, d)

Example 7

Synthesis of 2-[(5-Bromo-2-hydroxy-benzylidene)-amino]-3-methyl-butyric acid (Compound 7)

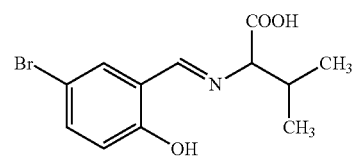 [SMILES: CC(C)C(/N=C/c1cc(Br)ccc1O)C(=O)O]

Step (i)

Synthesis of Valine Methyl Ester Hydrochloride

Valine (50.0 g) was taken in a clean and dry round bottom flask and methanol (150 ml) was added. Thionyl chloride (34.50 ml) was introduced in to the reaction mixture and it was refluxed at 70-80° C. for 6 hours with constant stirring. The excess solvent was then removed by distillation and the solid product obtained was stored under nitrogen. Yield—75.0 g Step (ii)

Valine methyl ester hydrochloride (75.0 g) and 5-bromo salicaldehyde (50.0 g) were taken in a clean and dry round bottom flask and methanol (250 ml) was added with constant stirring. Triethylamine (50 ml) was introduced in to the mixture and it was refluxed for 8 hours at 65-70° C. Molecular sieves were also added to scavenge the water produced during the reaction. The reaction mass was then dissolved in acetone (200 ml) and filtered to remove the undissolved material. A solid precipitate was obtained when water (500 ml) was added to the filtrate. This was then filtered and dried. Yield—54.6 g.

Step (iii)

2-[(5-Bromo-2-hydroxy-benzylidene)-amino]-3-methyl-butyric acid methyl (9.0 g) was taken in a clean and dry round bottom flask and NaOH solution (3.69 g/120 ml) was added to it with constant stirring. Acetone (90 ml) was added and the mixture was maintained at room temperature for 3 hours. The reaction mixture was then cooled to 25° C. and the pH was brought to 5.5 using 1:1 HCl solution. The precipitated solid was filtered, washed with water followed by hexane and dried. Yield 5.80 g NMR—10.21 (1H, s), 8.13 (1H, s), 6.65-7.62 (Aromatic), 5.0 (1H, s), 3.89 (1H, d), 2.04 (1H, m), 1.12 (6H, d)

Example 8

Synthesis of 4-Bromo-2-[(1-hydroxymethyl-2-methyl-propylimino)-methyl]-phenol (Compound 8)

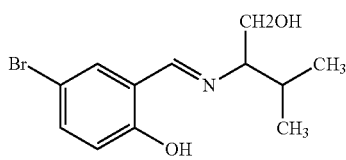 [SMILES: CC(C)C(CO)/N=C/c1cc(Br)ccc1O]

Step (i)

Synthesis of Valinol

Valine (11.7 g) was taken in a clean and dry round bottom flask and tetrahydrofuran (100 ml) was added with constant stirring. Boron trifluoride ethyl ether complex 14.2 ml) and borane dimethylsulphide (10 ml) were added and the reaction mixture was refluxed at 40-50° C. for 4 hours. The reaction mixture was acidified with 0.5N HCl and the THF layer was separated and washed twice with water. The solvent was then dried over sodium sulphate and evaporated to obtain the product. Yield 8.0 g.

Step (ii)

Valinol (10 g) and 5-bromo salicaldehyde (4.0 g) were taken in a clean and dry round bottom flask and methanol (100 ml) was added with constant stirring. TEA (1.0 ml) was added and the mixture was refluxed for 4 hours at 65-70° C. The excess solvent was then removed by distillation and the crude product was dissolved in water (150 ml). Chloroform was used to extract the product from the solution and the separated organic layer was dried over sodium sulphate and then removed under reduced pressure to obtain the final product. Yield—5.2 g NMR—6.65-7.62 (Aromatic), 5.0 (1H, s), 3.89 (1H, d), 2.04 (1H, m), 1.12 (6H, d)

Example 9

Synthesis of 4-Methyl-benzoic acid 4-bromo-2-[(4-chloro-phenylimino)-methyl]-phenyl ester (Compound 9)

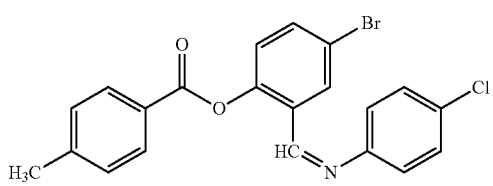 [SMILES: Cc1ccc(C(=O)Oc2ccc(Br)cc2/C=N\c2ccc(Cl)cc2)cc1]

Step (i)

Synthesis of 4-Methyl-benzoic acid 4-bromo-2-formyl-phenyl ester (Compound 9)

5-bromo salicyaldehyde (5.0 g) was taken in a clean and dry round bottom flask and chloroform (50 ml) was added with constant stirring. The reaction mixture was cooled to 10-15° C. and p-toulyl chloride (3.62 ml) was added drop wise. Stirring was continued for 15 minutes and TEA (3.0 ml) was added and the reaction was allowed to proceed for 4 hours. The reaction mixture was then transferred to a separating funnel and washed twice with water. The separated organic layer was then washed with 5% NaOH solution and then dried over sodium sulphate. The chloroform was 80% evaporated and hexane was added to obtain a solid precipitate. This precipitate was filtered and dried. Yield 7.2 g.

Step (ii)

Synthesis of 4-Methyl-benzoic acid 4-bromo-2-[(4-chloro-phenylimino)-methyl]-phenyl ester 4-Methyl-benzoic acid 4-bromo-2-formyl-phenyl ester (4.0 g) and 4-chloro aniline (1.9 g) were taken in a clean and dry round bottom flask and methanol (40 ml) was added to it. The reaction mixture was refluxed at 60-80° C. for 3 hours following which it was transferred to a beaker containing 100 ml water and stirred for 15 minutes. The solid precipitate formed was filtered, washed with water, followed by hexane and dried. Yield 3.6 g.

NMR—8.39 (1H, s), 7.07-8.02 (Aromatic), 2.35 (3H, s)

Example 10

Synthesis of 3-Methyl-benzoic acid 4-bromo-2-[(2,3-dichloro-phenylimino)-methyl]-phenyl ester (Compound 10)

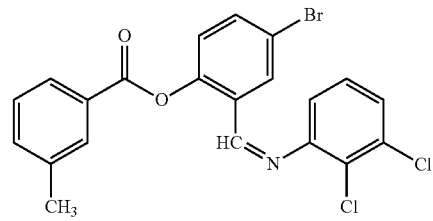 [SMILES: Cc1cccc(C(=O)Oc2ccc(Br)cc2/C=N\c2cccc(Cl)c2Cl)c1]

Step (i)

Synthesis of 3-Methyl-benzoic acid 4-bromo-2-formyl-phenyl ester 5-bromo salicyaldehyde (5.0 g) was taken in a clean and dry round bottom flask and chloroform (50 ml) was added with constant stirring. The reaction mixture was cooled to 10-15° C. and m-toulyl chloride (3.62 ml) was added drop wise. Stirring was continued for 15 minutes and TEA (3.0 ml) was added and the reaction was allowed to proceed for 4 hours. The reaction mixture was then transferred to a separating funnel and washed twice with water. The separated organic layer was then washed with 5% NaOH solution and then dried over sodium sulphate. The chloroform was 80% evaporated and hexane was added to obtain a solid precipitate. This precipitate was filtered and dried. Yield 7.2 g.

Step (ii)

Synthesis of 3-Methyl-benzoic acid 4-bromo-2-[(2, 3-dichloro-phenylimino)-methyl]-phenyl ester 3-Methyl-benzoic acid 4-bromo-2-formyl-phenyl ester (4.0 g) and 2,3-dichloro aniline (1.9 g) were taken in a clean and dry round bottom flask and methanol (40 ml) was added to it. The reaction mixture was refluxed at 60-80° C. for 3 hours following which it was transferred to a beaker containing 100 ml water and stirred for 15 minutes. The solid precipitate formed was filtered, washed with water, followed by hexane and dried. Yield 3.6 g.

NMR—8.39 (1H, s), 7.01-7.90 (Aromatic), 2.35 (3H, s)

Example 11

Synthesis of [5-Bromo-2-(1-m-tolyl-vinyloxy)-benzylidine]-pyridin-3-yl-amine (Compound 11)

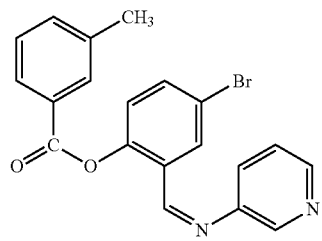 [SMILES: Cc1cccc(C(=O)Oc2ccc(Br)cc2/C=N\c2cccnc2)c1]

Step (i)

Synthesis of 4-Bromo-2-(pyridine-3-yliminomethyl)-phenol 5-bromo salicyaldehyde (10.0 g) and 3-amino pyridine (5.85 g) were taken in a clean and dry round bottom flask and methanol (150 ml) was added with constant stirring. The reaction was refluxed at 60° C. for 6 hours. The solid product formed was filtered and washed with water, followed by hexane and dried. Yield 8.25 g.

Step (ii)

4-Bromo-2-(pyridine-3-yliminomethyl)-phenol (5.0 g) was taken in a clean and dry round bottom flask and chloroform (100 ml) was added to it. The reaction mixture was cooled to 10° C. and m-toulyl chloride (3.62 ml) was added drop wise followed by the addition of TEA (3.58 ml). The reaction was then allowed to proceed for 6 hours at room temperature. It was then quenched by adding water. The chloroform layer was separated and washed twice with 10% NaOH solution following which it was dried over sodium sulphate and concentrated. Hexane was added to the cooled and concentrated organic layer to obtain the solid precipitate. This was then filtered and dried. Yield 4.6 g.

NMR—8.60 (1H, s), 8.1 (1H, s), 7.10-7.95 (Aromatic), 2.35 (3H, s)

Example 12

Synthesis of Nicotinic acid-4-bromo-2[(3-carboxy-phenylimino)-methyl]-phenyl ester (Compound 12)

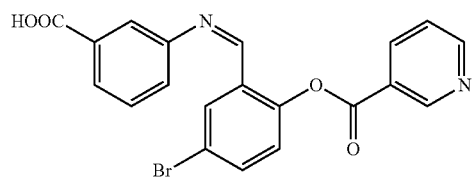 [SMILES: O=C(O)c1cccc(/N=C\c2cc(Br)ccc2OC(=O)c2cccnc2)c1]

Step (i)

Synthesis of Nicotonyl Chloride

Nicotinic acid (20.0 g) was taken in a clean and dry round bottom flask and thionyl chloride (75 ml) was added with constant stirring. The reaction was allowed to proceed for 5 hours at 70-80° C. following which the excess thionyl chloride was distilled off. Hexane was added and redistillation was performed to remove trace amounts of thionyl chloride. Yield 28.0 g.

Step (ii)

Synthesis of Nicotinicacid-4-bromo-2-formyl-phenyl ester 5-bromo salicaldehyde (20.0 g) was taken in a clean and dry round bottom flask and chloroform (75 ml) was added with constant stirring. The temperature was brought down to 5-10° C. Nicotonyl chloride (17.5 g) was added to the reaction mixture and stirred for 15 minutes. TEA (11.32 ml) was added drop wise and the reaction was allowed to stir for 6 hours at room temperature and the quenched by transferring it to a beaker containing water. The organic layer was separated and washed with water and dried over sodium sulphate. The solvent was then removed to obtain the solid product was then filtered and dried. Yield 12.0 g.

Step (iii)

Synthesis of Synthesis of Nicotinic acid-4-bromo-2 [(3-carboxy-phenylimino)-methyl]-phenyl ester Nicotinic acid-4-bromo-2-formyl-phenyl ester (1.5 g) was taken in a clean and dry round bottom flask and methanol (30 ml) was added. The reaction mixture was stirred over an oil bath and 3-amino benzoic acid (0.715 g) was introduced lot by lot. Stirring was continued for 5 hours at 60-80° C. following which the reaction was quenched by transferring it to a beaker containing water. The solid precipitate thus formed was washed with water followed by hexane, filtered and dried. Final product yield 0.72 g.

NMR—11.01 (1H, s), 9.10 (1H, s), 8.79 (1H, d), 8.35 (1H, s), 8.17 (1H, d), 7.60-8.10 (aromatic), 7.62 (1H, s), 6.51 (1H, d)

The invention claimed is:

1. A compound of formula (I),

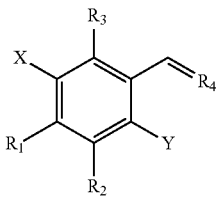

Formula I wherein
R1=H,
R2=H,
R3=H,
X=Br or Cl,
Y=OH,
and R4=

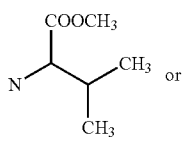

(Compound 2)

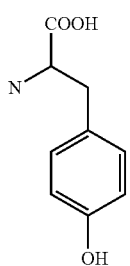

(Compound 4)

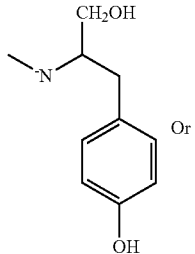

Or (Compound 5)

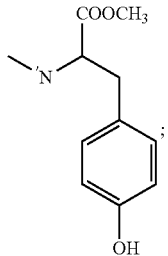

(Compound 1)

and a pharmaceutically acceptable salt thereof.

2. The compound of claim 1 comprising:
2-[(5-Bromo-2-hydroxy-benzylidene)-amino]-3-methyl-butyric acid methyl ester

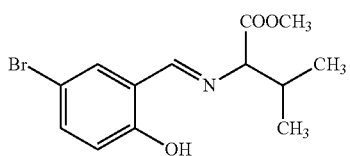

(Compound 2)

3. The compound of claim 1 comprising:
2-[(5-Bromo-2-hydroxy-benzylidene)-amino]-3-(4-hydroxy-phenyl)-propionic acid

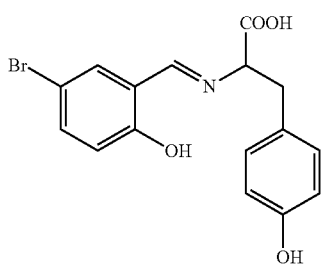

(Compound 4)

4. The compound of claim 1 comprising:
4-Bromo-2-[1-hydroxymethyl-2-(4-hydroxy-phenyl)-ethylimino]-methyl]-phenol (Compound 5)

5. The compound of claim 1 comprising:
2-[(5-Bromo-2-hydroxy-benzylidene)-amino]-3-(4-hydroxy-phenyl)-propionic acid methyl ester (Compound 1)

* * * * *